(12) United States Patent
Nicula et al.

(10) Patent No.: US 11,783,915 B2
(45) Date of Patent: *Oct. 10, 2023

(54) CONVOLUTIONAL NEURAL NETWORK SYSTEMS AND METHODS FOR DATA CLASSIFICATION

(71) Applicant: GRAIL, LLC, Menlo Park, CA (US)

(72) Inventors: Virgil Nicula, Cupertino, CA (US); Anton Valouev, Palo Alto, CA (US); Darya Filippova, Sunnyvale, CA (US); Matthew H. Larson, San Francisco, CA (US); M. Cyrus Maher, San Mateo, CA (US); Monica Portela dos Santos Pimentel, San Jose, CA (US); Robert Abe Paine Calef, Redwood City, CA (US); Collin Melton, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/936,529

(22) Filed: Sep. 29, 2022

(65) Prior Publication Data

US 2023/0045925 A1 Feb. 16, 2023

Related U.S. Application Data

(63) Continuation of application No. 16/428,575, filed on May 31, 2019, now Pat. No. 11,482,303.
(Continued)

(51) Int. Cl.
*G16B 30/10* (2019.01)
*G16H 50/20* (2018.01)
(Continued)

(52) U.S. Cl.
CPC .............. *G16B 30/10* (2019.02); *G06N 3/04* (2013.01); *G06N 3/084* (2013.01); *G16B 40/20* (2019.02); *G16B 40/30* (2019.02); *G16H 50/20* (2018.01)

(58) Field of Classification Search
CPC ........ G16B 30/10; G16B 40/20; G16B 40/30; G16B 20/20; G16B 25/10; G16B 20/00;
(Continued)

(56) References Cited

U.S. PATENT DOCUMENTS 6,466,923 B1 * 10/2002 Young .................... G16B 25/20
382/103
8,642,349 B1 2/2014 Yeatman et al.
(Continued)

FOREIGN PATENT DOCUMENTS

AU 2015360298 A1 9/2018
CN 106795562 A 5/2017
(Continued)

OTHER PUBLICATIONS

Nello Cristianini et al., "An Introduction to Support Vector Machines and other kernel-based learning methods", Cambridge University Press, First Published 2000, pp. 93-124.
(Continued)

*Primary Examiner* — Nimesh Patel
(74) *Attorney, Agent, or Firm* — Bookoff McAndrews, PLLC

(57) ABSTRACT

Classification of cancer condition, in a plurality of different cancer conditions, for a species, is provided in which, for each training subject in a plurality of training subjects, there is obtained a cancer condition and a genotypic data construct including genotypic information for the respective training subject. Genotypic constructs are formatted into corresponding vector sets comprising one or more vectors. Vector sets (Continued)

are provided to a network architecture including a convolutional neural network path comprising at least a first convolutional layer associated with a first filter that comprise a first set of filter weights and a scorer. Scores, corresponding to the input of vector sets into the network architecture, are obtained from the scorer. Comparison of respective scores to the corresponding cancer condition of the corresponding training subjects is used to adjust the filter weights thereby training the network architecture to classify cancer condition.

40 Claims, 47 Drawing Sheets

Related U.S. Application Data

(60) Provisional application No. 62/679,746, filed on Jun. 1, 2018.

(51) Int. Cl.
*G16B 40/30* (2019.01)
*G16B 40/20* (2019.01)
*G06N 3/04* (2023.01)
*G06N 3/084* (2023.01)

(58) Field of Classification Search
CPC ........ G16B 30/00; G16B 40/00; G16B 20/40; G16B 20/10; G16B 30/20; G16B 5/00; G16B 50/00; G16B 20/30; G16B 45/00; G16B 50/30; G16B 50/40; G06N 3/04; G06N 3/084; G06N 5/003; G06N 20/20; G06N 3/126; G06N 20/10; G06N 3/0454; G06N 3/08; G06N 20/00; G06N 3/02; G06N 7/005; G06N 3/0472; G06N 5/025; G06N 3/0427; G06N 3/0445; G16H 50/20; G16H 50/30; G16H 30/40; G16H 10/40; G16H 50/70; G16H 50/50; G16H 15/00; G16H 10/60; G16H 20/00; G16H 50/00; G16H 80/00; G06T 7/0012; G06T 2207/20081; G06T 2207/30024; G06T 2207/20084; G06T 2207/30068; G06T 2207/10116; G06T 2207/10056; G06T 2207/10081; G06T 2207/30096; G06T 7/11; G06T 2207/10088; G06T 2207/30004; G06T 7/187; G06T 7/30; G06T 5/002; G06T 2200/04; G06T 19/20; G06T 17/00; G06T 15/00; G06T 2207/20221; G06T 2207/300008; G06T 2207/30016; G06T 2207/30061; G06T 2207/30088; G06T 7/00; G06T 7/33; G06T 7/337; G06T 7/35; G06T 7/44; G06V 2201/03; G06V 20/698; G06V 10/82; G06V 20/695; G06V 30/19147; G06V 10/443; G06V 10/70; G06V 10/774; G06V 10/88; G06V 30/19173; G06V 10/764; G06V 10/267; G06V 10/993; G06V 20/69; G06V 20/47; G06V 10/751; G06V 10/454; G06K 9/6256; G06K 9/623; G06K 9/6247; G06K 9/6267; G06K 9/629; G06K 9/6223; G06K 9/6276; G06K 9/6273; G06K 9/6272; G06K 9/6269; G06K 9/6278; G06K 9/6296; G06K 9/6268; G06K 9/6218; G06K 9/6222; G06K 9/6262; G06K 9/6277; G06K 9/628; C12Q 1/6883; C12Q 1/6827; C12Q 1/6816; C12Q 1/6886; C12Q 2600/118; C12Q 1/701; C12Q 2600/112; A61B 5/0006; A61B 5/318; A61B 5/4064; A61B 5/7267; A61B 5/7275; A61B 5/742
See application file for complete search history.

(56) References Cited

U.S. PATENT DOCUMENTS

| | | | |
|---|---|---|---|
| 8,706,422 | B2 | 4/2014 | Lo et al. |
| 9,260,745 | B2 | 2/2016 | Rava et al. |
| 9,373,059 | B1 | 6/2016 | Heifets et al. |
| 10,457,995 | B2 | 10/2019 | Talasaz |
| 2003/0215120 | A1* | 11/2003 | Uppaluri ................ A61B 6/505 382/128 |
| 2010/0112590 | A1 | 5/2010 | Lo et al. |
| 2010/0145894 | A1 | 6/2010 | Semizarov et al. |
| 2012/0053253 | A1* | 3/2012 | Stone ................... C12Q 1/6886 514/789 |
| 2013/0034546 | A1 | 2/2013 | Rava et al. |
| 2013/0325360 | A1 | 12/2013 | Deciu et al. |
| 2014/0066317 | A1 | 3/2014 | Talasaz |
| 2014/0080715 | A1 | 3/2014 | Lo et al. |
| 2014/0100121 | A1 | 4/2014 | Lo et al. |
| 2014/0242588 | A1 | 8/2014 | Van Den Boom et al. |
| 2014/0371078 | A1 | 12/2014 | Abdueva |
| 2015/0102216 | A1 | 4/2015 | Röder et al. |
| 2015/0220838 | A1* | 8/2015 | Martin ................... G16B 20/00 706/12 |
| 2016/0002739 | A1 | 1/2016 | Shutz et al. |
| 2016/0232290 | A1 | 8/2016 | Rava et al. |
| 2016/0251704 | A1 | 9/2016 | Talasaz et al. |
| 2016/0364522 | A1 | 12/2016 | Frey et al. |
| 2017/0107576 | A1 | 4/2017 | Babiarz et al. |
| 2017/0121767 | A1 | 5/2017 | Dor et al. |
| 2017/0220735 | A1 | 8/2017 | Duenwald et al. |
| 2017/0240973 | A1 | 8/2017 | Eltoukhy et al. |
| 2017/0270245 | A1 | 9/2017 | Van Rooyen et al. |
| 2017/0329893 | A1 | 11/2017 | Di Iulio et al. |
| 2017/0342477 | A1 | 11/2017 | Jensen et al. |
| 2017/0342500 | A1 | 11/2017 | Maquard et al. |
| 2017/0362638 | A1 | 12/2017 | Chudova et al. |
| 2018/0046851 | A1 | 2/2018 | Kienzle et al. |
| 2018/0144261 | A1 | 5/2018 | Wnuk et al. |
| 2018/0148777 | A1 | 5/2018 | Kirkizlar et al. |
| 2018/0173845 | A1 | 6/2018 | Sigurjonsson et al. |
| 2019/0106737 | A1 | 4/2019 | Underhill |
| 2019/0164627 | A1 | 5/2019 | Blocker et al. |
| 2019/0287646 | A1 | 9/2019 | Hubbell |
| 2019/0287649 | A1 | 9/2019 | Fillipova et al. |
| 2019/0287652 | A1 | 9/2019 | Gross |
| 2019/0316209 | A1 | 10/2019 | Hubbell et al. |
| 2020/0005901 | A1 | 1/2020 | Cohen et al. |
| 2020/0219587 | A1 | 7/2020 | Hubbell |
| 2020/0294624 | A1 | 9/2020 | Filippova et al. |
| 2020/0365229 | A1 | 11/2020 | Fields et al. |
| 2020/0372296 | A1 | 11/2020 | Maher |
| 2021/0324477 | A1 | 10/2021 | Xiang et al. |

FOREIGN PATENT DOCUMENTS

| | | |
|---|---|---|
| CN | 107430588 A | 12/2017 |
| CN | 108064314 B | 5/2018 |
| WO | 2010/037001 | 1/2010 |
| WO | 2010/051318 A2 | 5/2010 |
| WO | 2011/127136 | 10/2011 |
| WO | 2012/071621 A1 | 6/2012 |
| WO | 2013/052907 A1 | 4/2013 |
| WO | 2014/149134 A1 | 9/2014 |
| WO | 2016/094853 A1 | 6/2016 |
| WO | 2017062382 A1 | 4/2017 |
| WO | 2017/161175 A1 | 9/2017 |
| WO | 2017/181202 A1 | 10/2017 |
| WO | 2017/212428 A1 | 12/2017 |
| WO | 2018/009723 A1 | 1/2018 |
| WO | 2018/022890 A1 | 2/2018 |

(56) References Cited

FOREIGN PATENT DOCUMENTS

| WO | 2018/022906 A1 | 2/2018 |
|---|---|---|
| WO | 2018/031929 A1 | 2/2018 |
| WO | 2019/084559 A1 | 5/2019 |

OTHER PUBLICATIONS

"International Search Report and Written Opinion" for International Application No. PCT/US2019/034994, dated Sep. 13, 2019, 28 pages.
Alkan et al., 2009, Nat Genet 41:1061-7.
Benjamini and Speed, 2012, Nucleic Acids Research 40(10): e72.
Boeva et al., 2011, Bioinformatics 27(2), p. 268.
Casadio et al., 2013, "Urine cell-free DNA integrity as a marker for early bladder cancer diagnosis: preliminary data," Urol Oncol. 31(8):1744-1750.
Chan et al., 2003, "Clinical Sciences Reviews Committee of the Association of Clinical Biochemists Cell-free nucleic acids in plasma, serum and urine: a new tool in molecular diagnosis," Ann Clin Biochem. 40(Pt 2):122-130.
De Mattos-Arruda and Caldas, 2016, "Cell-free circulating tumour DNA as a liquid biopsy in breast cancer," Mol Oncol. 10(3):464-474.
Frenel et al., 2015, "Serial next-generation sequencing of circulating cell-free DNA evaluating tumor clone response to molecularly targeted drug administration," Clin Cancer Res. 21 (20):4586-4596.
Goessl et al., 2000, "Fluorescent methylation-specific polymerase chain reaction for DNA-based detection of prostate Cancer in bodily fluids," Cancer Res. 60(21):5941-5945.
Gold, 1996, "Softmax to Softassign: Neural Network Algorithms for Combinatorial Optimization," Journal of Artificial Neural Networks 2, 381-399.
Hao et al., 2014, "Circulating cell-free DNA in serum as a biomarkerfordiagnosis and prognostic prediction of colorectal cancer," Br J Cancer 111 (8):1482-1489.
Heitzer et al., 2013, "Establishment of tumorspecific copy number alterations from plasma DNA of patients with cancer," Int J Cancer. 133(2):346-356).
Heitzer et al., 2015, "Circulating tumor DNA as a liquid biopsy for cancer," Clin Chem. 61 (1):112-123.
Kim et al., 2014, "Circulating cell-free DNA as a promising biomarker in patients with gastric cancer: diagnostic validity and significant reduction of cfDNA after surgical resection," Ann Surg Treat Res 86(3):136-142.
Liu et al., 2019, "Bisulfite-free direct detection of 5-methylcytosine and 5-hydroxymethylcytosine at base resolution," Nature Biotechnology 37, pp. 424-429.
Lo et al., 2010, "Maternal plasma DNA sequencing reveals the genome-wide genetic and mutational profile of the fetus," Sci Transl Med. 2(61):61 ra91).
Miller et al., "ReadDepth: A Parallel R Package for Detecting Copy Number Alterations from Short Sequencing Reads", 2011, PLoS ONE 6(1), p. e16327.
Raptis and Menard, 1980, "Quantitation and characterization of plasma DNA in normals and patients with systemic lupus erythematosus," J Clin Invest. 66(6):1391-1399.
Salvi et al., 2016, "Cell-free DNA as a diagnostic marker for cancer: current insights," Onco Targets Ther. 9:6549-6559.
Shao et al., 2015 "Quantitative analysis of cell-free DNA in ovarian cancer," Oncol Lett 10(6):3478-3482).
Shapiro et al., 1983, "Determination of circulating DNA levels in patients with benign or malignant gastrointestinal disease," Cancer. 51 (11):2116-2120.
Siegel et al., 2015, "Cancer statistics," CA Cancer J Clin. 65(1):5-29.
Sozzi et al., "Quantification of free circulating DNA as a diagnostic marker in lung cancer," J Clin Oncol. 21 (21):3902-3908.
Stroun et al., 1989, "Neoplastic characteristics of the DNA found in the plasma of cancer patients," Oncology 46 (5):318-322.
Terry et al., 2016, "A prospective evaluation of early detection biomarkers for ovarian cancer in the European EPIC cohort," Clin Cancer Res. Apr. 8, 2016; Epub.
U.S. Appl. No. 62/827,682, entitled "Systems and Methods for Using Fragment Lengths as a Predictor of Cancer," filed Apr. 1, 2019.
U.S. Appl. No. 62/847,223, entitled "Model-Based Featurization and Classification," filed May 13, 2019.
U.S. Appl. No. 62/851,486, entitled "Systems and Methods for Determining Whether a Subject Has a Cancer Condition Using Transfer Learning," filed May 22, 2019.
Yoon et al., "Sensitive and Accurate Detection of Copy Number Variants Using Read Depth of Coverage", 2009, Genome Research 19(9): 1586.
Zhang et al., 2015, "Tumor markers CA 19-9, CA242 and CEA in the diagnosis of pancreatic cancer: a meta-analysis," Int J Clin Exp Med 8(7):11683-11691.
Zonta et al., 2015, "Assessment of DNA integrity, applications for cancer research," Adv Clin Chem 70:197-246.
International Search Report and Written Opinion for PCT Application No. PCT/US2019/22139, dated Jul. 11, 2019, 18 pages.
Patent Application, U.S. Appl. No. 62/818,013, filed Mar. 13, 2019.
Patent Application, U.S. Appl. No. 62/679,347, filed Jun. 1, 2018.
Erickson, et al., "Somatic gene mutation and human disease other than cancer," Mutat Res 543(2), pp. 125-136, 2003.
Erickson, "Somatic gene mutation and human disease other than cancer: An update," Mutat Res 705(2), pp. 96-106, 2010.
Hoadley, et al., "Multi-platform analysis of 12 cancer types reveals molecular classification within and across tissues-of-origin," Cell, 158(4), pp. 929-944, 2014.
Angermueller, Christof, et al., "DeepCpG: accurate prediction of single-cell DNA methylation states using deep learning," Genome Biology, 18(1), 13 pages, 2017.
Poplin, Ryan, et al., "A universal SNP and small-indel variant caller using deep neural networks," Nature Biotechnology, 36(10), 2018.
Agresti, "An Introduction to Categorical Data Analysis" Chapter 5, John Wiley & Son, New York, 103-144, 1996.
Boser, et al., "A training algorithm for optimal margin classifiers", Proceedings of the 5th Annual ACM Workshop on Computational Learning Theory, ACM Press, Pittsburgh, Pa., 142-152, 1992.
Breiman, 1999, "Random Forests-Random Features," Technical Report 567, Statistics Department, U.C. Berkeley, Sep. 1999.
Chen, et al., "Conflict of CpG density and DNA methylation are proximally and distally involved in gene regulation in human and mouse tissues", Epgenetics 13(7), 721-7 41, 2018.
Cook, "Use and Misuse of the Receiver Operating Characteristic Curve in Risk Prediction," Circulation 2007, 115: 928-935.
Du, et al., "Comparison of Beta-value and M-value methods for quantifying methylation levels by microarray analysis", BMC Bioinformatics 11, 587, 2010.
Duda, "Pattern Classification", Second Edition, John Wiley & Sons, Inc., 259, 262- 265, 537-563.
Duda and Hart, Pattern Classification and Scene Analysis, 1973, John Wiley & Sons, Inc., New York., 211-256.
Fabregat, et al., "The Reactome Pathway Knowledgebase", Nucleic Acids Res., 46, D649-D655,2018.
Furey et al., 2000, Bioinformatics 16, 906-914.
Clark et al., Analytical Validation of a Hybrid Capture-Based Next-Generation Sequencing Clinical Assay for Genomic Profiling of Cell-Free Circulating Tumor DNA, The Journal of Molecular Diagnostics, ELSEVIER, 2018, 17 pages.
Gunasegaran et al., Evolutionary Cross Validation, 2017 8th International Conference on Information Technology (ICIT). IEEE, 2017 89-95.
Kersaudy-Kerhoas, Micro-scale blood plasma separation: from acoustophoresis to egg-beaters, 2013, Lab on a Chip, RSC Publishing, 24 pages.
Minarik et al, Utilization of Benchtop Next Generation Sequencing Platforms Ion Torrent PGM and MiSeq in Noninvasive Prenatal Testing for Chromosome 21 Trisomy and Testing of Impact of In Silico and Physical Size Selection on Its Analytical Performance, 2015, 12 pages, PLoS ONE.

(56) References Cited

OTHER PUBLICATIONS

Odegaard et al., Validation of a Plasma-Based Comprehensive Cancer Genotyping Assay Utilizing Orthogonal Tissue- and Plasma-Based Methodologies, 2018, pp. 3539-3549, American Assocation for Cancer Research.

Robinson, Peter N. et al., Computational Exome and Genome Analysis. First edition. Boca Raton, FL: CRC Press, 2017, 575 pages.

Xia, Ligang et al., Statistical Analysis of Mutant Allele Frequency Level of Circulating Cell-Free DNA and Blood Cells in Healthy Individuals, Scientific Reports 7.1, 2017, 7526-7.

Furey, et al., "Support vector machine classification and validation of cancer tissue samples using microarray expression data", Bioinformatics 16, 906-914, 2000.

Hassoun, "Fundamentals of Artificial Neural Networks", Massachusetts Institute of Technology, 1995.

Hastie, The Elements of Statistical Learning, Springer, New York, 2001.

Jaccard, "Étude comparative de la distribution florale dans une portion des Alpes et des Jura", Bulletin de la Societe vaudoise des sciences naturelles, 37547-579, 1901.

Jaccard, "The Distribution of the flora in the alpine zone" New Phytologist, 11, 37-50, 1912.

Jenkinson, et al., "Potential energy landscapes identify the information-theoretic nature of the epigenome", Nat. Genet. 49(5), 719-729, 2017.

Jolliffe, 1986, Principal Component Analysis, Springer, New York.

Kanehisa, et al., KEGG: Kyoto Encyclopedia of Genes and Genomes, Nucleic Acids Res., 28(1), 27-30, 2000.

Kosuba note on the triangle inequality for the Jaccard distance arXiv.1612.02696.

Larochelle, et al., "Exploring strategies for training deep neural networks", J Mach Learn Res 10, 1-40, 2009.

Leek and Storey, 2007, PLoS Genet 3, pp. 1724-1735.

Levandowsky, et al., "Distance between sets", Nature 234(5), 34-35, 1971.

Li, et al., "Mapping short DNA sequencing reads and calling variants using mapping quality scores", Genome Research, 18, 1852-8, 2008.

Lipkus, "A proof of the triangle inequality for the Tanimoto distance", Journal of Mathematical Chemistry, 26 (1-3), 263-265, 1999.

Moulton, et al., "Maximally Consistent Sampling and the Jaccard Index of Probability Distributions", International Conference on Data Mining, Workshop on High Dimensional Data Mining, 2018.

Nuel, "Exact distribution of a pattern in a set of random sequences generated by a Markov source: applications to biological data", Algorithms for Molecular Biology 5(15), 2010.

O'Marcaigh and Jacobson, 1993, "Estimating the Predictive Value of a Diagnostic Test, How to Prevent Misleading or Confusing Results," Clin. Ped. 32(8): 485-491.

Oxnard, et al. "Simultaneous Multi-cancer Detection and Tissue of Origin (TOO) Localization Using Targeted Bisulfite Sequencing of Plasma Cell-free DNA (cfDNA)", American Society of Clinical Oncology (ASCO) Breakthrough, Oct. 11-13, 2019, Bangkok, Thailand, 2019.

Price et al., 2006, Nat Genet 38, pp. 904-909.

Pepe et al., 2004, "Limitations of the Odds Ratio in Gauging the Performance of a Diagnostic, Prognostic, or Screening Marker," Am. J. Epidemiol 159 (9): 882-890.

Qian, et al., "Intelligent Surveillance Systems", Springer, 161, 2011.

Rogers, et al., "A Computer Program for Classifying Plants", Science 132(3434), 1115-1118, 1960.

Simonyan, et al., "Very Deep Convolutional Networks for Large-Scale Image Recognition", 2014.

Swanton, et al., 2017, "Phylogenetic ctDNA analysis depicts early stage lung cancer evolution," Nature, 545(7655): 446-451.

Tan, et al., "Introduction to Data Mining", 2005.

Tanimoto, et al., "An Elementary Mathematical theory of Classification and Prediction", Internal IBM Technical Report, 1958.

Vapnik, "Statistical Learning Theory", Wiley, New York, 1998.

Vincent, et al., "Stacked denoising autoencoders: Learning useful representations in a deep network with a local denoising criterion", J Mach Learn Res, 11, 3371-3408, 2010.

Yang, et al., "DistAl: An Inter-pattern Distance-based Constructive Learning Algorithm", Intelligent Data Analysis, 3(1), 55-83, 1999.

Yoon et al., 2009, Genome Research 19(9): 1586.

Yu, et al., "GaussianCpG: a Gaussian model for detection of CpG island in human genome sequences", BMC Genomics 18(4), 392, 2017.

Zeiler, 2012 "ADADEL TA: an adaptive learning rate method," CoRR, vol. abs/1212.5701.

Zhang, et al., "A novel method to quantify local CpG methylation density by regional methylation elongation assay on microarray", BMC Genomics 9:59, 9 pages, 2008.

Zhao et al., 2015, Clinical Chemistry 61 (4), pp. 608-616.

International Search Report and Written Opinion, PCT Application No. PCT/US2020/064577, dated Mar. 9, 2021.

U.S. Appl. No. 16/352,602, entitled "Anomalous Fragment Detection and Classification," filed Mar. 13, 2019.

U.S. Appl. No. 16/352,739, entitled "Method and System for Selecting, Managing, and Analyzing Data of High Dimensionality," filed Mar. 13, 2019.

U.S. Appl. No. 16/352,739, entitled "Systems and Methods for Enriching for Cancer-Derived Fragments Using Fragment Size," filed Mar. 13, 2019.

U.S. Appl. No. 62/642,507, filed Mar. 13, 2018 and entitled "Identifying Copy Number Aberrations" (67 pages}.

United States Patent Publication No. 2014/0100121, filed as U.S. Appl. No. 13/801,748, filed Mar. 13, 2013.

U.S. Appl. No. 16/384, 784 entitled "Multi-Assay Prediction Model for Cancer Detection," filed Apr. 15, 2019.

Yuchen Yuan et al., "DeepGene: an advanced cancer type classifier based on deep learning and somatic point mutations", BMC Bioinfonmatics 2016, 17(Suppl 17):476, 14 pages.

Steven T. Kothen-Hill et al., "Deep Learning Mutation Prediction Enables Early Stage Lung Cancer Detection in Liquid Biopsy", ICLR 2018, 24 pages.

Laure Sorber et al., "A Comparison of Cell-Free DNA Isolation Kits: Isolation and Quantification of Cell-Free DNA in Plasma", The Journal of Molecular Diagnostics, vol. 19, No. 1, Jan. 2017, 7 pages.

Trevor Hastie et al., "Chapter 9: Additive Models, Trees, and Related Models", The Elements of Statistical Learning, Second Edition, Springer Science+Business Media, LLC, 2009, pp. 295-336.

Alan Agresti, "Building and Applying Logistic Regression Models", An Introduction to Categorical Data Analysis, Second Edition, 2009, pp. 137-172.

Leek et al., "Capturing Heterogeneity in Gene Expression Studies by Surrogate Variable Analysis," 2007, PLOS Genet 3, pp. 1724-1735.

Rumelhart et al., 1988, "Neurocomputing: Foundations of research," ch. Learning Representations by Back-propagating Errors, pp. 696-699, Cambridge, MA, USA: MIT Press.

U.S. Appl. No. 62/642,508, filed Mar. 13, 2018 and entitled Identifying Copy Number Aberrations.

Zeiler, 2012 "ADADELTA: an adaptive learning rate method," CoRR, vol. abs/212.5701.

Hudecova, et al. (2017). Non-invasive prenatal diagnosis of thalassemias using maternal plasma cell free DNA. Best Practice & Research Clinical Obstetrics & Gynaecology, 39, 63-73. (Year: 2017).

Smedley, et al. (2016). A Whole-Genome Analysis Framework for Effective Identification of Pathogenic Regulatory Variants in Mendelian Disease. American Journal of Human Genetics, 99(3), 595-606. (Year: 2016).

Ulz, et al. (2016). Inferring expressed genes by whole-genome sequencing of plasma DNA. Nature Genetics, 48(10), 1273-1278. (Year: 2016).

* cited by examiner

202

A computer system 100 for classifying a cancer condition, in a plurality of different cancer conditions, for a species is provided. The computer system comprises a graphical processing unit 103 having a graphical processing memory, a general processor 102, and a general memory 111 addressable by the general processing unit. The general memory stores at least one program for execution by the at least one general processor. There is obtained, for each respective training subject in a plurality of training subjects of the species: (i) a cancer condition 124 of the respective training subject and (ii) a genotypic data construct 126 for the respective training subject that includes genotypic information corresponding to locations of a reference genome of the species, thereby obtaining a plurality of genotypic data constructs.

204

Format each genotypic construct 126 in the plurality of genotypic data constructs into a corresponding vector set 130 comprising a corresponding one or more vectors 132, thereby creating a plurality of vector sets.

206

Provide the plurality of vector sets 130 to the graphical processing unit memory 103. The graphical processing memory comprises a network architecture 138 that includes a first convolutional neural network path 140 for sequentially receiving vector sets 130 in the plurality of vector sets, and a scorer 152. The output of each layer in the first convolutional neural network path other than a final layer in the first convolutional neural network path serves as input into another layer in the first convolutional neural network path. The first convolutional neural network path comprises a first convolutional layer and a second convolutional layer. The first convolutional layer includes at least a first filter 146 with an associated first filter weight 148. The second convolutional layer includes at least a second filter with an associated second filter weight.

208

Responsive to input of a respective vector 130 set in the plurality of vector sets into the network architecture 138, perform a procedure.

| id | label | masked | unmasked | correct |
|---|---|---|---|---|
| 4584 | 1 | 0.931667 | 0.440125 | True |
| 3103 | 1 | 0.995661 | 0.533402 | True |
| 418 | 1 | 0.105743 | 0.562183 | False |
| 3329 | 1 | 0.859393 | 0.424829 | True |
| 653 | 1 | 0.942838 | 0.509724 | True |
| 1325 | 1 | 0.589058 | 0.942529 | False |
| 1283 | 1 | 0.646163 | 0.996595 | False |
| 2891 | 0 | 0.413999 | 0.756553 | True |

Figure 17

All Inv.Can.-CNNscore, cdstg1d: Non-cancer (362) vs I (160), II (141), III (70), IV (93), Non-informative (34)

| condition | n | min | mean | median | max | stdev |
|---|---|---|---|---|---|---|
| I | 160 | 0.352 | 0.552 | 0.541 | 0.998 | 0.103 |
| II | 141 | 0.374 | 0.607 | 0.563 | 1 | 0.164 |
| III | 70 | 0.419 | 0.772 | 0.750 | 1 | 0.196 |
| IV | 93 | 0.217 | 0.838 | 0.92 | 1 | 0.189 |
| Non-cancer | 362 | 0.203 | 0.527 | 0.518 | 0.771 | 0.078 |
| Non-informative | 34 | 0.395 | 0.631 | 0.578 | 0.999 | 0.19 |

Figure 33

HOPEL-CNNscore, cdstg1ld: Non-cancer (362) vs I (24), II (14), III (17), IV (41), Non-informative (3)

| condition | n | min | mean | median | max | stdev |
|---|---|---|---|---|---|---|
| I | 24 | 0.431 | 0.648 | 0.596 | 0.998 | 0.179 |
| II | 14 | 0.462 | 0.722 | 0.701 | 1 | 0.187 |
| III | 17 | 0.523 | 0.9 | 0.971 | 1 | 0.16 |
| IV | 41 | 0.521 | 0.896 | 0.969 | 1 | 0.136 |
| Non-cancer | 362 | 0.293 | 0.527 | 0.518 | 0.771 | 0.078 |
| Non-informative | 3 | 0.484 | 0.703 | 0.64 | 0.985 | 0.256 |

Figure 35

HiSigCan-CNNscore, cdstg1ld: Non-cancer (362) vs I (38), II (49), III (39), IV (63), Non-informative (10)

| condition | n | min | mean | median | max | stdev |
|---|---|---|---|---|---|---|
| I | 38 | 0.431 | 0.607 | 0.572 | 0.998 | 0.157 |
| II | 49 | 0.374 | 0.688 | 0.674 | 1 | 0.203 |
| III | 39 | 0.512 | 0.821 | 0.947 | 1 | 0.188 |
| IV | 63 | 0.521 | 0.888 | 0.960 | 1 | 0.146 |
| Non-cancer | 362 | 0.293 | 0.527 | 0.518 | 0.771 | 0.078 |
| Non-informative | 10 | 0.417 | 0.658 | 0.611 | 0.985 | 0.208 |

Figure 37

Lung-CNNscore, cdstg11d: Non-cancer (362) vs I (12),
II (5), III (10), IV (19), Non-informative (1)

| condition | n | min | mean | median | max | stdev |
|---|---|---|---|---|---|---|
| I | 12 | 0.431 | 0.632 | 0.599 | 0.998 | 0.18 |
| II | 5 | 0.54 | 0.728 | 0.709 | 0.998 | 0.167 |
| III | 10 | 0.592 | 0.9 | 0.97 | 1 | 0.161 |
| IV | 19 | 0.521 | 0.894 | 0.992 | 1 | 0.156 |
| Non-cancer | 362 | 0.293 | 0.527 | 0.518 | 0.771 | 0.078 |
| Non-informative | 1 | 0.985 | 0.985 | 0.985 | 0.985 | NA |

Figure 39

HER2+; CNNscore, subjcat5: Stage III/IV (6) vs Non-cancer (362) (continued below)

| label | Spec | Sens | b95CI | cutpoint |
|---|---|---|---|---|
| alpha0 | 0.9475 | 0.6667 | -- | 0.6556 |
| Sn50Sp | 0.96 | 0.5 | 0.118-0.882 | 0.6611 |
| Sn50Sp | 0.98 | 0.5 | 0.118-0.882 | 0.7085 |
| Sn50Sp | 0.99 | 0.5 | 0.118-0.882 | 0.7299 |
| Sp050Sn | 1 | 0.5 | 0.019-0.908 | 0.6503 |
| Sp075Sn | 0.8287 | 0.75 | 0.456-0.961 | 0.6204 |

| notes |
|---|
| Stage III/IV (6) vs Non-cancer (362) |
| Stage III/IV (6) vs Non-cancer (362) |
| Stage III/IV (6) vs Non-cancer (362) |
| Stage III/IV (6) vs Non-cancer (362) |
| Stage III/IV (6) vs Non-cancer (362) |
| Stage III/IV (6) vs Non-cancer (362) |

CONVOLUTIONAL NEURAL NETWORK SYSTEMS AND METHODS FOR DATA CLASSIFICATION

CROSS REFERENCE TO RELATED APPLICATION(S)

This application is a continuation of and claims the benefit of priority to U.S. patent application Ser. No. 16/428,575, filed on May 31, 2019, which claims the benefit of priority to U.S. Provisional Patent Application No. 62/679,746, entitled "CONVOLUTIONAL NEURAL NETWORK SYSTEMS AND METHODS FOR DATA CLASSIFICATION," filed Jun. 1, 2018, all of which are incorporated herein by reference in their entireties.

TECHNICAL FIELD

This specification describes using convolutional neural networks to classify subjects for a cancer condition using genotypic information from such subjects.

BACKGROUND

The increasing knowledge of the molecular pathogenesis of cancer and the rapid development of next generation sequencing techniques are advancing the study of early molecular alterations involved in cancer development in body fluids. Specific genetic and epigenetic alterations associated with such cancer development are found in plasma, serum, and urine cell-free DNA (cfDNA). Such alterations could potentially be used as diagnostic biomarkers for several types of cancers. See Salvi et al., 2016, "Cell-free DNA as a diagnostic marker for cancer: current insights," Onco Targets Ther. 9:6549-6559.

With a total of 1,658,370 cases each year in the United States as of 2015, cancer represents a prominent worldwide public health problem. See, Siegel et al., 2015, "Cancer statistics," CA Cancer J Clin. 65(1):5-29. Screening programs and early diagnosis have an important impact in improving disease-free survival and reducing mortality in cancer patients. As noninvasive approaches for early diagnosis foster patient compliance, they can be included in screening programs.

Noninvasive serum-based biomarkers used in clinical practice include carcinoma antigen 125 (CA 125), carcinoembryonic antigen, carbohydrate antigen 19-9 (CA19-9), and prostate-specific antigen (PSA) for the detection of ovarian, colon, and prostate cancers, respectively. See, Terry et al., 2016, "A prospective evaluation of early detection biomarkers for ovarian cancer in the European EPIC cohort," Clin Cancer Res. 2016 Apr. 8; Epub and Zhang et al., 2015, "Tumor markers CA19-9, CA242 and CEA in the diagnosis of pancreatic cancer: a meta-analysis," Int J Clin Exp Med. 8(7):11683-11691.

These biomarkers generally have low specificity (high number of false-positive results). Thus, new noninvasive biomarkers are actively being sought. The increasing knowledge of the molecular pathogenesis of cancer and the rapid development of new molecular techniques such as next generation nucleic acid sequencing techniques is promoting the study of early molecular alterations in body fluids.

Cell-free DNA (cfDNA) can be found in serum, plasma, urine, and other body fluids (Chan et al., 2003, "Clinical Sciences Reviews Committee of the Association of Clinical Biochemists Cell-free nucleic acids in plasma, serum and urine: a new tool in molecular diagnosis," Ann Clin Biochem. 40(Pt 2):122-130) representing a "liquid biopsy," which is a circulating picture of a specific disease. See, De Mattos-Arruda and Caldas, 2016, "Cell-free circulating tumour DNA as a liquid biopsy in breast cancer," Mol Oncol. 10(3):464-474.

The existence of cfDNA was demonstrated by Mandel and Metais (Mandel and Metais), "P. Les acides nucleiques du plasma sanguin chez l' homme [The nucleic acids in blood plasma in humans]," Seances, 1948, Soc Biol Fil. 142(3-4):241-243). cfDNA originates from necrotic or apoptotic cells, and it is generally released by all types of cells. Stroun et al showed that specific cancer alterations could be found in the cfDNA of patients. See, Stroun et al., 1989, "Neoplastic characteristics of the DNA found in the plasma of cancer patients," Oncology 46(5):318-322). A number of following papers confirmed that cfDNA contains specific tumor-related alterations, such as mutations, methylation, and copy number variations (CNVs), thus confirming the existence of circulating tumor DNA (ctDNA). See, Goessl et al., 2000, "Fluorescent methylation-specific polymerase chain reaction for DNA-based detection of prostate cancer in bodily fluids," Cancer Res. 60(21):5941-5945 and Frenel et al., 2015, "Serial next-generation sequencing of circulating cell-free DNA evaluating tumor clone response to molecularly targeted drug administration," Clin Cancer Res. 21(20):4586-4596.

cfDNA in plasma or serum is well characterized, while urine cfDNA (ucfDNA) has been traditionally less characterized. However, recent studies demonstrated that ucfDNA could also be a promising source of biomarkers. See, Casadio et al., 2013, "Urine cell-free DNA integrity as a marker for early bladder cancer diagnosis: preliminary data," Urol Oncol. 31(8): 1744-1750.

In blood, apoptosis is a frequent event that determines the amount of cfDNA. In cancer patients, however, the amount of cfDNA seems to be also influenced by necrosis. See Hao et al., 2014, "Circulating cell-free DNA in serum as a biomarker for diagnosis and prognostic prediction of colorectal cancer," Br J Cancer 111(8):1482-1489 and Zonta et al., 2015, "Assessment of DNA integrity, applications for cancer research," Adv Clin Chem 70:197-246. Since apoptosis seems to be the main release mechanism, circulating cfDNA has a size distribution that reveals an enrichment in short fragments of about 167 bp, (see, Heitzer et al., 2015, "Circulating tumor DNA as a liquid biopsy for cancer," Clin Chem. 61(1):112-123 and Lo et al., 2010, "Maternal plasma DNA sequencing reveals the genome-wide genetic and mutational profile of the fetus," Sci Transl Med. 2(61):61ra91) corresponding to nucleosomes generated by apoptotic cells.

The amount of circulating cfDNA in serum and plasma seems to be significantly higher in patients with tumors than in healthy controls, especially in those with advanced-stage tumors than in early-stage tumors. See, Sozzi et al., 2003 "Quantification of free circulating DNA as a diagnostic marker in lung cancer," J Clin Oncol. 21(21):3902-3908, Kim et al., 2014, "Circulating cell-free DNA as a promising biomarker in patients with gastric cancer: diagnostic validity and significant reduction of cfDNA after surgical resection," Ann Surg Treat Res 86(3):136-142; and Shao et al., 2015 "Quantitative analysis of cell-free DNA in ovarian cancer," Oncol Lett 10(6):3478-3482). The variability of the amount of circulating cfDNA is higher in cancer patients than in healthy individuals, (Heitzer et al., 2013, "Establishment of tumor-specific copy number alterations from plasma DNA of patients with cancer," Int J Cancer. 133(2):346-356) and the amount of circulating cfDNA is influenced by several physiological and pathological conditions, including proinflammatory diseases. See, Raptis and Menard, 1980, "Quantitation and characterization of plasma DNA in normals and patients with systemic lupus erythematosus," J Clin Invest. 66(6):1391-1399, and Shapiro et al., 1983, "Determination of circulating DNA levels in patients with benign or malignant gastrointestinal disease," Cancer. 51(11):2116-2120.

Given the promise of circulating cfDNA, as well as other forms of genotypic data, as a diagnostic indicator, ways of processing such data in order to derive accurate classifiers for cancer diagnosis are needed in the art.

SUMMARY

The present disclosure addresses the shortcomings identified in the background by providing robust techniques for classifying a cancer condition for a species. The network architecture of the present disclosure learns parameters within convolutional layers of convolutional neural network paths that activate when they see some specific type of feature at some spatial position in the input. The initial weights of each filter in a convolutional layer are obtained by training the convolutional neural network against a training set. Accordingly, the operation of the network architecture yields more complex features than the features historically used to classify cancer conditions.

In one aspect, there is obtained, for each training subject in a plurality of training subjects of the species, a cancer condition and a genotypic data construct for the subject. Each data construct is formatted into a corresponding vector set comprising a plurality of vectors having a plurality of elements. The vector sets are provided to a network architecture comprising at least one convolutional neural network path. The output of each layer in the at least one convolutional neural network path serves as input into another layer in the at least one convolutional neural network path or input to a final scorer. The at least one convolutional neural network path includes convolutional layers that each have at least one filter comprising a set of filter weights. Responsive to input of a vector set into a convolutional neural network path, input values are provided to a convolutional layer in the convolutional neural network path. This causes the layer to feed intermediate values, computed as a function of: (i) the at least one set of filter weights associated with the layer and (ii) the plurality of input values, into another layer in the convolutional neural network path, and causes a final layer in the convolutional neural network path to feed values from the convolutional neural network path final layer into the scorer. Accordingly, scores are obtained from the scorer, each corresponding to a vector set and these scores are compared to the subject cancer conditions. This comparison is used to adjust the at least one set of filter weights of the architecture thereby training the architecture to classify for cancer condition.

One aspect of the present disclosure provides an approach in which a cancer condition (e.g., cancer type, cancer stage of a particular cancer type, etc.), in a plurality of different cancer conditions, for a species, is determined using a network architecture that includes at least one convolutional neural network path. First, the network architecture is trained. For this, there is obtained, for each respective training subject in a plurality of training subjects of a species: (i) a cancer condition of the respective training subject and (ii) a genotypic data construct for the respective training subject that includes genotypic information corresponding to locations of a reference genome of the species, thereby obtaining a plurality of genotypic data constructs.

Each genotypic data construct in the plurality of genotypic data constructs is formatted into a corresponding vector set comprising a corresponding one or more vectors, thereby creating a plurality of vector sets. Each vector set in the plurality of vector sets has the same number of vectors. The plurality of vector sets is provided to a network architecture (in some embodiments resident in a graphical processing unit memory) that includes a first convolutional neural network path for sequentially receiving vector sets in the plurality of vector sets, and a scorer. The output of each layer in the first convolutional neural network path other than a final layer in the convolutional neural network path serves as input into another layer in the first convolutional neural network path. The first convolutional neural network path comprises a first convolutional layer and a second convolutional layer. The first convolutional layer includes at least one first filter comprising a first set of filter weights. The second convolutional layer includes at least a second filter comprising a second set of filter weights. In some embodiments there are two filters each comprising its own set of filter weights associated with the first convolutional layer and two filters each comprising its own sets of filter weights associated with the second convolutional layer. Responsive to input of a respective vector set in the plurality of vector sets into the network architecture, a procedure is performed that comprises (a) inputting a first plurality of input values into the first convolutional layer as a first function of values in the respective vector set, (b) causing the first convolutional layer to feed a first plurality of intermediate values computed as a second function of: (i) the at least one first set of filter weights and (ii) the first plurality of input values, into another layer in the first convolutional neural network path, (c) causing the second convolutional layer to feed second intermediate values, as a third function of (i) the at least one second set of filter weights and (ii) input values received by the second convolutional layer from another layer in the first convolutional neural network path, and (d) causing a final layer in the first convolutional neural network path to feed a plurality of values from the final layer into the scorer. In this way, a plurality of scores is obtained from the scorer. Each score in the plurality of scores corresponds to the input of a vector set in the plurality of vector sets into the network architecture. A comparison of respective scores in the plurality of scores to the corresponding cancer condition of the corresponding training subject in the plurality of training subjects is used to adjust (train) the at least one first set of filters weights and the at least one second set of filter weights thereby training the network architecture to classify a cancer condition, in the plurality of cancer conditions. With the network architecture suitably trained in this fashion, it can be used to score test subjects for cancer condition based upon an input of a vector set formed from genotypic information obtained from a biological sample of the test subject. In some embodiments, the scorer includes a multinomial logistic regression cost layer that provides a k-dimensional score, where k is a positive integer that equals the number of possible cancer conditions that the network architecture can discriminate. In some embodiments, the network architecture includes a plurality of convolutional neural network paths, each with its own set of convolutional layers and sets of filters, where each such path is for the genomic information of a different chromosome, a different set of chromosomes, and/or a different type of genotypic information. For instance, in some embodiments, one convolutional neural network path processes genotypic information from white blood cells whereas another convolutional neural network path processes genotypic information from cells that have been deemed to not be white blood cells. Each of the convolutional neural network paths feeds values into the single scorer.

Other embodiments are directed to systems, portable consumer devices, and computer readable media associated with methods described herein.

As disclosed herein, any embodiment disclosed herein when applicable can be applied to any aspect.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A and 2B illustrate an example flowchart of a method for classifying a cancer condition, in a plurality of different cancer conditions, for a species in accordance with some embodiments of the present disclosure.

FIGS. 16 and 17 illustrate sample the model performance of a network architecture, using a genotypic data construct for respective training subjects that includes cell-free nucleic acid data in the form of single track bin counts representative of a number of sequence reads in sequencing information measured from cell-free nucleic acid in biological samples obtained from the training subjects that maps onto the different regions of the genome of the species represented by the respective bins, for the training subjects in the training set, is affected by masking contribution from white blood cells to bin count, on a training subject by training subject basis, in accordance with an embodiment of the present disclosure. In FIG. 16, black circles represent correct shifts and grey hollow circles represent incorrect shifts.

FIGS. 32 and 33 illustrate sample convolutional network architecture scores of the instant disclosure for invasive cancers, which are histologically confirmed invasive cancers, by cancer stage, in accordance with an embodiment of the present disclosure.

FIGS. 34 and 35 illustrate sample convolutional network architecture scores of the instant disclosure for cancer type classification for the high mortality cancers: hepatobiliary, ovarian, pancreatic, esophageal, lung (HOPEL) broken out by cancer stage, in accordance with an embodiment of the present disclosure.

FIGS. 36 and 37 illustrate sample convolutional network architecture scores of the instant disclosure for high signal cancers (HiSigCan), which are defined as single primary invasive cancer of: ER– breast, colorectal, lung, pancreatic, ovarian, hepatobiliary, gastric, head and neck, and esophageal cancer, broken out by cancer stage, in accordance with an embodiment of the present disclosure.

FIGS. 38 and 39 illustrate sample convolutional network architecture scores of the instant disclosure for lung cancer, broken out by cancer stage, in accordance with an embodiment of the present disclosure.

DETAILED DESCRIPTION

Figure 1A:
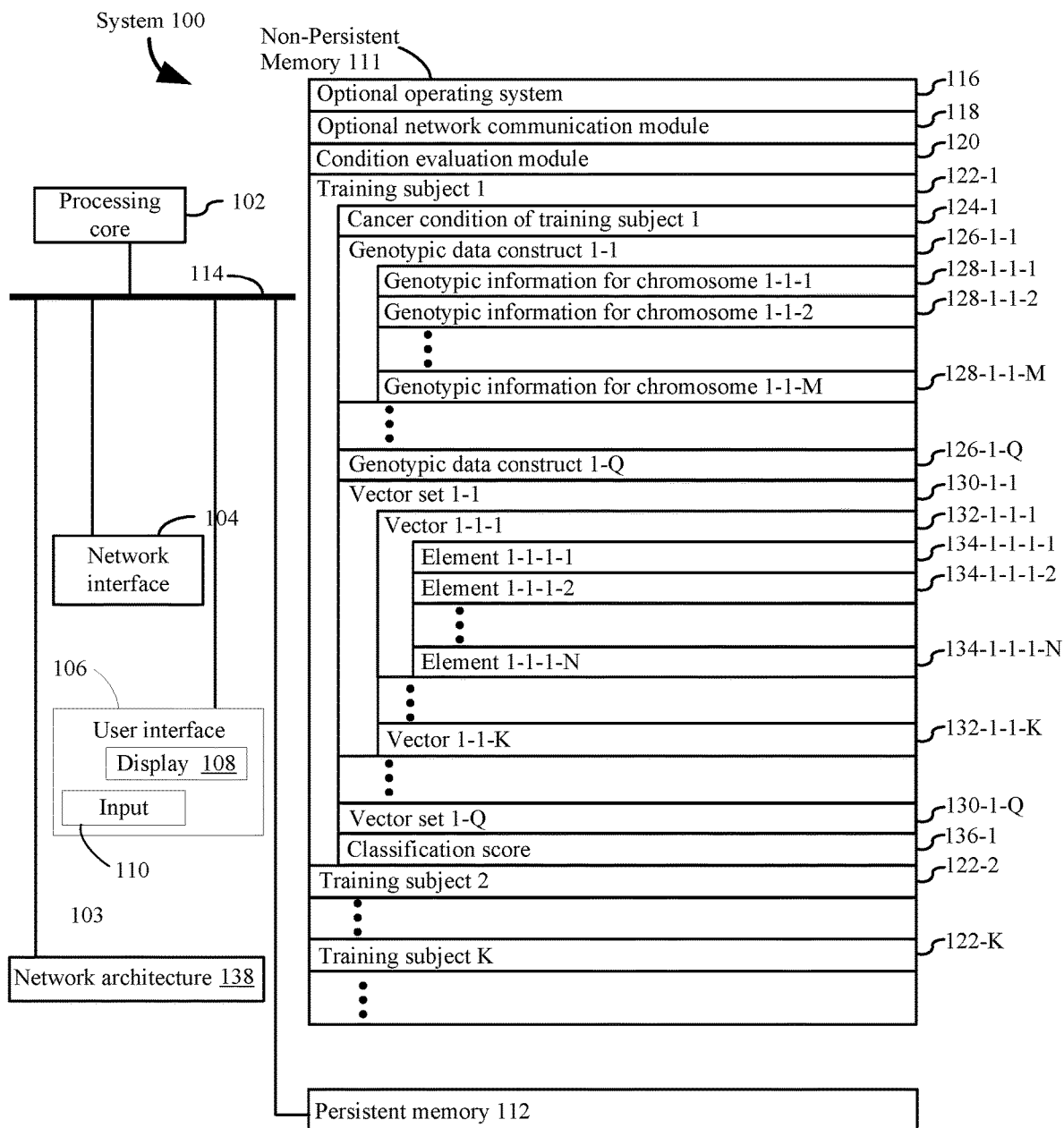
FIGS. 1A and 1B illustrate an example block diagram illustrating a computing device for classifying a cancer condition, in a plurality of different cancer conditions, for a species in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Systems and methods are provided for classifying a cancer condition (e.g., cancer type, cancer stage of a particular cancer type, etc.), in a plurality of different cancer conditions, for a species. There is obtained, for each respective training subject in a plurality of training subjects of the species: (i) a cancer condition of the respective training subject and (ii) a genotypic data construct for the respective training subject that includes genotypic information corresponding to locations of a reference genome of the species, thereby obtaining a plurality of genotypic data constructs.

Each genotypic data construct in the plurality of genotypic data constructs is formatted into a corresponding vector set comprising a corresponding one or more vectors, thereby creating a plurality of vector sets. Each vector set in the plurality of vector sets has the same number of vectors. In some embodiments, the vectors are one-dimensional. In some embodiments, the vectors are two-dimensional. In some embodiments, the vectors are each N-dimensional, where N is a positive integer. In one aspect, the vector set as disclosed herein enables conversion of genotypic data to visual data. For example, abundance levels of target nucleic acids in a biological sample (e.g., represented by numbers of sequence reads or numbers of nucleic acid fragments) are converted into visual data (e.g., dark grey representing high abundance level while light grey representing low abundance level). Differences in copy number signals can then be identified and "visualized" after the visual data are subject to methods of image data analysis such as various types of supervised or unsupervised machine learning analyses, including but not limited to full space learning, computer vision analysis, a convolutional neural network, a deep neural network, a shallow neural network, or fully connected neural networks.

For example, the plurality of vector sets is provided to a network architecture (in some embodiments resident in a graphical processing unit memory) that includes a first convolutional neural network path for sequentially receiving vector sets in the plurality of vector sets, and a scorer. The output of each layer in the first convolutional neural network path other than a final layer in the convolutional neural network path serves as input into another layer in the first convolutional neural network path.

The first convolutional neural network path comprises a first convolutional layer and a second convolutional layer. The first convolutional layer includes at least one first filter comprising a first set of filter weights. The second convolutional layer includes at least a second filter comprising a second set of filter weights.

Responsive to input of a respective vector set in the plurality of vector sets into the network architecture, a procedure is performed that comprises (a) inputting a first plurality of input values into the first convolutional layer as a first function of values in the respective vector set, (b) causing the first convolutional layer to feed a first plurality of intermediate values computed as a second function of: (i) at least the first set of filter weights and (ii) the first plurality of input values, into another layer in the first convolutional neural network path, (c) causing the second convolutional layer to feed second intermediate values, as a third function of (i) at least the second set of filter weights and (ii) input values received by the second convolutional layer from another layer in the first convolutional neural network path, and (d) causing a final layer in the first convolutional neural network path to feed a plurality of values from the final layer into the scorer.

In this way, a plurality of scores is obtained from the scorer. Each score in the plurality of scores corresponds to the input of a vector set in the plurality of vector sets into the network architecture.

A comparison of respective scores in the plurality of scores to the corresponding cancer condition of the corresponding training subject in the plurality of training subjects is used to adjust at least the first set of filter weights thereby training the network architecture to classify a cancer condition, in the plurality of cancer conditions.

Definitions

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As used herein, the term "biological sample," "patient sample," or "sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. In some embodiments, the biological sample consists of blood, whole blood, plasma, serum, urine, cerebrospinal fluid, fecal, saliva, sweat, tears, pleural fluid, pericardial fluid, or peritoneal fluid of the subject. In such embodiments, the biological sample is limited to blood, whole blood, plasma, serum, urine, cerebrospinal fluid, fecal, saliva, sweat, tears, pleural fluid, pericardial fluid, or peritoneal fluid of the subject and does not contain other components (e.g., solid tissues, etc.) of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis. A biological sample can be obtained from a subject invasively (e.g., surgical means) or non-invasively (e.g., a blood draw, a swab, or collection of a discharged sample).

As used herein the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein the term "classification" can refer to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the terms "cell-free nucleic acid," "cell-free DNA," and "cfDNA" interchangeably refer to nucleic acid fragments that are found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject (e.g., bloodstream). Cell-free nucleic acids are interchangeably referred to herein as "circulating nucleic acids." Examples of the cell-free nucleic acids include but are not limited to RNA, mitochondrial DNA, or genomic DNA. Cell-free nucleic acids can originate from one or more healthy cells and/or from one or more cancer cells.

As used herein, the term "false positive" (FP) refers to a subject that does not have a condition. False positive can refer to a subject that does not have a tumor, a cancer, a pre-cancerous condition (e.g., a precancerous lesion), a localized or a metastasized cancer, a non-malignant disease, or is otherwise healthy. The term false positive can refer to a subject that does not have a condition, but is identified as having the condition by an assay or method of the present disclosure.

As used herein, the term "fragment" is used interchangeably with "nucleic acid fragment" (e.g., a DNA fragment), and refers to a portion of a polynucleotide or polypeptide sequence that comprises at least three consecutive nucleotides. In the context of sequencing of nucleic cell-free nucleic acid fragments found in a biological sample, the terms "fragment" and "nucleic acid fragment" interchangeably refer to a cell-free nucleic acid molecule that is found in the biological sample. In such a context, the sequencing (e.g., whole genome sequencing, targeted sequencing, etc.) forms one or more copies of all or a portion of such a nucleic acid fragment in the form of one or more corresponding sequence reads. Such sequence reads, which in fact may be PCR duplicates of the original nucleic acid fragment, therefore "represent" or "support" the nucleic acid fragment. There may be a plurality of sequence reads that each represent or support a particular nucleic acid fragment in the biological sample (e.g., PCR duplicates). In some embodiments, nucleic acid fragments are cell-free nucleic acids.

As used herein, the term "false negative" (FN) refers to a subject that has a condition. False negative can refer to a subject that has a tumor, a cancer, a pre-cancerous condition (e.g., a precancerous lesion), a localized or a metastasized cancer, or a non-malignant disease. The term false negative can refer to a subject that has a condition, but is identified as not having the condition by an assay or method of the present disclosure.

As used herein, the phrase "healthy" refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "level of cancer" refers to whether cancer exists (e.g., presence or absence), a stage of a cancer, a size of tumor, presence or absence of metastasis, an estimated tumor fraction concentration, a total tumor mutational burden value, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a subject dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

As used herein a "methylome" can be a measure of an amount or extent of DNA methylation at a plurality of sites or loci in a genome. The methylome can correspond to all or a part of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

As used herein the term "methylation index" for each genomic site (e.g., a CpG site) can refer to the proportion of sequence reads showing methylation at the site over the total number of reads covering that site. The "methylation density" of a region can be the number of reads at sites within a region showing methylation divided by the total number of reads covering the sites in the region. The sites can have specific characteristics, (e.g., the sites can be CpG sites). The "CpG methylation density" of a region can be the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which can correspond to methylated cytosine) at CpG sites as a proportion of all CpG sites covered by sequence reads mapped to the 100-kb region. This analysis can also be performed for other bin sizes, e.g., 50-kb or 1-Mb, etc. A region can be an entire genome or a chromosome or part of a chromosome (e.g., a chromosomal arm). A methylation index of a CpG site can be the same as the methylation density for a region when the region only includes that CpG site. The "proportion of methylated cytosines" can refer the number of cytosine sites, "C's," that are shown to be methylated (for example unconverted after bisulfite conversion) over the total number of analyzed cytosine residues, e.g., including cytosines outside of the CpG context, in the region. The methylation index, methylation density and proportion of methylated cytosines are examples of "methylation levels." As disclosed herein, in some embodiments, methylation index can be used to characterize sequence reads or corresponding nucleic acid fragments as copy number signals (e.g., bin counts corresponding to different genomic regions).

As used herein, the term "methylation profile" (also called methylation status) can include information related to DNA methylation for a region. Information related to DNA methylation can include a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes can refer to the addition of a methyl group to position 5 of the heterocyclic ring of cytosine (e.g., to produce 5-methylcytosine) among CpG dinucleotides. Methylation of cytosine can occur in cytosines in other sequence contexts, for example 5'-CHG-3' and 5'-CHH-3', where H is adenine, cytosine or thymine. Cytosine methylation can also be in the form of 5-hydroxymethylcytosine. Methylation of DNA can include methylation of non-cytosine nucleotides, such as N6-methyladenine. For example, methylation data (e.g., density, distribution, pattern or level of methylation) from different genomic regions can be converted to one or more vector set and analyzed by methods and systems disclosed herein.

As used herein, the term "mutation," refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the "negative predictive value" or "NPV" can be calculated by TN/(TN+FN) or the true negative fraction of all negative test results. Negative predictive value can be inherently impacted by the prevalence of a condition in a population and pre-test probability of the population intended to be tested. The term "positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh and Jacobson, 1993, "Estimating The Predictive Value of a Diagnostic Test, How to Prevent Misleading or Confusing Results," Clin. Ped. 32(8): 485-491, which is entirely incorporated herein by reference.

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), and/or DNA analogs (e.g., containing base analogs, sugar analogs and/or a non-native backbone and the like), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. A nucleic acid may be prepared using a nucleic acid obtained from a subject as a template.

As used herein, a "plasma methylome" can be the methylome determined from plasma or serum of an animal (e.g., a human). A plasma methylome can be an example of a cell-free methylome since plasma and serum can include cell-free DNA. A plasma methylome can be an example of a mixed methylome since it can be a mixture of tumor/ patient methylome. A "cellular methylome" can be a methylome determined from cells (e.g., blood cells or tumor cells) of a subject, e.g., a patient. A methylome of blood cells can be called a blood cell methylome (or blood methylome).

As used herein, the term "ROC" or "ROC curve," refers to a receiver operator characteristic curve. A ROC curve can be a graphical representation of the performance of a binary classifier system. For any given method, a ROC curve can be generated by plotting the sensitivity against the specificity at various threshold settings. The sensitivity and specificity of a method for detecting the presence of a tumor in a subject can be determined at various concentrations of tumor-derived DNA in the plasma sample of the subject. Furthermore, provided at least one of three parameters (e.g., sensitivity, specificity, and the threshold setting), a ROC curve can determine the value or expected value for any unknown parameter. The unknown parameter can be determined using a curve fitted to a ROC curve. For example, provided the concentration of tumor-derived DNA in a sample, the expected sensitivity and/or specificity of a test can be determined. The term "AUC" or "ROC-AUC" can refer to the area under a receiver operator characteristic curve. This metric can provide a measure of diagnostic utility of a method, taking into account both the sensitivity and specificity of the method. A ROC-AUC can range from 0.5 to 1.0, where a value closer to 0.5 can indicate a method has limited diagnostic utility (e.g., lower sensitivity and/or specificity) and a value closer to 1.0 indicates the method has greater diagnostic utility (e.g., higher sensitivity and/or specificity). See, e.g., Pepe et al., 2004, "Limitations of the Odds Ratio in Gauging the Performance of a Diagnostic, Prognostic, or Screening Marker," Am. J. Epidemiol 159 (9): 882-890, which is entirely incorporated herein by reference. Additional approaches for characterizing diagnostic utility include using likelihood functions, odds ratios, information theory, predictive values, calibration (including goodness-of-fit), and reclassification measurements. Examples of the approaches are summarized, e.g., in Cook, "Use and Misuse of the Receiver Operating Characteristic Curve in Risk Prediction," Circulation 2007, 115: 928-935, which is entirely incorporated herein by reference.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein the term "sequencing breadth" refers to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

As used herein the terms "sequencing depth," "coverage" and "coverage rate" are used interchangeably herein to refer to the number of times a locus is covered by a consensus sequence read corresponding to a unique nucleic acid target molecule ("nucleic acid fragment") aligned to the locus; e.g., the sequencing depth is equal to the number of unique nucleic acid target fragments (excluding PCR sequencing duplicates) covering the locus. The locus can be as small as a nucleotide, or as large as a chromosome arm, or as large as an entire genome. Sequencing depth can be expressed as "YX", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "sensitivity" or "true positive rate" (TPR) refers to the number of true positives divided by the sum of the number of true positives and false negatives. Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. One parameter can be the percentage of DNA fragment of a particular size or range of sizes relative to all DNA fragments or relative to DNA fragments of another size or range.

As used herein, the term "specificity" or "true negative rate" (TNR) refers to the number of true negatives divided by the sum of the number of true negatives and false positives. Specificity can characterize the ability of an assay or method to correctly identify a proportion of the population that truly does not have a condition. For example, specificity can characterize the ability of a method to correctly identify the number of subjects within a population not having cancer. In another example, specificity can characterize the ability of a method to correctly identify one or more markers indicative of cancer.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, a subject is a male or female of any stage (e.g., a man, a women or a child).

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother versus fetus) or to healthy cells versus tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein, the term "true positive" (TP) refers to a subject having a condition. "True positive" can refer to a subject that has a tumor, a cancer, a pre-cancerous condition (e.g., a precancerous lesion), a localized or a metastasized cancer, or a non-malignant disease. "True positive" can refer to a subject having a condition, and is identified as having the condition by an assay or method of the present disclosure.

As used herein, the term "true negative" (TN) refers to a subject that does not have a condition or does not have a detectable condition. True negative can refer to a subject that does not have a disease or a detectable disease, such as a tumor, a cancer, a pre-cancerous condition (e.g., a precancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

As used herein, the term "vector" is an enumerated list of elements, such as an array of elements, where each element has an assigned meaning. As such, the term "vector" as used in the present disclosure is interchangeable with the term "tensor." As an example, if a vector comprises the bin counts for 10,000 bins, there exists a predetermined element in the vector for each one of the 10,000 bins. For ease of presentation, in some instances a vector may be described as being one-dimensional. However, the present disclosure is not so limited. A vector of any dimension may be used in the present disclosure provided that a description of what each element in the vector represents is defined (e.g., that element 1 represents bin count of bin 1 of a plurality of bins, etc.).

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1A. FIG. 1A is a block diagram illustrating a system 100 in accordance with some implementations. The device 100 in some implementations includes one or more processing units CPU(s) 102 (also referred to as processors), one or more graphical processing units 103, one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components.

The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices.

The persistent memory 112 optionally includes one or more storage devices remotely located from the CPU(s) 102. The persistent memory 112, and the non-volatile memory device(s) within the non-persistent memory 112, comprise non-transitory computer readable storage medium.

In some implementations, the non-persistent memory 111 or alternatively the non-transitory computer readable storage medium stores the following programs, modules and data structures, or a subset thereof, sometimes in conjunction with the persistent memory 112:
- an optional operating system 116, which includes procedures for handling various basic system services and for performing hardware dependent tasks;
- an optional network communication module (or instructions) 118 for connecting the system 100 with other devices, or a communication network;
- a condition evaluation module 120 for classifying a cancer condition of subjects; and
- information for each respective training subject 122 in a plurality of training subjects including (i) a cancer condition 124 of the respective training subject, (ii) at least one genotypic data construct 126 for the respective subject, and (iii) at least one vector set 130 for the respective subject.

In various embodiments, the genotypic data construct 126 includes genotypic information 128 for each respective chromosome in a plurality of chromosomes of a particular species (e.g., human).

In various embodiments, each vector set 130 comprises a corresponding plurality of vectors 132. Each such vector 134 has a plurality of elements 134. Each vector set 130 in the plurality of vector sets has the same number of vectors 132.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

In some embodiments, the system further comprises a graphical processing unit 103 having a memory that stores a network architecture 138 that includes at least one convolutional neural network path 140 for sequentially receiving vector sets in the plurality of vector sets, and a scorer 152. In some embodiments, the network architecture includes a layer that receives input values 144 and is associated with at least one filter 146 comprising a set of filter weights 148. This layer computes intermediate values 150 as a function of: (i) the set of filter weights and (ii) the plurality of input values. In some alternative embodiments, the network architecture 138 is stored in the non-persistent memory 111.

Although FIG. 1A depicts a "system 100," the figure is intended more as functional description of the various features that may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112.

While a system in accordance with the present disclosure has been disclosed with reference to FIG. 1A, methods in accordance with the present disclosure are now detailed.

Block 202. As discussed above in conjunction with FIG. 1A, the present disclosure details a computer system 100 for classifying a cancer condition, in a plurality of different cancer conditions, for a species. The computer system comprises an optional graphical processing unit 103 having a graphical processing memory, at least one general processor 102, and a general memory 111 addressable by the general processing unit. The general memory stores at least one program for execution by the at least one general processor (e.g., the condition evaluation module 120) and/or the optional graphical processing unit 103.

Using the computer system 100, there is obtained, for each respective training subject in a plurality of training subjects of the species: (i) a cancer condition 124 of the respective training subject and (ii) a genotypic data construct 126 for the respective training subject that includes genotypic information corresponding to locations of a reference genome of the species, thereby obtaining a plurality of genotypic data constructs. In some embodiments, the plurality of training subjects comprises 10 or more subjects, 100 or more subjects, 1000 or more subjects, 2000 or more subjects, 3000 or more subjects, 4000 or more subjects, 5000 or more subjects, 6000 or more subjects, 7000 or more subjects, 8000 or more subjects, 9000 or more subjects or 10000 or more subjects. In some embodiments, the plurality of training subjects include healthy subjects as well as subjects that have a cancer condition in the set of cancer conditions. In some embodiments, the plurality of training subjects include healthy subjects as well as representative subjects for each cancer condition in the set of cancer conditions. In some embodiments, the plurality of includes at least 50, 100, 150, 200, 250, 300, 350, 400, 450, 500, 550, 600, 650, 700, 750, 800, 850, 900, 950, 1000, 2000 or 3000 representative subjects for each cancer condition in the plurality of different cancer conditions as well as at least 50, 100, 150, 200, 250, 300, 350, 400, 450, 500, 550, 600, 650, 700, 750, 800, 850, 900, 950, 1000, 2000 or 3000 representative healthy (cancer free) subjects.

In some embodiments, the genotypic construct 126 for each respective training subject in the plurality of training subjects is obtained by whole genome sequencing or targeted panel sequencing of a biological sample from such reference training subjects. In some such embodiments, the sequencing is performed by whole genome sequencing and the average coverage rate of the plurality of sequence reads taken from a biological sample from a training subject is at least 1×, 2×, 3×, 4×, 5×, 6×, 7×, 8×, 9×, 10×, at least 20×, at least 30×, or at least 40× across the genome of the training subject.

In some embodiments, the biological sample is plasma. In some embodiments, the biological sample comprises blood, whole blood, plasma, serum, urine, cerebrospinal fluid, fecal, saliva, sweat, tears, pleural fluid, pericardial fluid, or peritoneal fluid of the training subject. In some embodiments, the biological sample consists of blood, whole blood, plasma, serum, urine, cerebrospinal fluid, fecal, saliva, sweat, tears, pleural fluid, pericardial fluid, or peritoneal fluid of the training subject.

In some embodiments, the biological sample is processed to extract cell-free nucleic acids in preparation for sequencing analysis. By way of a non-limiting example, in some embodiments, cell-free nucleic acid is extracted from a blood sample collected from a training subject in K2 EDTA tubes. Samples are processed within two hours of collection by double spinning of the blood first at ten minutes at 1000 g then plasma ten minutes at 2000 g. The plasma is then stored in 1 ml aliquots at −80° C. In this way, a suitable amount of plasma (e.g. 1-5 ml) is prepared from the biological sample for the purposes of cell-free nucleic acid extraction. In some such embodiments cell-free nucleic acid is extracted using the QIAamp Circulating Nucleic Acid kit (Qiagen) and eluted into DNA Suspension Buffer (Sigma). In some embodiments, the purified cell-free nucleic acid is stored at −20° C. until use. See, for example, Swanton, et al., 2017, "Phylogenetic ctDNA analysis depicts early stage lung cancer evolution," Nature, 545(7655): 446-451, which is hereby incorporated by reference. Other equivalent methods can be used to prepare cell-free nucleic acid from biological methods for the purpose of sequencing, and all such methods are within the scope of the present disclosure.

In some embodiments, the cell-free nucleic acid that is obtained from the first biological sample is in any form of nucleic acid defined in the present disclosure, or a combination thereof. For example, in some embodiments, the cell-free nucleic acid that is obtained from a biological sample is a mixture of RNA and DNA.

The time between obtaining a biological sample and performing an assay, such as a sequence assay, can be optimized to improve the sensitivity and/or specificity of the assay or method. In some embodiments, a biological sample can be obtained immediately before performing an assay. In some embodiments, a biological sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the training subject.

In some embodiments, the genotypic construct 126 for each respective training subject in the plurality of training subjects is obtained by targeted panel sequencing in which the sequence reads taken from a biological sample of a training subject in order to form the genotypic construct 126 have at least 50,000× coverage for this targeted panel of genes, at least 55,000× coverage for this targeted panel of genes, at least 60,000× coverage for this targeted panel of genes, or at least 70,000× coverage for this targeted panel of genes. In some such embodiments, the targeted panel of genes is between 450 and 500 genes. In some embodiments, the targeted panel of genes is within the range of 500±5 genes, within the range of 500±10 genes, or within the range 500±25 genes. In some such embodiments, the sequencing is performed by target sequencing and the average coverage rate of the plurality of sequence reads taken from a biological sample from a training subject is at least 40×, 100×, 200×, 300×, 400×, 500×, 1000×, 5000×, 10,000×, 20,000×, 30,000×, 40,000×, 50,000×, or 75,000× across the targeted regions.

In some embodiments, the genotypic construct 126 for each respective training subject in the plurality of training subjects is obtained by a whole genome sequencing assay. A whole genome sequencing assay refers to a physical assay that generates sequence reads for a whole genome or a substantial portion of the whole genome which can be used to determine large variations such as copy number variations or copy number aberrations. Such a physical assay may employ whole genome sequencing techniques or whole exome sequencing techniques.

In some embodiments, the genotypic construct 126 for each respective training subject in the plurality of training subjects is obtained by a methylation assay such as whole genome bisulfite sequencing. In some such embodiments, the whole genome bisulfite sequencing identifies one or more methylation state vectors in accordance with Example 1 below and as further disclosed in U.S. patent application Ser. No. 16/352,602, entitled "Anomalous Fragment Detection and Classification," filed Mar. 13, 2019, or in accordance with any of the techniques disclosed in U.S. Provisional Patent Application No. 62/847,223, entitled "Model-Based Featurization and Classification," filed May 13, 2019, each of which is hereby incorporated by reference. In some embodiments, the methylation sequencing makes use of any of the sequencing pathways disclosed in Liu et al, 2019, "Bisulfite-free direct detection of 5-methylcytosine and 5-hydroxymethylcytosine at base resolution," Nature Biotechnology 37, pp. 424-429, which is hereby incorporated by reference.

In some embodiments, sequence reads that are used for the formation of genotypic data constructs 126 are obtained in the manner described in the example assay protocol disclosed in Example 2.

In some embodiments, the sequencing data is pre-processed to correct biases or errors using one or more methods such as normalization, correction of GC biases, correction of biases due to PCR over-amplification, etc. For instance, in some embodiments, for a respective training subject, a median bin value across the corresponding plurality of bin values for the respective training subject is obtained. Then, each respective bin value in the plurality of bin values for the respective training subject is divided by this median value thus assuring that the bin values for the respective training subject are centered on a known value (e.g., on zero):

$$bv_i^* = \frac{bv_i}{\text{median}(bv_j)}$$

where, $bv_i$=the bin value of bin i in the plurality of bin values for the respective training subject, $bv_i^*$=the normalized bin value of bin i in the plurality of bin values for the respective training subject upon this first normalization, and median ($bv_j$)=the median bin value across the plurality of unnormalized bin values for the respective training subject. In some embodiments, the sequencing data is normalized as disclosed U.S. patent application Ser. No. 16/352,739, entitled "Method and System for Selecting, Managing, and Analyzing Data of High Dimensionality," filed Mar. 13, 2019, which is hereby incorporated by reference. In particular, in some embodiments, the sequencing data is normalized in accordance with equations 1 and 2 of the '739 application.

In some embodiments, rather than using the median bin value across the corresponding plurality of bin values, some other measure of central tendency is used, such as an arithmetic mean, weighted mean, midrange, midhinge, trimean, Winsorized mean, mean, or mode across the plurality of bin values of the respective training subject.

In some embodiments, each respective normalized bin count $bv_i^*$ is further normalized by the median normalized value for the respective bin across the plurality of training subjects k:

$$bv_i^{**} = \log\left(\frac{bv_i^*}{\text{median}(bv_{ik}^{**})}\right)$$

where, $bv_i^*$=the normalized bin value of bin i in the first plurality of bin values for the respective subject from the first normalization procedure described above, $bv_i^{**}$=the normalized bin value of bin i for the respective training subject upon this second normalization described here, and median($bv_{i\,k}^*$)=the median normalized bin value $bv_i^*$ for bin i across the plurality of training subjects (k subjects).

In some embodiments, the un-normalized bin values (counts) $bv_i$ are GC normalized. In some embodiments, the normalized bin values $bv_i^*$ are GC normalized. In some embodiments, the normalized bin values $bv_i^{**}$ are GC normalized. In such embodiments, GC counts of respective sequence reads in the plurality of sequence reads of each training subject in the plurality of training subjects are binned. A curve describing the conditional mean fragment count per GC value is estimated by such binning (Yoon et al., 2009, Genome Research 19(9):1586), or, alternatively, by assuming smoothness (Boeva et al., 2011, Bioinformatics 27(2), p. 268; Miller et al., 2011, PLoS ONE 6(1), p. e16327). The resulting GC curve determines a predicted count for each bin based on the bin's GC. These predictions can be used directly to normalize the original signal (e.g., $bv_i^*$, $bv_i$, or $bv_i^{}$). As a non-limiting example, in the case of binning and direct normalization, for each respective G+C percentage in the set {0%, 1%, 2%, 3%, . . . , 100%}, the value mGc, the median value of $bv_i^{}$ of all bins across the plurality of training subjects having this respective G+C percentage, is determined and subtracted from the normalized bin values $bv_i^{}$ of those bins having the respective G+C percentage to form GC normalized bin values $bv_i^{*}$.

In some embodiments, rather than using the median value of $bv_i^{}$ of all bins across the first plurality of subjects having this respective G+C percentage, some other form of measure of central tendency of $bv_i^{}$ of all bins across the plurality of training subjects having this respective G+C percentage is used, such as an arithmetic mean, weighted mean, midrange, midhinge, trimean, Winsorized mean, mean, or mode. In some embodiments, a correction curve is determined using a locally weighted scatterplot smoothing model (e.g., LOESS, LOWESS, etc.). See, for example, Benjamini and Speed, 2012, Nucleic Acids Research 40(10): e72; and Alkan et al., 2009, Nat Genet 41:1061-7. For example, in some embodiments, the GC bias curve is determined by LOESS regression of count by GC (e.g., using the 'loess' R package) on a random sampling (or exhaustive sampling) of bins from the plurality of training subjects. In some embodiments, the GC bias curve is determined by LOESS regression of count by GC (e.g., using the 'loess' R package), or some other form of curve fitting, on a random sampling of bins from a cohort of young healthy subjects that have been sequenced using the same sequencing techniques used to sequence the first plurality of subjects.

In some embodiments, the bin counts are normalized using principal component analysis (PCA) to remove higher-order artifacts for a population-based (healthies) correction. See, for example, Price et al., 2006, Nat Genet 38, pp. 904-909; Leek and Storey, 2007, PLoS Genet 3, pp. 1724-1735; and Zhao et al., 2015, Clinical Chemistry 61(4), pp. 608-616. Such normalization can be in addition to or instead of any of the above-identified normalization techniques. In some such embodiments, to train the PCA normalization, a data matrix comprising LOESS normalized bin counts $bv_i^{***}$ from young healthy subjects in the plurality of training subjects (or another cohort that was sequenced in the same manner as the plurality of training subjects) is used and the data matrix is transformed into principal component space thereby obtaining the top N number of principal components across the training set. In some embodiments, the top 2, the top 3, the top 4, the top 5, the top 6, the top 7, the top 8, the top 9 or the top 10 such principal components are used to build a linear regression model:

$$LM(PC_1, \ldots, PC_N)$$

Then, each bin $bv_i^{*}$ of each respective bin of each respective subject in the plurality of training subjects is fit to this linear model to form a corresponding PCA-normalized bin count $bv_i^{**}$:

$$bv_i^{**} = bv_i^{*} - \text{fit}_{LM(PC_1, \ldots, PC_N)}.$$

In other words, for each respective subject in the plurality of training subjects, a linear regression model is fit between its normalized bin counts {$bv_i^{*}$, . . . , $bv_i^{*}$} and the top principal components from the training set. The residuals of this model serve as final normalized bin values {$bv_i^{**}$, . . . , $bv_i^{}$} for the respective training subject. Intuitively, the top principal components represent noise commonly seen in healthy samples, and therefore removing such noise (in the form of the top principal components derived from the healthy cohort) from the bin values $bv_i^{*}$ can effectively improve normalization. See Zhao et al., 2015, Clinical Chemistry 61(4), pp. 608-616 for further disclosure on PCA normalization of sequence reads using a health population. Regarding the above normalization, it will be appreciated that all variables are standardized (e.g., by subtracting their means and dividing by their standard deviations) when necessary.

It will be appreciated that any form of representation of the number of nucleic sequence reads mapping to a given bin i can constitute a "bin value" and that such a bin value can be in un-normalized form (e.g., $bv_i$) or normalized form (e.g., $bv_i^*$, $bv_i^{}$, $bv_i^{*}$, $bv_i^{****}$, etc.).

Any form of sequencing can be used to obtain the sequence reads from the cell-free nucleic acid obtained from a biological sample of a training subject in order to form the genotypic construct 126 including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used to obtain sequence reads 140 from the cell-free nucleic acid obtained from the biological sample.

In some embodiments, sequencing-by-synthesis and reversible terminator-based sequencing (e.g., Illumina's Genome Analyzer; Genome Analyzer II; HISEQ 2000; HISEQ 2500 (Illumina, San Diego Calif.)) is used to obtain sequence reads from the cell-free nucleic acid obtained from a biological sample of a training subject in order to form the genotypic construct 126. In some such embodiments, millions of cell-free nucleic acid (e.g., DNA) fragments are sequenced in parallel. In one example of this type of sequencing technology, a flow cell is used that contains an optically transparent slide with eight individual lanes on the surfaces of which are bound oligonucleotide anchors (e.g., adaptor primers). A flow cell often is a solid support that is configured to retain and/or allow the orderly passage of reagent solutions over bound analytes. In some instances, flow cells are planar in shape, optically transparent, generally in the millimeter or sub-millimeter scale, and often have channels or lanes in which the analyte/reagent interaction occurs. In some embodiments, a cell-free nucleic acid sample can include a signal or tag that facilitates detection. In some such embodiments, the acquisition of sequence reads from the cell-free nucleic acid obtained from the biological sample includes obtaining quantification information of the signal or tag via a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

In some embodiments the species is human. In some embodiments, the species is mammalian. In some embodiments, the training set is mammalian, a reptile, avian, amphibian, fish, ungulate, ruminant, bovine, equine, caprine, ovine, swine, camelid, monkey, ape, ursid, poultry, dog, cat, mouse, rat, fish, dolphin, whale or shark.

In some embodiments, the plurality of cancer conditions is a plurality of cancer types comprising three or more cancer types selected from the group consisting of breast cancer, colorectal cancer, esophageal cancer, head/neck cancer, lung cancer, a lymphoma, ovarian cancer, pancreatic cancer, prostate cancer, renal cancer, and uterine cancer.

In some embodiments, the plurality of cancer conditions comprises is a plurality of cancer types comprising five or more cancer types selected from the group consisting of breast cancer, colorectal cancer, esophageal cancer, head/neck cancer, lung cancer, a lymphoma, ovarian cancer, pancreatic cancer, prostate cancer, renal cancer, and uterine cancer.

In some embodiments, the plurality of training subjects comprises twenty subjects, and for each respective cancer condition in the plurality of cancer conditions, the first plurality of training subjects includes at least two different subjects having the respective cancer condition.

In some embodiments, the plurality of training subjects comprises one hundred subjects, and for each respective cancer type in the plurality of cancer conditions, the first plurality of training subjects includes at least five different subjects having the respective cancer condition.

In some embodiments, each training subject is any living or non-living organism, including but not limited to a human (e.g., a male human, female human, fetus, pregnant female, child, or the like), a non-human animal, a plant, a bacterium, a fungus or a protist. In some embodiments, test subject is a mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, the test subject is a male or female of any stage (e.g., a man, a women or a child).

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

In some embodiments the species is human, and the genotypic data construct 126 for the respective training subject includes genotypic information for 22 autosomal chromosomes.

In some embodiments, the species is human, and the genotypic data construct 126 for the respective training subject includes genotypic information for less than 22 autosomal chromosomes.

Binning. In some embodiments, all or a portion of the genome of the species is represented by a plurality of bins. In such embodiments, each respective bin in the plurality of bins represents a different and non-overlapping region of the genome of a reference genome for the species.

In some embodiments, each such bin has the same size. In some embodiments, the bins can have different sizes. In some embodiments, a bin is defined by the number of nucleic acid residues within the bin. In some embodiments, a bin is defined by its location and the number of nucleic acids residues within the bin. Any suitable size can be used to define a bin. For example, a genomic region can include 10,000 bases or fewer, 20,000 bases or fewer, 30,000 bases or fewer, 40,000 bases or fewer, 50,000 bases or fewer, 60,000 bases or fewer, 70,000 bases or fewer, 80,000 bases or fewer, 90,000 bases or fewer, 100,000 bases or fewer, 110,000 bases or fewer, 120,000 bases or fewer, 130,000 bases or fewer, 140,000 bases or fewer, 150,000 bases or fewer, 160,000 bases or fewer, 170,000 bases or fewer, 180,000 bases or fewer, 190,000 bases or fewer, 200,000 bases or fewer, 220,000 bases or fewer, 250,000 bases or fewer, 270,000 bases or fewer, 300,000 bases or fewer, 350,000 bases or fewer, 400,000 bases or fewer, 500,000 bases or fewer, 600,000 bases or fewer, 700,000 bases or fewer, 800,000 bases or fewer, 900,000 bases or fewer, or 1,000,000 bases or fewer. In some embodiments, a genomic region can include more than 1,000,000 bases. In some embodiments, each bin represents a single contiguous region of a reference genome. In some embodiments, a bin represents two or more non-contiguous regions of a reference genome. As used herein, the genomic region of a bin will be referred to in the singular sense even in instances where the region represents two or more noncontiguous regions of the genome. In some embodiments each bin is the same size. In some embodiments, at least some of the bins are different sizes. In embodiments where the bins are different sizes the number of sequence reads in the sequencing data that map to the bin is represented as a sequence read density value (e.g., the total number of sequence reads divided by the size of the region represented by the bin) rather than a number of sequence reads mapping to the bin.

Further in some embodiments, the genotypic information for each respective training subject in the plurality of training subjects comprises a first bin count for each respective bin in the plurality of bins, each respective first bin count representative of first genotypic information that has been measured from a biological sample obtained from the respective training subject and that maps onto the different region of the reference genome corresponding to the respective bin. For instance, in some such embodiments, the species is human and the plurality of bins is between one thousand bins and fifty thousand bins.

Figure 25:
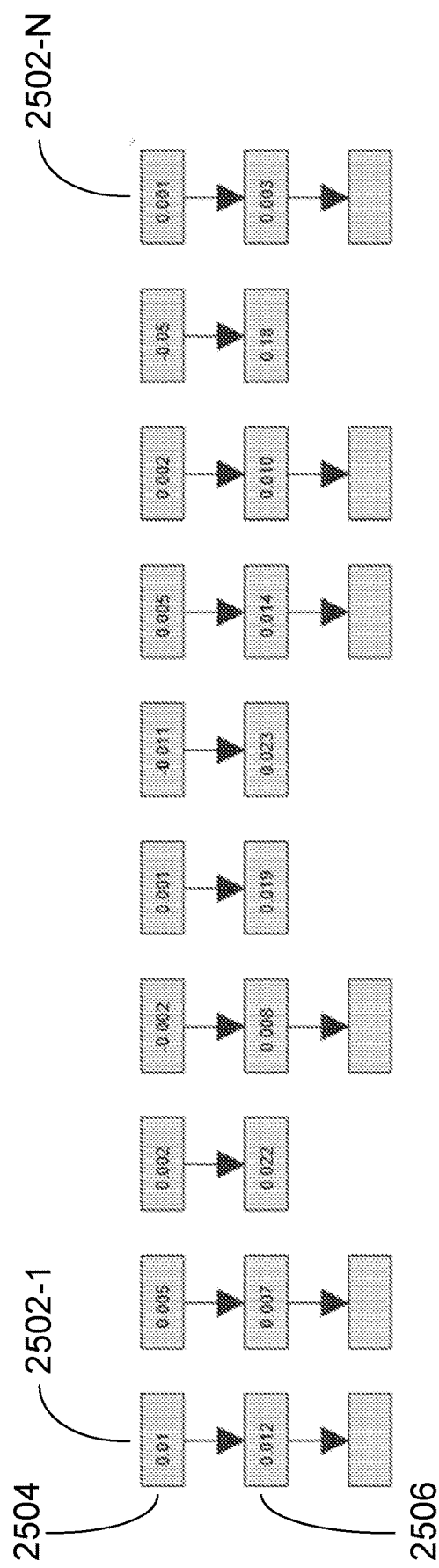
FIG. 25 illustrates a sample method for computing B-scores in accordance with an embodiment of the present disclosure.

In some embodiments, the first bin count representative of first genotypic information is a number of sequence reads in sequencing information measured from cell-free nucleic acid in the biological sample. The sequence reads map onto the region of the genome of the species represented by the respective bin. In some such embodiments, this first bin count is in the form of a bin count that is used to compute a B-score, which is described in U.S. patent application Ser. No. 16/352,739, entitled "Method and System for Selecting, Managing, and Analyzing Data of High Dimensionality," filed Mar. 13, 2019, which is hereby incorporated by reference. Referring to FIG. 25, in the B-score method, there is a unique nucleic acid fragment count 2502 for each bin 2504 in the plurality of bins. Each bin represents a region of the genome of the species. For example, in some embodiments, each bin uniquely represents 100 kilobases of the genome of the species. The sequence read count reflects the number of sequence reads obtained from the biological sample of each training subject in the plurality of training subjects through nucleic acid sequencing that map to the region of the reference genome represented by a respective bin. That is, such nucleic acid sequencing results in sequence reads that ultimately were obtained by using such nucleic acid fragments as template sequences in the sequencing. In some embodiments, the sequence read count for a bin is the number of sequence reads in sequencing data measured from cell-free nucleic acids in a biological sample from a subject that maps onto the region of the reference genome corresponding to the respective bin. In some such embodiments, a sequence read is said to map to the bin if the 5' end of the sequence falls within the region of the reference genome represented by the bin regardless of whether the 3' end of the sequence falls within the region of the reference genome represented by the bin. In some such embodiments, a sequence read is said to map to the bin if the 3' end of the sequence falls within the region of the reference genome represented by the bin regardless of whether the 5' end of the sequence falls within the region of the reference genome represented by the bin. In some such embodiments, a sequence read is said to map to the bin if both the 5' and the 3' end of the sequence falls within the region of the reference genome represented by the bin.

In some embodiments, such sequence read counts are pre-processed to correct biases or errors using one or more methods such as normalization and/or correction of GC or other forms of bias as described herein.

In some aspects, size-selected cell-free DNA (cfDNA) sequence reads are used. That is, only sequence reads of a particular size are used in some instance and the sequence reads that fail the size selection criteria are not counted (do not contribute to a corresponding bin count) or are given reduced weight relative to the sequence reads that satisfy the size selection criteria. The size selection can be achieved by either in vitro selection of cfDNA of a particular size range, i.e., prior to generating sequencing data, or in silico filtering of sequence read data. In some embodiments, the size selection criteria is based on the size of the sequence read itself (e.g., the number of nucleotides in the sequence read). In some embodiments, the size selection criteria is based on the size of the fragment that the sequence read represents (e.g., the number of nucleotides in the sequence read). Methods for size selecting nucleic acid fragments are known in the art, e.g., agarose electrophoresis. In some embodiments, the size selection occurs prior to library preparation, and in other embodiments after library preparation. In some embodiments, any of the size selection techniques disclosed in U.S. patent application Ser. No. 16/352,739, entitled "Systems and Methods for Enriching for Cancer-Derived Fragments Using Fragment Size," filed Mar. 13, 2019 are used.

In one embodiment, a ceiling cut-off value of less than 160 nucleotides is used, meaning that sequence reads must no greater than 160 nucleotides in length in order to contribute to the number of sequence reads in sequencing data measured from cell-free nucleic acids in the biological sample of a subject that maps onto the region of the reference genome corresponding to the respective bin. In some alternative embodiments, a maximum allowable sequence length of 150 nucleotides or less, 140 nucleotides or less, or 130 nucleotides is imposed on sequence reads. In some embodiments, sequence reads that fail this selection criterion do not contribute to the number of sequence reads mapping on to the region of the reference genome corresponding to a respective bin. In some embodiments, a maximum length of 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, or fewer nucleotides is imposed.

In some embodiments, the sequence reads are from whole genome sequencing, or targeted sequencing. As disclosed herein, sequencing can include but is not limited to nucleic acid sequencing (e.g., DNA, RNA, or hybrids or mixtures thereof), protein sequencing, sequence-based epigenetic analysis for analyzing protein-nucleic acid interactions (e.g., DNA or RNA methylation analysis, histone modification analysis, or combinations thereof), or protein-protein sequence modification analysis such as acetylation, methylation, ubiquitylation, phosphorylation, sumoylation, or combinations thereof.

Next, a data selection step is performed to select only a subset of bins. For instance, referring to FIG. 25, in some embodiments an interquartile range 2506 is computed for each respective bin 2502 in the plurality of bins using the sequence read count across the plurality of training subjects for the respective bin. Only the sequence read count of those bins that exhibit low variance are retained for use in the genotypic construct 126. Additional methods for bin selection are disclosed in U.S. patent application Ser. No. 16/352,739, entitled "Method and System for Selecting, Managing, and Analyzing Data of High Dimensionality," filed Mar. 13, 2019, which is hereby incorporated by reference. For example, a high variability filter can be created to allow one to discard bins corresponding to all genomic regions with bin count variations above a threshold value. In other embodiments, a low variability filter can be created to focus subsequent analysis on data with data variations below a threshold. As an illustration, a human haploid reference genome includes over three billion bases that can be divided into about 30,000 regions (or bins). If an experimental value is observed for each bin, for example, a total number of sequence reads that align to the particular region or bin, each subject can have over 30,000 measurements. After a low or high variability filter is applied, the number of bin measurements corresponding to a subject can be reduced by a significant portion. For example, including but not limited to about 50% or less, about 45% or less, about 40% or less, about 35% or less, about 30% or less, about 25% or less, 20% or less, 15% or less, 10% or less, or 5% or less bins (by removing bins that fail to satisfy the filter). In some embodiments, the number of bin measurements corresponding to a subject can be reduced by 50% or more such as about 55%, 60%, 65%, or 70% or more. For example, a subject that originally has over 30,000 corresponding bin measurements, can have over 30% fewer bin measurements (e.g., about 20,000) after a high or low variability filter is applied.

In some embodiments, the first bin count representative of first genotypic information is a number of sequence reads that map to a region corresponding to a particular bin in a reference genome of a species. In some embodiments, sequencing information measured from white blood cells is excluded from the bin count of the respective bin. In some embodiments, the first bin count of first genotypic information is a number of target nucleic fragments that map to the region corresponding to the particular bin.

In some embodiments, sequence reads mapping to the genomic region represented by a particular bin can be further divided into subgroups, resulting in an increased number of parameters in a vector or an increased number of dimensions in a vector for that subject. For example, one or more threshold values can be set to further characterize sequence reads corresponding to a particular bin. In some embodiments, the sequence reads for a particular bin can be separated into two or more groups each including sequence reads that have a length above or below a length threshold (e.g., 250 nucleotides or nt, 200 nt, 190 nt, 180 nt, 170 nt, 160 nt, 150 nt, 140 nt, 130 nt, 120 nt, 110 nt, 100 nt, 90 nt, 80 nt, 70 nt, 60 nt, or 50 nt). In some embodiments, sequence reads aligned to a particular bin can be separated into two or more groups each including sequence reads having a length above or below a length threshold (e.g., 250 nucleotides or nt, 200 nt, 190 nt, 180 nt, 170 nt, 160 nt, 150 nt, 140 nt, 130 nt, 120 nt, 110 nt, 100 nt, 90 nt, 80 nt, 70 nt, 60 nt, or 50 nt). In some embodiments, sequence reads for a particular bin can be separated into two or more numbers each representing sequence reads having a length in a particular range. Exemplary ranges include but are not limited to 10 to 250 nt, 20 to 240 nt, 30 to 230, In some embodiments, each bin includes a first measurement that is a number of sequence reads that are below a first length threshold (e.g., below a maximum length of 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125) and a second measurement that is a number of sequence reads falling in a range bounded by a second and third threshold value as disclosed in U.S. patent application Ser. No. 16/352,739, entitled "Method and System for Selecting, Managing, and Analyzing Data of High Dimensionality," filed Mar. 13, 2019, which is hereby incorporated by reference. In some embodiments, the second threshold length is from 240 nucleotides to 260 nucleotides and the third threshold length is from 290 nucleotides to 310 nucleotides. In some embodiments, the second threshold length is 250 nucleotides. In other embodiments, the second threshold length is 240, 241, 242, 243, 244, 245, 246, 247, 248, 249, 250, 251, 252, 253, 254, 255, 256, 257, 258, 259, or 260 nucleotides. In some embodiments, the third threshold length is 300 nucleotides (3028). In some embodiments, the third threshold length is 290, 291, 292, 293, 294, 295, 296, 297, 298, 299, 300, 301, 302, 303, 304, 305, 306, 307, 308, 309, or 310 nucleotides. In the embodiments disclosed herein, only those portions of a sequence read that map to the reference genome are included in the computation of the size (length) of the sequence read. In other words, any adaptors (e.g., unique molecule indicators, primer sequences) that may be present in a sequence read are not included in the determination of the length of the sequence read for purposes of imposing a sequence length threshold filter.

In some embodiments, the first bin count representative of first genotypic information is a number of sequence reads in sequencing data obtained using a methylation sequencing assay of cell-free nucleic acids in the biological sample that have a predetermined methylation state (e.g., one that is representative or indicative of a particular cancer condition) and that map onto a region of the reference genome corresponding to the respective bin. In some such embodiments, the methylation sequencing assay is whole genome bisulfite sequencing that identifies one or more methylation state vectors in accordance with Example 1 below and as further disclosed in U.S. patent application Ser. No. 16/352,602, entitled "Anomalous Fragment Detection and Classification," filed Mar. 13, 2019, or in accordance with any of the techniques disclosed in U.S. Provisional Patent Application No. 62/847,223, entitled "Model-Based Featurization and Classification," filed May 13, 2019, each of which is hereby incorporated by reference. In some such embodiments, a methylation state vector contributes to bin count when the methylation state vector is other than a wild type methylation state. In some such embodiments, the determination of whether a particular methylation state vector is other than a wild type methylation state is done by statistical comparison of the particular methylation state vector to a cancer free cohort population. Such a comparison may result in a p-value. In some such embodiments, a methylation state vector contributes to a bin count when the p-value associated the methylation state vector is 0.1 or less, 0.01 or less, or 0.001 or less, indicating that the chances that such a methylation state vector would be found in a cancer free subject is low.

In some embodiments, the first bin count representative of first genotypic information is a mean nucleic acid fragment length of the sequence reads in sequencing data measured from cell-free nucleic acids in the biological sample that map onto the region of the reference genome corresponding to the respective bin.

In some embodiments, the first bin count representative of first genotypic information is an allelic ratio of sequence reads measured from cell-free nucleic acid in the biological sample mapping onto the region of the reference genome corresponding to the respective bin.

In some embodiments, the first bin count representative of first genotypic information is a number of mutations identified in sequence reads measured from cell-free nucleic acid in the biological sample mapping onto the region of the reference genome corresponding to the respective bin.

In some embodiments, the genotypic information for each respective training subject in the plurality of training subjects comprises a set of dimension reduction component values that are obtained by using the number of sequence reads in sequencing data measured from cell-free nucleic acids mapping onto the region of the reference genome corresponding to the respective bins across the plurality of training subjects. Representative techniques for calculating such dimension reduction components are disclosed in U.S. Provisional Patent Application No. 62/851,486, entitled "Systems and Methods for Determining Whether a Subject Has a Cancer Condition Using Transfer Learning," filed May 22, 2019, as well as U.S. patent application Ser. No. 16/352,739, entitled "Method and System for Selecting, Managing, and Analyzing Data of High Dimensionality," filed Mar. 13, 2019, each of which is hereby incorporated by reference. For example, in some embodiments the counts of sequence reads associated with the 10,000 to 30,000 bins of a training subject can be reduced to 1,000 parameters or fewer, 500 parameters or fewer, 200 parameters or fewer, 100 parameters or fewer, 90 parameters or fewer, 80 parameters or fewer, 70 parameters or fewer, 60 parameters or fewer, 50 parameters or fewer, 40 parameters or fewer, 30 parameters or fewer, 20 parameters or fewer, 10 parameters or fewer, 8 parameters or fewer, 5 parameters or fewer, 4 parameters or fewer, 3 parameters or fewer, 2 parameters or fewer, or a single parameter, where such parameters are interchangeably referred to as dimension reduction components.

In some embodiments, one or more supervised learning algorithms can be used to discover such parameters. As disclosed herein, supervised learning problems can be separated into classification and regression problems. As disclosed herein, a classification problem is when the output variable is a category, such as "red" or "blue" or "disease" and "no disease." A regression problem is when the output variable is a real value, such as "dollars" or "weight." Either approach can be adapted to identify parameters. Example learning algorithms include but are not limited to support vector machines (SVM), linear regression, logistic regression, naive Bayes, decision trees algorithm, linear discriminant analysis, discriminant analysis, nearest neighbor analysis (kNN), feature point based approaches, neural networks analysis (multilayer perceptron), principal component analysis (PCA), linear discriminant analysis (LDA), and etc.

In some embodiments, one or more unsupervised learning algorithms can be used to discover such parameters. For example, unsupervised learning problems can be further grouped into clustering and association problems. A clustering problem is where you want to discover the inherent groupings in the data, such as grouping customers by purchasing behavior. An association rule learning problem is where you want to discover rules that describe large portions of your data, such as people that buy X also tend to buy Y. Example unsupervised learning algorithms include but are not limited to a clustering algorithm such as hierarchical clustering, k-Means clustering, Gaussian mixture models, self-organizing maps and Hidden Markov models, an algorithm for anomaly detection, a neural network based algorithm such as autoencoders, deep beliefs nets, Hebbian learning, generative adversarial networks, an algorithm for learning latent variable models such as expectation-maximization algorithm (EM), method of moments, blind signal separation techniques (e.g., principal component analysis (PCA), independent component analysis, non-negative matrix factorization, singular value decomposition, and etc.

In some embodiments, a semi-supervised machine learning algorithm can be used to identify parameters; for example, using any combinations of the algorithms enumerated herein or known in the art.

In some embodiments, one or more parameters are determined using the genotypic constructs of the plurality of training subject, either with or without data dimensionality reduction. In embodiments where dimension reduction components (parameters) are determined, the value of each dimension reduction component computed for a respective subject using that subjects genotypic data is placed in a corresponding element in the corresponding vector set for that subject.

Figure 26:
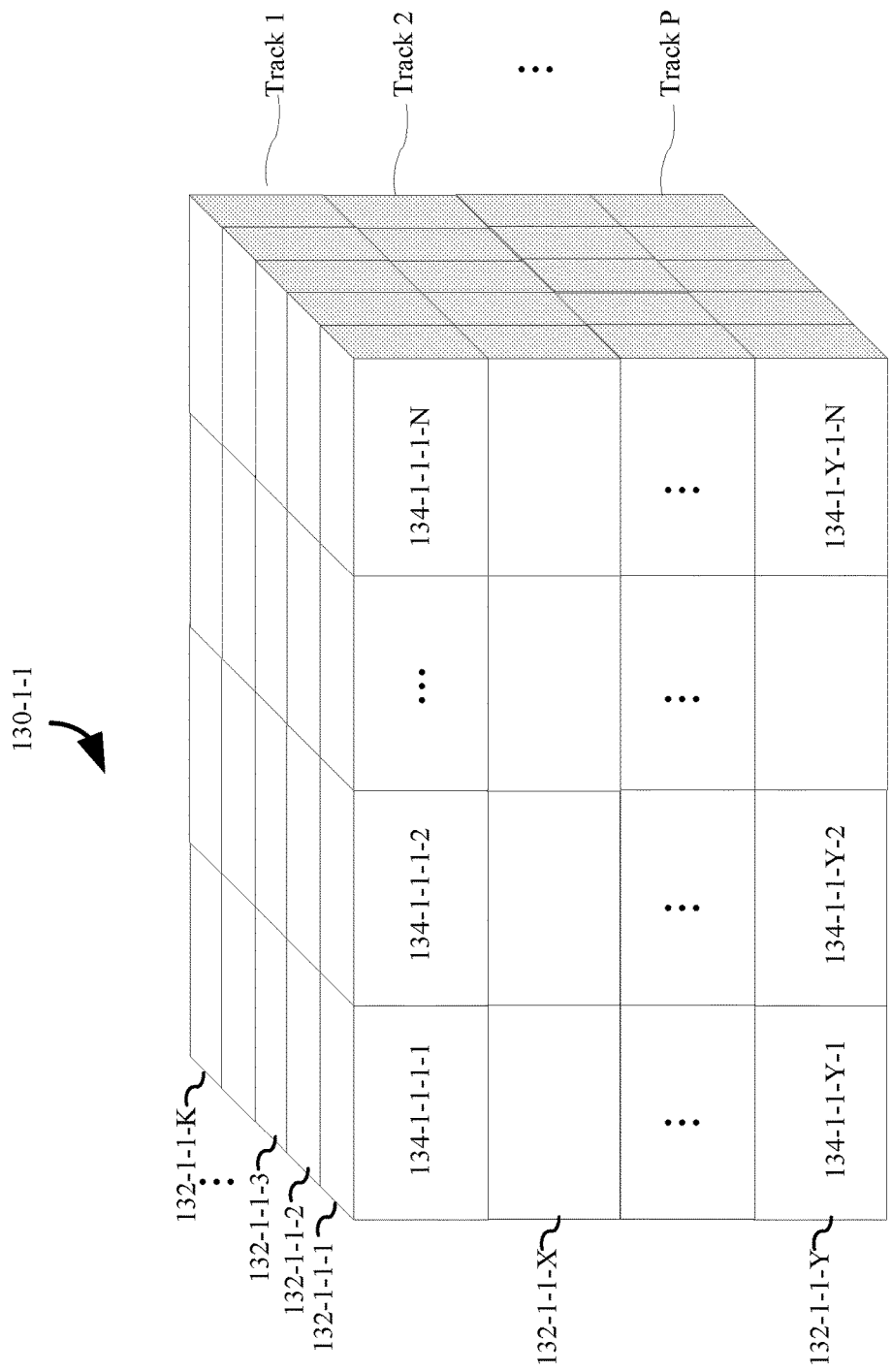
FIG. 26 illustrates a sample vector set in accordance with an embodiment of the present disclosure.

Block 204. Referring to block 204 of FIG. 2A, and as further illustrated in FIG. 26, each genotypic construct 126 in one or more genotypic data constructs for a training subject is formatted into a corresponding vector set 130 comprising a corresponding one or more vectors 132, thereby creating a plurality of vector sets. In some embodiments, each vector 132 in each vector set 130 has a plurality of elements 134. In some embodiments, each vector set 130 in the plurality of vector sets has the same number of vectors. In some embodiments, each vector 132 in each vector set 130 represents a different chromosome in the reference genome yet has the same number of elements. In some such embodiments, vectors 132 are padded so that they have the same number of elements. In the case of one-dimensional vectors they are padded so that they have the same length. In some embodiments, each vector 132 in each vector set 130 represents a plurality of chromosomes in the reference genome yet has the same number of elements. In some embodiments, the species is human and each vector 132 in each vector set 130 represents a different autosomal chromosome in the reference genome. In some embodiments, the vector set consists of only a single vector, the species is human, and the vector 132 in the vector set 130 represents all the autosomal chromosome in the human reference genome. In some embodiments, the vector set consists of twenty-two one-dimensional vectors, the species is human, and each vector 132 in the vector set 130 represents a different autosomal chromosome in the human reference genome.

Block 206. Referring to block 206 of FIG. 2A, the plurality of vector sets 130 are provided to the graphical processing unit memory 103 in some embodiments. The graphical processing memory 103 comprises a network architecture 138 that includes a convolutional neural network path 140 for sequentially receiving vector sets 130 in the plurality of vector sets, and a scorer 152. In some alternative embodiments the network architecture 138 is in non-persistent memory 111 rather than graphical processing memory 103.

Figure 2B:
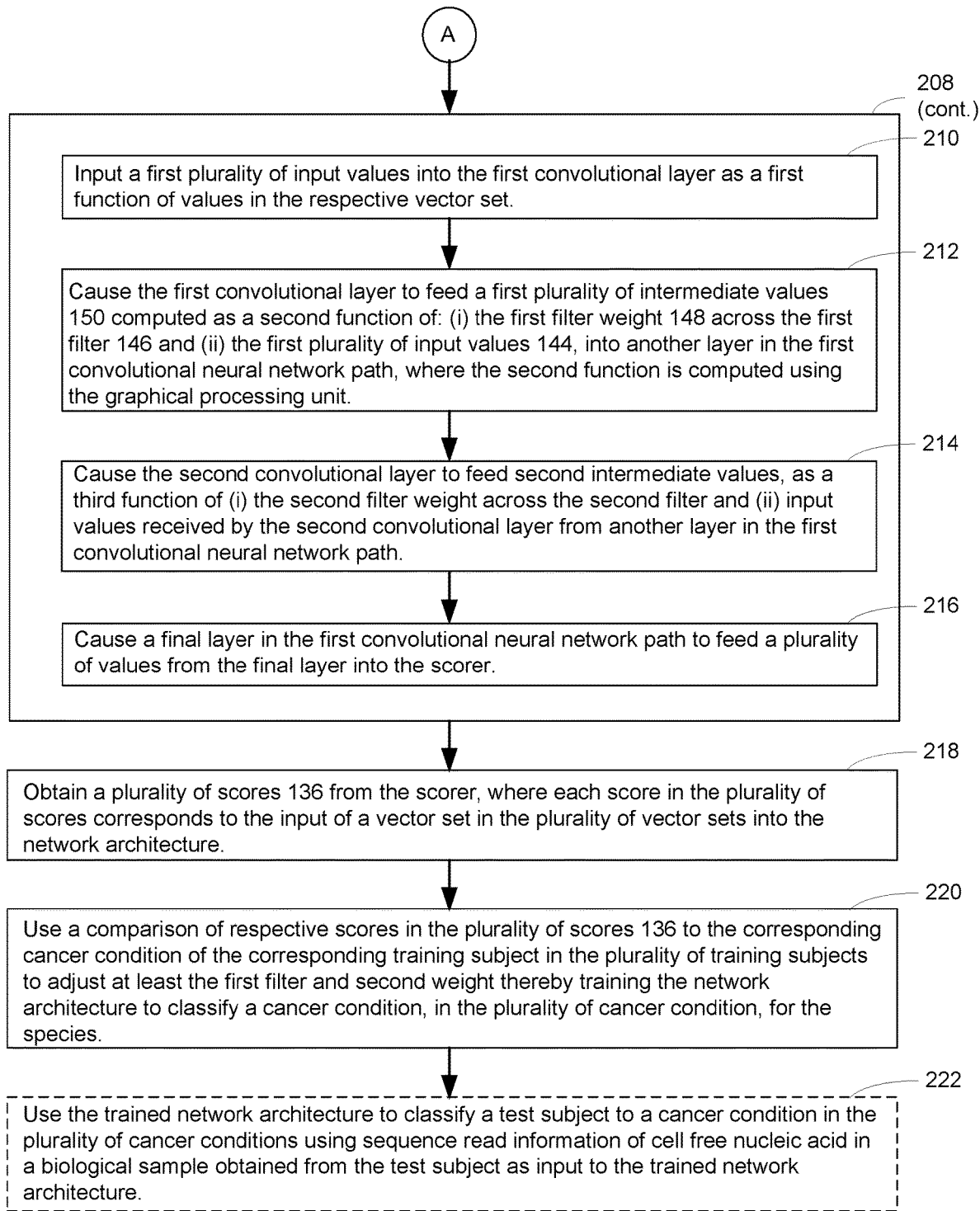

Blocks 208-216. Referring to block 208 of FIG. 2A, and using FIG. 3 to illustrate, responsive to input of a respective vector 130 set in the plurality of vector sets into the network architecture 138, a procedure illustrated as blocks 210 through 216 of FIG. 2B is performed. In block 210 the procedure inputs values into the first convolutional layer (e.g., layer 302-1 of FIG. 3) as a first function of values in the respective vector set.

In block 212, the procedure causes the first convolutional layer 302 to feed a first plurality of intermediate values 150 computed as a second function of: (i) at least the first set of filter weights 148 and (ii) the first plurality of input values 144, into another layer in the first convolutional neural network path. In some embodiments, the second function is computed using the graphical processing unit 103.

Figure 3:
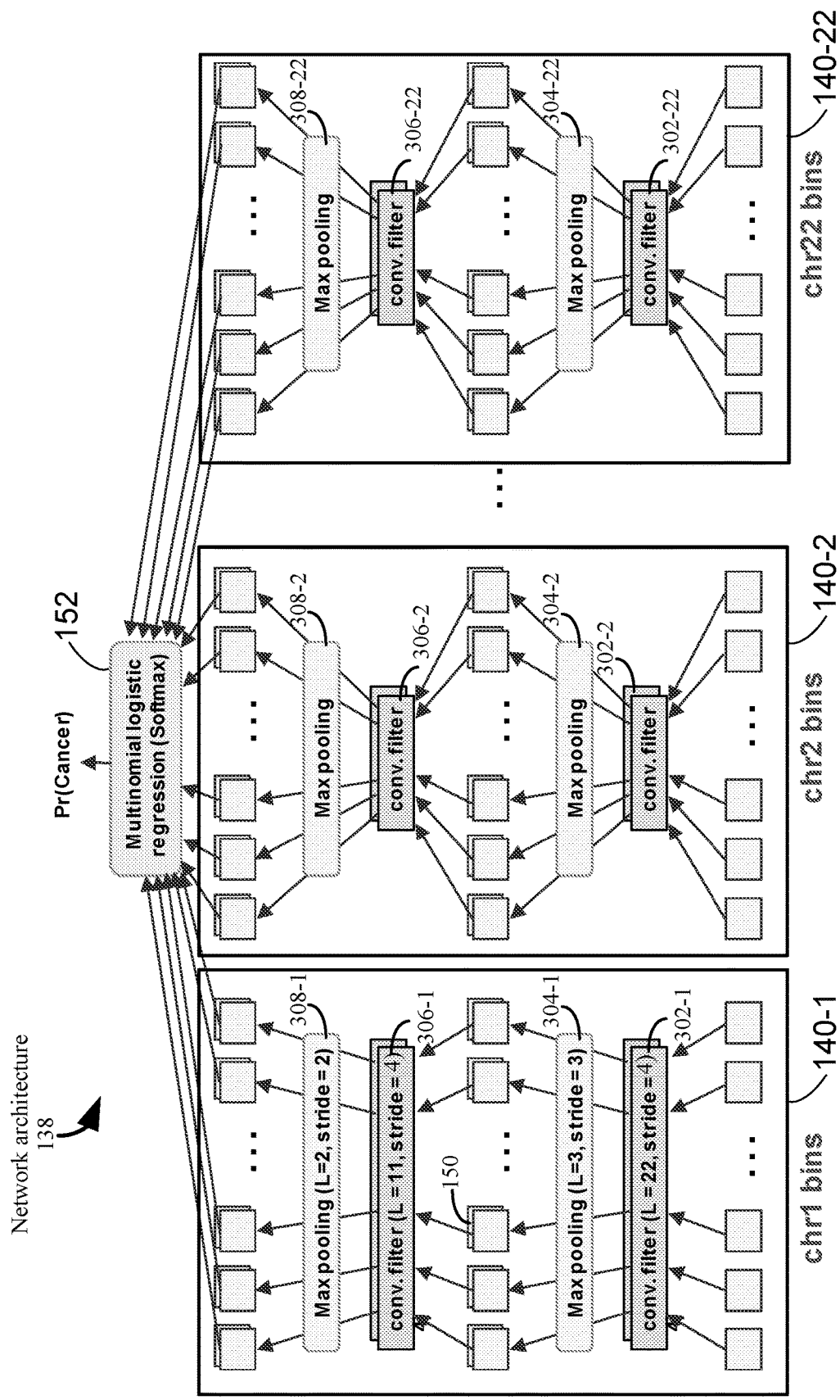
FIG. 3 illustrates an example network architecture 138 for classifying a cancer condition, in a plurality of different cancer conditions, for a species in accordance with some embodiments of the present disclosure.

Referring to FIG. 3, in some embodiments there are two filters associated with the first convolutional layer 302, each including a set of filter weights. In some such embodiments, the procedure causes the first convolutional layer 302 to feed intermediate values 150 computed as a second function (e.g., dot product) of: (i) the set of filter weights of the first filter associated with the first convolutional layer and (ii) the first plurality of input values 144 as well as a second function of: (i) the set of filter weights of the second filter associated with the first convolutional layer and (ii) the first plurality of input values 144 into another layer in the first convolutional neural network path. In some embodiments, the two filters associated with the first convolutional layer 302 are each normalized to different random values (e.g., Gaussian noise) and what is sought is convergence of the sets of filter weights as the network architecture 138 is trained. For instance, in some embodiments there are 24,000 bins fed into the first convolutional layer 302 and each of the two filters have sets of filter weights that are of length 22 (and thus have 22 weights and compute 22 independent dot products) as they each independently convolve across the first convolutional layer 302. In some embodiments the stride for these two filters is 2, 3, 4, 5, 6, 7, 8, 9, or 10.

In some embodiments, the first convolutional neural network path 140 comprises a first pooling layer (e.g., layer 304 of FIG. 3) and a second pooling layer (e.g., layer 308 of FIG. 3). Further, the procedure also comprises causing the first pooling layer to feed a third plurality of intermediate values 150 computed as a first pooling function of the first plurality of intermediate values from the first convolutional layer into another layer in the first convolutional neural network path, and causing the second pooling layer to feed a fourth plurality of intermediate values computed as a second pooling function of the second plurality of intermediate values from the second convolutional layer into another layer in the first convolutional neural network path or into the scorer.

In some embodiments there are 24,000 bins fed into the first convolutional layer 302, two filters each having a set of filter weights of length 22 (meaning that each set of filters has 22 weights) are each independently convolved across the first convolutional layer 302 with a stride of 4. In some embodiments, the activation layer produced by these two filters is then passed into the pooling layer 304 which pools with length 3, stride 3, resulting in an output from layer 304 of 555×2×22. Referring to block 214, and as illustrated in FIG. 3, the procedure causes the second convolutional layer 306 receives as input the output from pooling layer 304. In some embodiments, the second convolutional layer 306 also includes two filters, each including a set of weights that are randomized prior to network architecture 138 training. In some embodiments, the sets of filter weights in the two filters associated with the second convolutional layer are each of length 11 (meaning that each set of filter weights consists of 11 weights) and are each convolved against the input to the second convolutional layer 306 with a stride of 4. Referring to block 216, the procedure causes a final layer in the first convolutional neural network path 140 to feed a plurality of values from the final layer into the scorer 152. For instance, in some embodiments, the activation layer produced by the two filters of the second convolutional layer are passed into the pooling layer 308 which pools with length 2, stride 2, resulting in an output from layer 308 of 29×2×22, which is fed into the scorer 152.

In some embodiments, the first pooling layer 304 and the second pooling layer 308 are each independently selected from the group consisting of: a maxpooling layer, an average pooling layer, and an L2-norm pooling layer. In some embodiments the first pooling layer 304 and the second pooling layer 308 are each independently selected from the group consisting of: a maxpooling layer, an average pooling layer, and an L2-norm pooling layer.

The output of each layer 142 in the first convolutional neural network path 140 other than a final layer in the first convolutional neural network path 140 serves as input into another layer in the first convolutional neural network path. The first convolutional neural network path comprises a first convolutional layer and a second convolutional layer. The first convolutional layer includes at least a first filter 146 comprising a first set of weights 148. The second convolutional layer includes at a second filter comprising a second set of weights.

Referring to FIG. 3, in some embodiments, the set of filter weights in the first filter that is associated with the first convolutional layer 302 has a fixed one-dimensional size that is convolved (stepped at a predetermined step rate, stride) across the length of the one dimensional vectors 132 inputted into the first convolutional layer 302, computing a dot product (or other functions) between entries (weights) of the set of filter weights of the first filter and the input (from the one-dimensional vector 132) thereby creating a one-dimensional activation map of that first filter. In some embodiments, the filter step rate (stride) of the first filter is one element, two elements, three elements, four elements, five elements, six elements, seven elements, eight elements, nine elements, ten elements, or more than ten elements of the input space. Thus, consider the case in which a first filter has size 22 meaning that the set of weights of the first filter consists of 22 weights. That is, the first filter has twenty-two different filter weights. In such embodiments, this filter will compute the dot product (or other mathematical function) between a contiguous set of elements of input space that has a depth of 1 element, a width of 22 elements, and a height of one element, for a total number of values of input space of 22 per convolutional neural network path 140. Referring to FIG. 3, the activation map of the first filter associated with the first convolutional layer 302 is passed through the maxpooling layer 304 and serves as input to the second convolutional filter 306. There, the second filter associated with the second convolutional layer 306 has a fixed one-dimensional size that is convolved (stepped at a predetermined step rate) across the length of the input from the maxpooling layer 304 inputted into the second convolutional layer, computing a dot product (or other functions) between entries (weights) of the second filter associated with the second convolutional layer 306 and the input thereby creating a one-dimensional activation map of the second filter. Referring to FIG. 3, the activation map of the second filter of the second convolutional layer is passed through the second maxpooling layer 308 and subsequently the output of this second maxpooling layer 308 serves as input the scorer 152.

In some embodiments the filter weights of the convolutional filters in the network architecture are initialized to Gaussian noise prior to training against the training set.

A separate CNN for each chromosome/single track. In some embodiments, vector 132 in each vector set 130 consists of the genotypic information for a corresponding different chromosome in a plurality of chromosomes of the species. In some such embodiments, the network architecture 138 includes a plurality of convolutional neural network paths 140, the plurality of convolutional neural network paths comprising at least one different convolutional neural network path 140 for each chromosome in the plurality of chromosomes. Each different convolutional neural network path comprises a first convolutional layer and a second convolutional layer. In such embodiments, there is inputted, for each respective vector 132 in the respective vector set 130, the respective vector into the first convolutional layer of the respective convolutional neural network path that represents the chromosome associated with the respective vector, and a respective final layer of each convolutional neural network path in the plurality of convolutional neural network paths feeds a different plurality of values from the respective final layer into the scorer. The results of processing a training set using a network architecture 138 with such a configuration are presented in Example 4 in conjunction with FIGS. 6 through 11.

In some such embodiments, the network architecture comprises a plurality of first filter weights, each respective first filter weight in the plurality of first filter weights corresponding to a first convolutional layer in a convolutional neural network path in the plurality of convolutional neural network paths. Further, the network architecture comprises a plurality of second filter weights, each respective second filter weight in the plurality of second filter weights corresponding to a second convolutional layer in a convolutional neural network path in the plurality of convolutional neural network paths. The network architecture 138 comprises a plurality of first filters, each respective first filter having a first predetermined length. The network architecture comprises a plurality of second filters, each respective second filter having a second predetermined length. In such embodiments, each first filter in the first plurality of filters is convolved against a corresponding first convolutional layer in the plurality of convolutional neural network paths with a first predetermined stride, and each second filter in the plurality of second filters is convolved against a corresponding second convolutional layer in the plurality of convolutional neural network paths with a second predetermined stride.

In some such embodiments, the plurality of convolutional neural network paths is twenty-two, each respective convolutional neural network path in the plurality of convolutional neural network paths for a different autosomal human chromosome, the first predetermined length is between 10 and 30, the plurality of second filters consists of twenty-two second filters, the second predetermined length is between 5 and 15, the first predetermined stride is between 2 and 10, and the second predetermined stride is between 1 and 5.

A separate CNN for each chromosome/two tracks. In some embodiments, the genotypic information for each respective training subject further comprises, in addition to the first bin count described above, a second bin count for each respective bin in the plurality of bins, each respective second bin count representative of second genotypic information that has been measured from the biological sample and that maps onto the different region of the reference genome corresponding to the respective bin. A first vector set of a first training subject comprises a plurality of vectors that is divided into a first track comprising a first subset of the plurality of vectors of the vector set and a second subset of the plurality of vectors of the vector set. Each respective vector in the first subset consists of the first bin count for the different chromosome in the plurality of chromosomes of the species corresponding to the respective vector. Each respective vector in the second subset consists of the second bin count for the different chromosome in the plurality of chromosomes of the species corresponding to the respective vector. In such embodiments, the network architecture 138 comprises a plurality of convolutional neural network paths 140 including a respective first convolutional neural network path and a respective second convolutional neural network path for each respective chromosome in the plurality of chromosomes. Each respective first convolutional neural network path and respective second convolutional neural network path in the plurality of convolutional neural network paths comprises a first convolutional layer and a second convolutional layer. In such embodiments, for each respective vector in the first subset of the first vector set, the respective vector is inputted into the first convolutional layer of the respective first convolutional neural network path in the plurality of convolutional neural networks that represents the chromosome associated with the respective vector. Further, for each respective vector in the second subset of the first vector set, the respective vector is inputted into the first convolutional layer of the respective second convolutional neural network path in the plurality of convolutional neural network paths that represents the chromosome associated with the respective vector. In such embodiments, a respective final layer of each convolutional neural network path in the plurality of convolutional neural network paths to feed a different plurality of values from the respective final layer into the scorer. The results of processing a training set using a network architecture 138 with such a configuration are presented in Example 4 in conjunction with FIGS. 12, and 18-21, where bin counts data from cells that are deemed to not be white blood cells are partitioned into the first subset and bin count data from cells that are deemed to be white blood cells are partitioned into the second subset. More generally, in some embodiments the first bin count and the second bin count are different from each other and, for each respective bin in the plurality of bins, are each independently one of: (i) a number of sequence reads in sequencing data measured from cell-free nucleic acids in the biological sample that maps onto the region of the reference genome corresponding to the respective bin, (ii) a number of sequence reads in sequencing data measured from white blood cells in the biological sample that maps onto the region of the reference genome corresponding to the respective bin, (iii) a respective first number of paired sequence reads in sequencing data measured from cell-free nucleic acids in the biological sample that map onto the region of the reference genome corresponding to the respective bin, where each paired sequence read in the respective first number of paired sequence reads maps to a sequence in the region of the genome of the species that is within a first size range, (iv) a number of sequence reads in sequencing data obtained using a methylation sequencing assay of cell-free nucleic acids in the biological sample that have a predetermined methylation state and that map onto the region of the reference genome corresponding to the respective bin, (v) a mean nucleic acid length of sequence reads in sequencing data measured from cell-free nucleic acids in the biological sample that map onto the region of the reference genome corresponding to the respective bin, (vi) an allelic ratio of sequence reads measured from cell-free nucleic acid in the biological sample mapping onto the region of the reference genome corresponding to the respective bin, and (vii) a number of mutations identified in sequence reads measured from cell-free nucleic acid in the biological sample mapping onto the region of the reference genome corresponding to the respective bin.

A separate CNN for each chromosome/three tracks. In some embodiments, the genotypic information for each respective training subject comprises, in addition to the first bin count described above, a second bin count for each respective bin in the plurality of bins, each respective second bin count representative of second genotypic information that has been measured from the biological sample and that maps onto the different region of the reference genome corresponding to the respective bin. The genotypic information for each respective training subject further comprises a third bin count for each respective bin in the plurality of bins, each respective third bin count representative of third genotypic information that has been measured from the biological sample and that maps onto the different region of the reference genome corresponding to the respective bin. In such embodiments, a first vector set 130 of a first training subject comprises a plurality of vectors that is divided into (i) a first track comprising a first subset of the plurality of vectors of the first vector set, (ii) a second track comprising a second subset of the plurality of vectors of the first vector set, and (iii) a third track comprising a third subset of the plurality of vectors of the first vector set. Each respective vector in the first subset consists of the first bin count for the different chromosome in the plurality of chromosomes of the species corresponding to the respective vector. Each respective vector in the second subset consists of the second bin count for the different chromosome in the plurality of chromosomes of the species corresponding to the respective vector. Each respective vector in the third subset consists of the third bin count for the different chromosome in the plurality of chromosomes of the species corresponding to the respective vector. In such embodiments, the network architecture 138 comprises a plurality of convolutional neural network paths 140 including a respective first convolutional neural network path, a respective second convolutional neural network path, and a respective third convolutional neural network path for each respective chromosome in the plurality of chromosomes. Each respective first convolutional neural network path, second convolutional neural network path, and third convolutional neural network path in the plurality of convolutional neural network paths comprises a first convolutional layer and a second convolutional layer. In such embodiments, for each respective vector in the first subset of the first vector set, the respective vector is inputted into the first convolutional layer of the respective first convolutional neural network path in the plurality of convolutional neural network paths that represents the chromosome associated with the respective vector. For each respective vector in the second subset of the first vector set, the respective vector is inputted into the first convolutional layer of the respective second convolutional neural network path in the plurality of convolutional neural network paths that represents the chromosome associated with the respective vector. For each respective vector in the third subset of the first vector set, the respective vector is inputted into the first convolutional layer of the respective third convolutional neural network path in the plurality of convolutional neural network paths that represents the chromosome associated with the respective vector. A respective final layer of each respective convolutional neural network path in the plurality of convolutional neural network paths feeds a different plurality of values from the respective final layer into the scorer.

In some such embodiments the first bin count, the second bin count, and the third bin count are different from each other and, for each respective bin in the plurality of bins, are each independently one of: (i) a number of sequence reads in sequencing data measured from cell-free nucleic acids in the biological sample that maps onto the region of the reference genome corresponding to the respective bin, (ii) a number of sequence reads in sequencing data measured from white blood cells in the biological sample that maps onto the region of the reference genome corresponding to the respective bin, (iii) a respective first number of paired sequence reads in sequencing data measured from cell-free nucleic acids in the biological sample that map onto the region of the reference genome corresponding to the respective bin, where each paired sequence read in the respective first number of paired sequence reads maps to a sequence in the region of the genome of the species that is within a first size range, (iv) a number of sequence reads in sequencing data obtained using a methylation sequencing assay of cell-free nucleic acids in the biological sample that have a predetermined methylation state and that map onto the region of the reference genome corresponding to the respective bin, (v) a mean nucleic acid length of the sequence reads in sequencing data measured from cell-free nucleic acids in the biological sample that map onto the region of the reference genome corresponding to the respective bin, (vi) an allelic ratio of sequence reads measured from cell-free nucleic acid fragments in the biological sample mapping onto the region of the reference genome corresponding to the respective bin, and (vii) a number of mutations identified in sequence reads measured from cell-free nucleic acid in the biological sample mapping onto the region of the reference genome corresponding to the respective bin.

A single CNN for each chromosome/Single track—Binned Sequence Reads. In some embodiments, all or a portion of the reference genome is represented by a plurality of bins, each respective bin in the plurality of bins representing a different and non-overlapping region of the reference genome. In some such embodiments, the genotypic information for each respective training subject in the plurality of training subjects comprises a first bin count for each respective bin in the plurality of bins. Each respective first bin count is representative of a number of sequence reads in sequencing data measured from cell-free nucleic acids in a biological sample obtained from the training subject that maps onto the different regions of the reference genome corresponding to the respective bin.

In some such embodiments, a first vector set in the plurality of vectors sets that is formatted from the genotypic data construct for the first training subject is inputted into the network architecture in the form of an array of the vectors in the respective vector set. In some such embodiments, each vector in the first vector set represents a different chromosome in the genome of the species.

In some embodiments, the plurality of bins comprises ten thousand bins, each respective vector in the first vector set comprises each of the bins on the chromosome of the genome of the species corresponding to the respective vector.

In some such embodiments, the first convolutional layer is the first layer in the first convolutional neural network path and receives the respective vector set directly, responsive to input of the respective vector set in the plurality of vector sets, and the first filter has a set of filter weights comprising between five and fifty filter weights and is convolved in the causing step (b) of the procedure with a stride Y, where Y is between one and five.

The results of processing a training set using a network architecture 138 with such a configuration are presented in Example 4 in conjunction with FIGS. 6 through 11.

Double track—Binned Sequence Reads and WBC. In some embodiments, the genotypic data construct for each respective training subject in the plurality of training subjects includes, in addition to the first bin count described above in the section entitled "A single CNN for each chromosome/Single track—Binned Sequence Reads," a second bin count for each respective bin in the plurality of bins. Each respective second bin count representative of a number of sequence reads in sequencing data measured from white blood cells in the biological sample obtained from the respective training subject that maps onto different region of the reference genome corresponding to the respective bin. In such embodiments, the first vector set in the plurality of vectors sets that is formatted from the genotypic data construct for the first training subject is inputted into the network architecture in the form of a first track and a second track. Each respective element of each vector in the first track represents the first bin count for the corresponding bin in the plurality of bins. Each respective element of each vector in the second track represents the second bin count for the corresponding bin in the plurality of bins.

In some such embodiments, each vector in the first track of the first vector set represents a different chromosome in the genome of the species and each vector in the second track of the first vector set also represents a different chromosome in the genome of the species. In some such embodiments, the first track is inputted into a first convolutional neural network path and the second track is inputted into a second convolutional neural network path in the network architecture 138. In some such embodiments, the plurality of bins comprises ten thousand bins, and each respective vector in the plurality of vectors comprises each of the bins on the chromosome of the reference genome corresponding to the respective vector.

The results of processing a training set using a network architecture 138 with such a configuration are presented in Example 4 below in conjunction with FIGS. 12, and 18-21, where bin count data from cells that are deemed to not be white blood cells are partitioned into the first subset and bin count data from cells that are deemed to be white blood cells are partitioned into the second subset.

Double track—Binned Sequence Reads in two different size ranges. In some embodiments, all or a portion of the genome of the species is represented by a plurality of bins, each respective bin in the plurality of bins representing a different and non-overlapping region of the reference genome. Further, the genotypic data construct for each respective training subject in the plurality of training subjects comprises a first bin count for each respective bin in the plurality of bins. Each respective first bin count is representative of a respective first number of paired sequence reads in sequencing data measured from cell-free nucleic acids in the biological sample that map onto the region of the reference genome corresponding to the respective bin, where each paired sequence read in the respective first number of paired sequence reads maps to a sequence in the portions of the reference genome that is within a first size range.

The genotypic data construct for each training subject further comprises a second bin count for each respective bin in the plurality of bins. Each respective second bin count representative of a respective second number of paired sequence reads in sequencing data measured from cell-free nucleic acid in the biological sample obtained from the training subject that map onto the portion of the reference genome corresponding to the respective bin, where each paired sequence read in the respective second number of paired sequence reads maps to a sequence in the portions of the reference genome that is within a second size range. In some embodiments, the second size range and the first size range do not overlap each other.

It will be appreciated that the genotypic data construct for each training subject can further comprise additional bin counts for each respective bin in the plurality of bins. In such embodiments, each respective additional bin count is representative of an additional number of paired sequence reads in sequencing data measured from cell-free nucleic acid in the biological sample obtained from the training subject that map onto the region of the reference genome corresponding to the respective bin, where each paired sequence read in the respective additional number of paired sequence reads maps to a sequence in the region of the reference genome that is within another size range that is different from all the other size ranges.

In this way, each respective bin can have a plurality of bin counts, where each respective bin count in the plurality of bin counts is representative of a corresponding number of paired sequence reads in sequencing data measured from cell-free nucleic acid in the biological sample obtained from the training subject that map onto the different portions of the reference genome corresponding to the respective bin, where each paired sequence read in the corresponding number of paired sequence reads maps to a sequence in the portions of the reference genome that is within a corresponding size range associated with the respective bin count. In some such embodiments, the plurality of bin counts and concomitant corresponding size ranges is two, three, four, five, six, seven, eight, nine or ten. For instance, when the plurality of bin counts and concomitant corresponding size ranges is four, the genotypic data construct for each training subject comprise a first bin count, a second bin count, a third bin count and a fourth bin count for each respective bin in the plurality of bins. In such embodiments, each respective bin count is representative of a number of paired sequence reads in sequencing data measured from cell-free nucleic acid in the biological sample obtained from the training subject that map onto the different region of the reference genome corresponding to the respective bin, where each paired sequence read in the respective number of paired sequence reads maps to a sequence in the region of the reference genome that is within the size range that corresponds to the respective bin count.

Returning to the case where there are two bin counts per bin, a first vector set in the plurality of vectors sets that is formatted from the genotypic data construct for a first training subject is inputted into the network architecture in the form of a first track and a second track. Each respective element of each vector in the first track represents the first bin count for the corresponding bin in the plurality of bins. Each respective element of each vector in the second track represents the second bin count for the corresponding bin in the plurality of bins.

In some such embodiments, each vector in the first track of the first vector set represents a different chromosome in the reference genome and each vector in the second track of the second vector set also represents a different chromosome in the reference genome. This is illustrated in FIGS. 18-21 of Example 4 below, in which there are two tracks for each of the twenty-two human autosomal chromosomes for a total of 44 different convolutional neural network paths.

In some such embodiments, the plurality of bins comprises ten thousand bins, and each respective vector in the plurality of vectors comprises each of the bins on the chromosome of the reference genome corresponding to the respective vector.

Single track—Binned Sequence Reads (M-score) (WGBS in a bin). In some embodiments, all or a portion of the genome of the species is represented by a plurality of bins. Each respective bin in the plurality of bins represents a different and non-overlapping portion of the reference genome. The genotypic information for each respective training subject in the plurality of training subjects comprises a first bin count for each respective bin in the plurality of bins.

In some embodiments, each respective first bin count reflects a number of sequence reads in sequencing data obtained using a methylation sequencing assay of cell-free nucleic acids in the biological sample that have a predetermined methylation state and that map onto the region of the reference genome corresponding to the respective bin. An example methylation sequencing assay is whole genome bisulfite sequencing. In some such embodiments, the whole genome bisulfite sequencing identifies one or more methylation state vectors in accordance with Example 1 below and as further disclosed in U.S. patent application Ser. No. 16/352,602, entitled "Anomalous Fragment Detection and Classification," filed Mar. 13, 2019, or in accordance with any of the techniques disclosed in United States Provisional Patent Application No. 62/847,223, entitled "Model-Based Featurization and Classification," filed May 13, 2019, each of which is hereby incorporated by reference. In some embodiments, the methylation assay makes use of any of the sequencing pathways disclosed in Liu et al., 2019, "Bisulfite-free direct detection of 5-methylcytosine and 5-hydroxymethylcytosine at base resolution," Nature Biotechnology 37, pp. 424-429, which is hereby incorporated by reference.

In some embodiments, each respective first bin count reflects a number of sequence reads in sequencing data obtained using a methylation sequencing assay of cell-free nucleic acids in the biological sample that have a predetermined methylation state and that map onto the region of the reference genome corresponding to the respective bin. As an example, the number reflects methylation states based on the presence of methylation sites over a given length of nucleotide sequence. For example, a sequence read is counted if it includes two or more methylation sites for each 1000 bp of sequence. The threshold in a given sequence read can be set as one or more methylation sites for each 1000 bp, two or more methylation sites for each 1000 bp, three or more methylation sites for each 1000 bp, four or more methylation sites for each 1000 bp, five or more methylation sites for each 1000 bp, six or more methylation sites for each 1000 bp, seven or more methylation sites for each 1000 bp, eight or more methylation sites for each 1000 bp, nine or more methylation sites for each 1000 bp, ten or more methylation sites for each 1000 bp, 12 or more methylation sites for each 100 bp, or 15 or more methylation sites for each 1000 bp. In some embodiments, the given length can be shorter or longer than 1000 bp. In other embodiments, other values reflecting the distribution and frequency of methylation sites can be used, including but not limited to those disclosed in Example 1 below and as further disclosed in U.S. patent application Ser. No. 16/352,602, entitled "Anomalous Fragment Detection and Classification," filed Mar. 13, 2019, or any of the techniques disclosed in U.S. Provisional Patent Application No. 62/847,223, entitled "Model-Based Featurization and Classification," filed May 13, 2019, each of which is hereby incorporated by reference. A methylation sequencing assay refers to a physical assay that generates sequence reads that can be used to determine the methylation status of a plurality of CpG sites, or methylation patterns, across the genome. An example of such a methylation sequencing assay can include the bisulfite treatment of cfDNA for conversion of unmethylated cytosines (e.g., CpG sites) to uracil (e.g., using EZ DNA Methylation—Gold or an EZ DNA Methylation—Lightning kit (available from Zymo Research Corp)). Alternatively, an enzymatic conversion step (e.g., using a cytosine deaminase (such as APOBEC-Seq (available from NEBiolabs))) may be used for conversion of unmethylated cytosines to uracils. Following conversion, the converted cfDNA molecules can be sequenced through a whole genome sequencing process or a targeted gene sequencing panel and sequence reads used to assess methylation status at a plurality of CpG sites. Methylation-based sequencing approaches are known in the art (e.g., see United States Patent Publication No. 2014/0080715, which is incorporated herein by reference). In another embodiment, DNA methylation may occur in cytosines in other contexts, for example CHG and CHH, where H is adenine, cytosine or thymine. Cytosine methylation in the form of 5-hydroxymethylcytosine may also assessed (see, e.g., WO 2010/037001 and WO 2011/127136, which are incorporated herein by reference), and features thereof, using the methods and procedures disclosed herein. In some embodiments, a methylation sequencing assay need not perform a base conversion step to determine methylation status of CpG sites across the genome. For example, such methylation sequencing assays can include PacBio sequencing or Oxford Nanopore sequencing.

In some such embodiments, a first vector set in the plurality of vectors sets that is formatted from the genotypic data construct for a first training subject is inputted into the network architecture 138 in the form of an array of the vectors in the respective vector set. In some embodiments, each vector in the first vector set represents a different chromosome in the reference genome. In some embodiments, each vector in the first vector set represents multiple chromosomes in the reference genome. In some embodiments, the plurality of bins comprises ten thousand bins, and each respective vector in the first vector set comprises each of the bins on the chromosome of the reference genome corresponding to the respective vector.

Single track—Mean sequence read length per bin. In some embodiments, all or a portion of the reference genome is represented by a plurality of bins, each respective bin in the plurality of bins representing a different and non-overlapping portion of the reference genome. In some such embodiments, the genotypic information for each respective training subject in the plurality of training subjects comprises a first bin count for each respective bin in the plurality of bins. Each respective first bin count is representative of a mean length of the sequence reads in sequencing data measured from cell-free nucleic acids in a biological sample obtained from the respective training subject that maps onto the region of the reference genome corresponding to the respective bin. In some such embodiments, a first vector set in the plurality of vectors sets that is formatted from the genotypic data construct for a first training subject is inputted into the network architecture in the form of vectors in the first vector set. In some embodiments, each vector in the first vector set represents a different chromosome in the genome of the species. In some embodiments, each vector in the first vector set represents a plurality of chromosomes in the genome of the species. In some embodiments, the plurality of bins comprises ten thousand bins, and each respective vector in the first vector set comprises each of the bins on the chromosome of the reference genome corresponding to the respective vector.

Single track—allelic ratio. In some embodiments, all or a portion of the reference genome is represented by a plurality of bins, each respective bin in the plurality of bins representing a different and non-overlapping region of the reference genome. The genotypic information for each respective training subject in the plurality of training subjects comprises a first bin count for each respective bin in the plurality of bins. Each respective first bin count is representative of an allelic ratio of sequence reads measured from cell-free nucleic acids in a biological sample obtained from the respective training subject that maps onto the different region of the reference genome corresponding to the respective bin.

In some embodiments a first vector set in the plurality of vectors sets formatted from the genotypic data construct for a first training subject is inputted into the network architecture. In some embodiments, each vector in the first vector set represents a different single chromosome in the reference genome. In alternative embodiments, each vector in the first vector set represents a plurality of chromosomes in the reference genome.

In some embodiments, the plurality of bins comprises ten thousand bins, and each respective vector in the first vector set comprises each of the bins on the chromosome of the reference genome corresponding to the respective vector.

Single track—Counts of mutations in a bin. In some embodiments, all or a portion of the reference genome is represented by a plurality of bins. Each respective bin in the plurality of bins representing a different and non-overlapping region of the reference genome. The genotypic information for each respective training subject in the plurality of training subjects comprises a first bin count for each respective bin in the plurality of bins. Each respective first bin count is representative of a number of mutations identified in sequence reads measured from cell-free nucleic acids in a biological sample obtained from the respective training subject that maps onto the region of the reference genome corresponding to the respective bin.

A first vector set in the plurality of vectors sets formatted from the genotypic data construct for a first training subject is inputted into the network architecture 138. In some embodiments, each vector in the first vector set represents a different single chromosome in the reference genome. In some embodiments, a vector in the first vector set represents a plurality of chromosomes in the reference genome.

In some embodiments, the plurality of bins comprises ten thousand bins, and each respective vector in the plurality of vectors comprises each of the bins on the chromosome of the reference genome corresponding to the respective vector.

Multiple tracks, with either one CNN path for all the chromosomes or several different CNN paths for each chromosome. In some embodiments, the genotypic information for each respective training subject comprises, in addition to the first bin count described above, two or more additional bin counts for each respective bin in the plurality of bins, each respective additional bin count representative of a different form of genotypic information that has been measured from the biological sample and that maps onto the different region of the reference genome corresponding to the respective bin. In such embodiments, a first vector set 130 of a first training subject comprises a plurality of vectors that is divided into a plurality of tracks, each track comprising a corresponding subset of the plurality of vectors of the first vector set that contains corresponding bin count information. Each respective vector in the first subset consists of the first bin count type information, each respective vector in the second subset consists of the second bin count type information, and so forth. In such embodiments, the network architecture 138 comprises a plurality of convolutional neural network paths 140 including a respective convolutional neural network path for each different type of bin count that was measured from the biological samples. Each respective convolutional neural network path in the plurality of convolutional neural network paths comprises a first convolutional layer and a second convolutional layer. In such embodiments, for each respective vector in a respective subset of the first vector set, the respective vector is inputted into the first convolutional layer of the corresponding convolutional neural network path in the plurality of convolutional neural network paths. A respective final layer of each respective convolutional neural network path in the plurality of convolutional neural network paths feeds a different plurality of values from the respective final layer into the scorer. In some embodiments, 1, 2, 3, 4, 5, 6, 7, 8, 9, or 10 different types of bin count information are measured from the training samples and each such bin count type is assigned to one or more separate convolutional neural network paths 140 in the network architecture 138.

In some such embodiments each respective bin count type is different from each other and, for each respective bin count type in the plurality of bin counts types, are each independently one of: (i) a number of sequence reads in sequencing data measured from cell-free nucleic acids in the biological sample that maps onto the region of the reference genome corresponding to the respective bin, (ii) a number of sequence reads in sequencing data measured from white blood cells in the biological sample that maps onto the region of the reference genome corresponding to the respective bin, (iii) a respective first number of paired sequence reads in sequencing data measured from cell-free nucleic acids in the biological sample that map onto the region of the reference genome corresponding to the respective bin, where each paired sequence read in the respective first number of paired sequence reads maps to a sequence in the region of the genome of the species that is within a first size range (e.g., a value of less than 160 nucleotides. In some embodiments, the first threshold length is 150 nucleotides or less. In some embodiments, the first threshold length is 140 nucleotides or less. In some embodiments, the first threshold length is 130 nucleotides or less. In some embodiments, the first threshold length is 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, or fewer nucleotides), (iv) a number of sequence reads in sequencing data obtained using a methylation sequencing assay of cell-free nucleic acids in the biological sample that have a predetermined methylation state and that map onto the region of the reference genome corresponding to the respective bin, (v) a mean length of the sequence reads in sequencing data measured from cell-free nucleic acid in the biological sample that maps onto the region of the reference genome corresponding to the respective bin, (vi) an allelic ratio of sequence reads measured from cell-free nucleic acid in the biological sample mapping onto the region of the reference genome corresponding to the respective bin, and (vii) a number of mutations identified in sequence reads measured from cell-free nucleic acid in the biological sample mapping onto the region of the reference genome corresponding to the respective bin.

Block 218. Referring to block 218 of FIG. 2B, a plurality of scores 136 is obtained from the scorer. Each score in the plurality of scores corresponds to the input of a vector set in the plurality of vector sets into the network architecture.

In some embodiments, the scorer 152 provides a k-dimensional score for each respective vector set in the plurality of vector sets. Each element in the k-dimensional score represents a probability or likelihood that the training subject associated with the respective vector set has a corresponding cancer in the plurality of cancer conditions. In some embodiments, k is a positive integer of 2 or greater. In some embodiments, k is a positive integer of 3 or greater. In some embodiments, the value of k matches the number of cancer condition in plurality of cancer conditions. For instance, if the plurality of cancer conditions is 10, k has the value 10. In some embodiments, the value of k matches the number of cancer conditions in plurality of cancer conditions plus 1. For instance, if the plurality of cancer conditions is 10, k has the value 11, where the extra value represents no match being made to a cancer type by the network architecture for a given training subject.

In some embodiments, the scorer 152 computes the k-dimensional score for each respective vector set 130 in the plurality of vector sets using a normalized exponential function of the output of the final layer in the first convolutional neural network path. See, Gold, 1996, "Softmax to Softassign: Neural Network Algorithms for Combinatorial Optimization," Journal of Artificial Neural Networks 2, 381-399, which is hereby incorporated by reference.

In some embodiments, the scorer 152 comprises a decision tree algorithm, a multiple additive regression tree algorithm, a clustering algorithm, principal component analysis algorithm, a nearest neighbor analysis algorithm, a linear discriminant analysis algorithm, a quadratic discriminant analysis algorithm, a support vector machine (SVM) algorithm, an evolutionary method, a projection pursuit algorithm, or ensembles thereof.

Decision trees are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York. pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

Clustering is described at pages 211-256 of Duda and Hart, *Pattern Classification and Scene Analysis,* 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in the training set. If distance is a good measure of similarity, then the distance between reference entities in the same cluster will be significantly less than the distance between the reference entities in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 218 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., Pattern Classification, 2$^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (3d ed.), Wiley, New York, N.Y.; and Backer, 1995, Computer-Assisted Reasoning in Cluster Analysis, Prentice Hall, Upper Saddle River, N.J., each of which is hereby incorporated by reference. Particular exemplary clustering techniques that can be used in the present disclosure include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. Such clustering can be on the set of first features $\{p_1, \ldots, p_{N-K}\}$ (or the principal components derived from the set of first features). In some embodiments, the clustering comprises unsupervised clustering (block 490) where no preconceived notion of what clusters should form when the training set is clustered are imposed.

Principal component analysis (PCA) algorithms are described in Jolliffe, 1986, *Principal Component Analysis*, Springer, New York, which is hereby incorporated by reference. PCA is also described in Draghici, 2003, *Data Analysis Tools for DNA Microarrays*, Chapman & Hall/CRC, which is hereby incorporated by reference. Principal components (PCs) are uncorrelated and are ordered such that the $k^{th}$ PC has the $k^{th}$ largest variance among PCs. The $k^{th}$ PC can be interpreted as the direction that maximizes the variation of the projections of the data points such that it is orthogonal to the first k−1 PCs. The first few PCs capture most of the variation in a training set. In contrast, the last few PCs are often assumed to capture only the residual 'noise' in the training set.

SVM algorithms are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5$^{th}$ Annual ACM Workshop on Computational Learning Theory, ACM Press, Pittsburgh, Pa., pp. 142-152; Vapnik, 1998, *Statistical Learning Theory*, Wiley, New York; Mount, 2001, *Bioinformatics:* sequence and genome analysis, Cold Spring Harbor Laboratory Press, Cold Spring Harbor, N.Y.; Duda, *Pattern Classification*, Second Edition, 2001, John Wiley & Sons, Inc., pp. 259, 262-265; and Hastie, 2001, *The Elements of Statistical Learning*, Springer, New York; and Furey et al., 2000, *Bioinformatics* 16, 906-914, each of which is hereby incorporated by reference in its entirety. When used for classification, SVMs separate a given set of binary labeled data training set with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In some embodiments, the scorer 152 comprises a plurality of fully-connected layers and a binomial or multinomial logistic regression cost layer where a fully-connected layer in the plurality of fully-connected layers feeds into the binomial or multinomial logistic regression cost layer. Logistic regression algorithms are disclosed in Agresti, *An Introduction to Categorical Data Analysis*, 1996, Chapter 5, pp. 103-144, John Wiley & Son, New York, which is hereby incorporated by reference.

Block 220. Referring to block 218 of FIG. 2B, a comparison of respective scores in the plurality of scores 136 to the corresponding cancer type of the corresponding training subject in the plurality of training subjects is used to adjust at least the weights of the first filter and the weights of the second weight thereby training the network architecture to classify a cancer type, in the plurality of cancer conditions, for the species. Errors in cancer condition assignments made by the network architecture 138, as verified against the training data (e.g., cancer class of training subject 124), are then back-propagated through the weights of the neural network in order to train the network architecture 138. For instance, the filter weights of respective filters in the convolutional layers of the network are adjusted in such back-propagation. In an exemplary embodiment, the network architecture 138 is trained against the errors in the cancer condition assignments made by the network architecture 138, in view of the training data, by stochastic gradient descent with the AdaDelta adaptive learning method (Zeiler, 2012 "ADADELTA: an adaptive learning rate method," CoRR, vol. abs/1212.5701, which is hereby incorporated by reference), and the back propagation algorithm provided in Rumelhart et al., 1988, "Neurocomputing: Foundations of research," ch. Learning Representations by Back-propagating Errors, pp. 696-699, Cambridge, Mass., USA: MIT Press, which is hereby incorporated by reference.

In this way, the network architecture 138 learns parameters within the first and second convolutional layers of each convolutional neural network path that activate when they see some specific type of feature at some spatial position in the input. The initial weights of each filter in a convolutional layer are obtained by training the convolutional neural network against the training set. Accordingly, the operation of the network architecture yields more complex features than the features historically used to classify cancer conditions.

Block 222. Referring to block 222 of FIG. 2B, the network architecture 138, now trained in accordance with blocks 202 through 220, can be used to classify a test subject to a cancer condition in the plurality of cancer conditions using sequence read information of cell-free nucleic acids in a biological sample obtained from the test subject as input to the trained network architecture.

Further, in some embodiments, a training or test subject from whom a biological sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., patients over the age of 40. Another particular class of subjects, e.g., patients that can benefit from a method of the present disclosure is pediatric patients, who can be at higher risk of chronic heart symptoms. Furthermore, a subject, e.g., patient from whom a sample is taken, or is treated by any of the methods or compositions described herein, can be male or female. In some embodiments, any of the disclosed methods further comprise providing a therapeutic intervention or imaging of a subject based on the determination of whether the test subject has a cancer.

Example 1: Generation of Methylation State Vector

Figure 22:
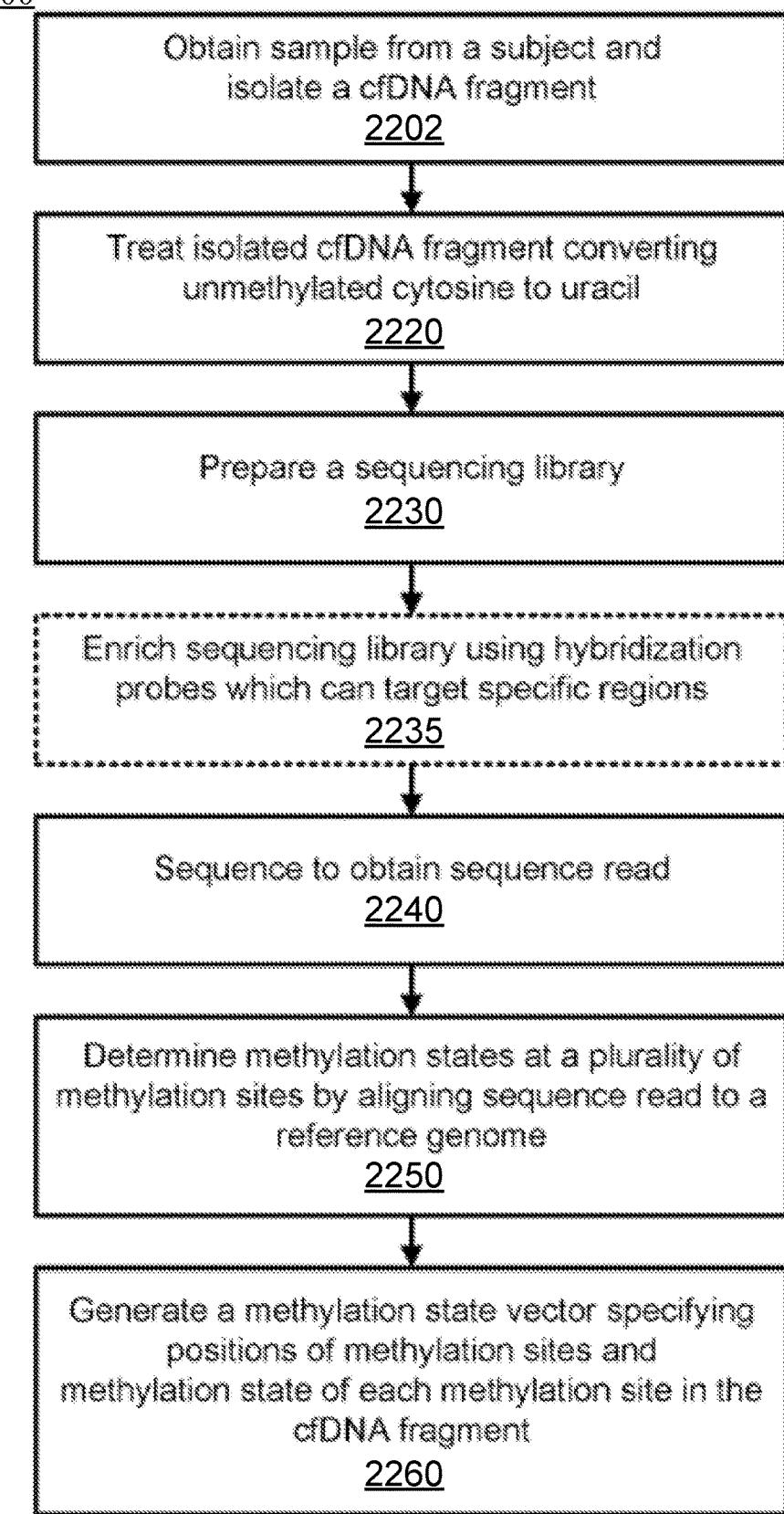
FIG. 22 is a sample flowchart of a method for obtaining a methylation information for the purposes of screening for a cancer condition in accordance with some embodiments of the present disclosure.

FIG. 22 is a flowchart describing a process 2200 of sequencing a fragment of cfDNA to obtain a methylation state vector, according to an embodiment in accordance with the present disclosure.

Referring to step 2202, the cfDNA fragments are obtained from the biological sample (e.g., as discussed above in conjunction with FIG. 2). Referring to step 2220, the cfDNA fragments are treated to convert unmethylated cytosines to uracils. In one embodiment, the DNA is subjected to a bisulfite treatment that converts the unmethylated cytosines of the fragment of cfDNA to uracils without converting the methylated cytosines. For example, a commercial kit such as the EZ DNA Methylation™-Gold, EZ DNA Methylation™-Direct or an EZ DNA Methylation™-Lightning kit (available from Zymo Research Corp (Irvine, Calif.)) is used for the bisulfite conversion in some embodiments. In other embodiments, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, Mass.).

From the converted cfDNA fragments, a sequencing library is prepared (step 2230). Optionally, the sequencing library is enriched 2235 for cfDNA fragments, or genomic regions, that are informative for cancer status using a plurality of hybridization probes. The hybridization probes are short oligonucleotides capable of hybridizing to particularly specified cfDNA fragments, or targeted regions, and enriching for those fragments or regions for subsequent sequencing and analysis. Hybridization probes may be used to perform a targeted, high-depth analysis of a set of specified CpG sites of interest to the researcher. Once prepared, the sequencing library or a portion thereof can be sequenced to obtain a plurality of sequence reads (2240). The sequence reads may be in a computer-readable, digital format for processing and interpretation by computer software From the sequence reads, a location and methylation state for each of CpG site is determined based on alignment of the sequence reads to a reference genome (2250). A methylation state vector for each fragment specifying a location of the fragment in the reference genome (e.g., as specified by the position of the first CpG site in each fragment, or another similar metric), a number of CpG sites in the fragment, and the methylation state of each CpG site in the fragment (2260).

Example 2: Obtaining a Plurality of Sequence Reads

Figure 23:
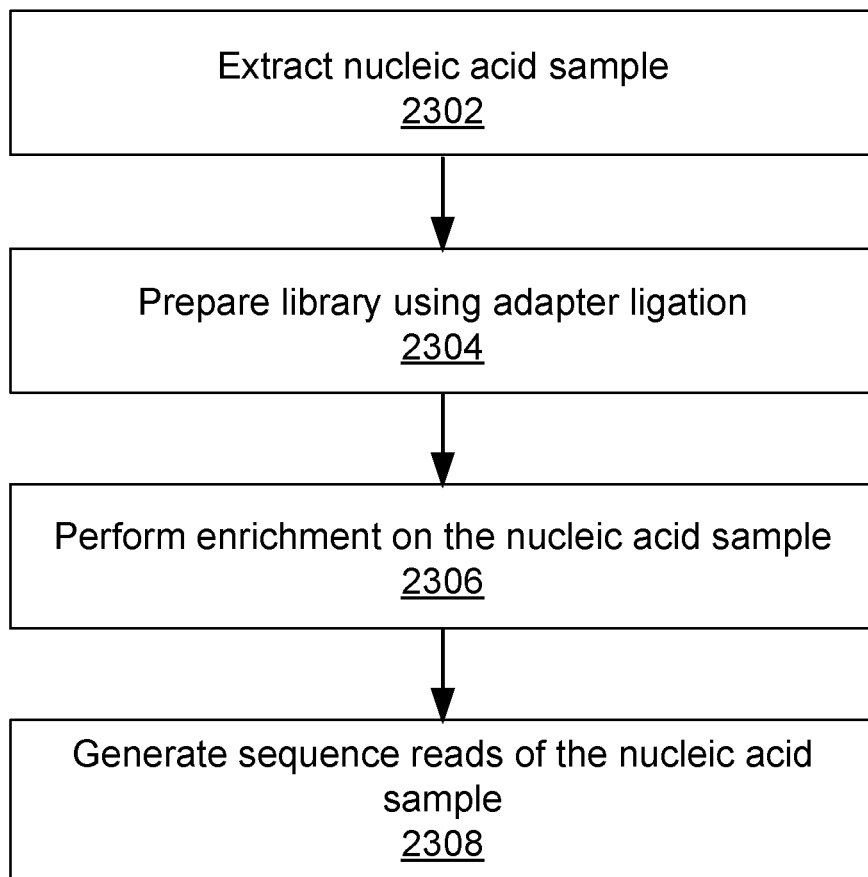
FIG. 23 illustrates a sample flowchart of a method for preparing a nucleic acid sample for sequencing in accordance with some embodiments of the present disclosure.

FIG. 23 is flowchart of a method 2300 for preparing a nucleic acid sample for sequencing according to one embodiment. The method 2300 includes, but is not limited to, the following steps. For example, any step of the method 2300 may comprise a quantitation sub-step for quality control or other laboratory assay procedures known to one skilled in the art.

In block 2302, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In block 2304, a sequencing library is prepared. During library preparation, unique molecular identifiers (UMI) are added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment. This provides a way to identify sequence reads that came from the same original fragment in downstream analysis.

In block 2306, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer type or tissue of origin). For a given workflow, the probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a gene panel to analyze particular mutations or target regions of the genome (e.g., of the human or another organism) that are suspected to correspond to certain cancers or other types of diseases. Moreover, the probes may cover overlapping portions of a target region.

Figure 24:
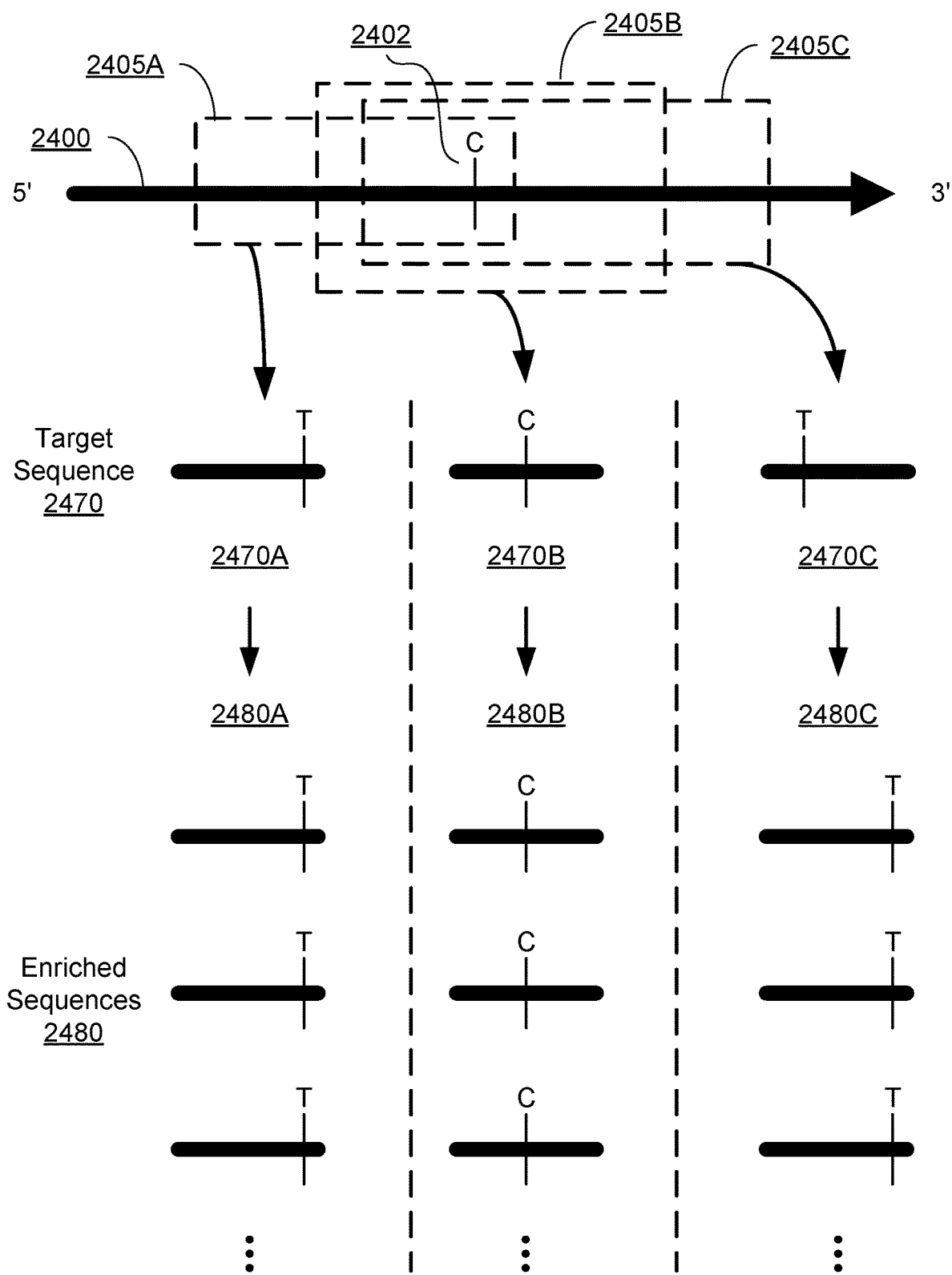
FIG. 24 is a graphical representation of the process for obtaining sequence reads in accordance with some embodiments of the present disclosure.

FIG. 24 is a graphical representation of the process for obtaining sequence reads according to one embodiment. FIG. 24 depicts one example of a nucleic acid segment 2000 from the sample. Here, the nucleic acid segment 2400 can be a single-stranded nucleic acid segment, such as a single stranded. In some embodiments, the nucleic acid segment 2400 is a double-stranded cfDNA segment. The illustrated example depicts three regions 2405A, 2405B, and 2405C of the nucleic acid segment that can be targeted by different probes. Specifically, each of the three regions 2405A, 2405B, and 2405C includes an overlapping position on the nucleic acid segment 2400. An example overlapping position is depicted in FIG. 24 as the cytosine ("C") nucleotide base 2402. The cytosine nucleotide base 2402 is located near a first edge of region 2405A, at the center of region 2405B, and near a second edge of region 2405C.

In some embodiments, one or more (or all) of the probes are designed based on a gene panel to analyze particular mutations or target regions of the genome (e.g., of the human or another organism) that are suspected to correspond to certain cancers or other types of diseases. By using a targeted gene panel rather than sequencing all expressed genes of a genome, also known as "whole exome sequencing," the method 2400 may be used to increase sequencing depth of the target regions, where depth refers to the count of the number of times a given target sequence within the sample has been sequenced. Increasing sequencing depth reduces required input amounts of the nucleic acid sample.

Hybridization of the nucleic acid sample 2400 using one or more probes results in an understanding of a target sequence 2470. As shown in FIG. 24, the target sequence 2470 is the nucleotide base sequence of the region 2405 that is targeted by a hybridization probe. The target sequence 2470 can also be referred to as a hybridized nucleic acid fragment. For example, target sequence 2470A corresponds to region 2405A targeted by a first hybridization probe, target sequence 2470B corresponds to region 2405B targeted by a second hybridization probe, and target sequence 2470C corresponds to region 2405C targeted by a third hybridization probe. Given that the cytosine nucleotide base 2402 is located at different locations within each region 2405A-C targeted by a hybridization probe, each target sequence 2470 includes a nucleotide base that corresponds to the cytosine nucleotide base 2402 at a particular location on the target sequence 2470.

After a hybridization step, the hybridized nucleic acid fragments are captured and may also be amplified using PCR. For example, the target sequences 2470 can be enriched to obtain enriched sequences 2480 that can be subsequently sequenced. In some embodiments, each enriched sequence 2080 is replicated from a target sequence 2470. Enriched sequences 2480A and 2480C that are amplified from target sequences 2470A and 2470C, respectively, also include the thymine nucleotide base located near the edge of each sequence read 2480A or 2480C. As used hereafter, the mutated nucleotide base (e.g., thymine nucleotide base) in the enriched sequence 2480 that is mutated in relation to the reference allele (e.g., cytosine nucleotide base 2402) is considered as the alternative allele. Additionally, each enriched sequence 2480B amplified from target sequence 2470B includes the cytosine nucleotide base located near or at the center of each enriched sequence 2480B.

In block 2408, sequence reads are generated from the enriched DNA sequences, e.g., enriched sequences 2480 shown in FIG. 24. Sequencing data may be acquired from the enriched DNA sequences by known means in the art. For example, the method 2300 may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis such as described above in conjunction with FIG. 2.

Example 3: The Circulating Cell-Free Genome Atlas Study (CCGA) Cohort

Subjects from the CCGA [NCT02889978] were used as training subjects in Example 4 of the present disclosure. CCGA is a prospective, multi-center, observational cfDNA-based early cancer detection study that has enrolled 9,977 of 15,000 demographically-balanced participants at 141 sites. Blood was collected from subjects with newly diagnosed therapy-naive cancer (C, case) and participants without a diagnosis of cancer (noncancer [NC], control) as defined at enrollment. This preplanned substudy included 878 cases, 580 controls, and 169 assay controls (n=1627) across twenty tumor types and all clinical stages.

All samples were analyzed by: 1) paired cfDNA and white blood cell (WBC)-targeted sequencing (60,000×, 507 gene panel); a joint caller removed WBC-derived somatic variants and residual technical noise; 2) paired cfDNA and WBC whole-genome sequencing (WGS; 35×); a novel machine learning algorithm generated cancer-related signal scores; joint analysis identified shared events; and 3) cfDNA whole-genome bisulfite sequencing (WGBS; 34×); normalized scores were generated using abnormally methylated fragments. In the targeted assay, non-tumor WBC-matched cfDNA somatic variants (SNVs/indels) accounted for 76% of all variants in NC and 65% in C. Consistent with somatic mosaicism (e.g., clonal hematopoiesis), WBC-matched variants increased with age; several were non-canonical loss-of-function mutations not previously reported. After WBC variant removal, canonical driver somatic variants were highly specific to C (e.g., in EGFR and PIK3CA, 0 NC had variants vs 11 and 30, respectively, of C). Similarly, of 8 NC with somatic copy number alterations (SCNAs) detected with WGS, four were derived from WBCs. WGBS data of the CCGA reveals informative hyper- and hypo-fragment level CpGs (1:2 ratio); a subset of which was used to calculate methylation scores. A consistent "cancer-like" signal was observed in <1% of NC participants across all assays (representing potential undiagnosed cancers). An increasing trend was observed in NC vs stages I-III vs stage IV (nonsyn. SNVs/indels per Mb [Mean±SD] NC: 1.01±0.86, stages I-III: 2.43±3.98; stage IV: 6.45±6.79; WGS score NC: 0.00±0.08, I-III: 0.27±0.98; IV: 1.95±2.33; methylation score NC: 0±0.50; I-III: 1.02±1.77; IV: 3.94±1.70). These data demonstrate the feasibility of achieving >99% specificity for invasive cancer, and support the promise of cfDNA assay for early cancer detection.

Example 4: Convolutional Neural Network for Cancer Classification on Re-Normalized Bincounts Referring to FIGS. 3-4 and 6-21, an example for classifying a cancer condition, in a plurality of different cancer conditions, for humans is provided. A total of 1764 training subjects from CCGA data (Example 3) were used as a training set in this example. For each respective training subject in the 1764 training subjects, the following information was obtained: (i) a cancer condition 124 of the respective training subject and (ii) a genotypic data construct 126 that includes genotypic information for each respective chromosome 128 in a plurality of chromosomes for the respective training subject as outlined above in Example 3.

In some portions of this example, the human genome is represented by a plurality of bins. Each respective bin in the plurality of bins represents a different portion of the human genome. The genotypic information for each respective human chromosome in the genotypic data construct 126 for each of the training subjects comprises a bin count for each respective bin in the plurality of bins. As is detailed for specific figures below, each respective bin count is representative of genotypic information arising in the respective bin that has been measured from a biological sample obtained from the corresponding training subject and that maps onto the different region of the genome of the species represented by the respective bin. For example, sequence reads measured using a training subject's biological sample that map to the region of the human genome represented by a particular bin.

Bins within the genotypic data constructs 126 were filtered on variance for B-score computation thereby reducing the number of bins used for each subject from about thirty thousand bins down to approximately twenty-five thousand bins. This form of pruning of bins is described above in conjunction with block 202 of FIG. 2A.

Next, bin values for each bin were re-normalized to 'align' them on an expected distribution.

In some embodiments, the genotypic data construct 126 also provides a mask Boolean for each bin, which is associated with whether the bin count deviation for a bin can be explained by the bin count for the bin arising from white blood cells. Additional details can be found in U.S. Pat. App. No. 62/642,506, filed on Mar. 13, 2018 and entitled "IDEN- TIFYING COPY NUMBER ABERRATIONS," which is hereby incorporated by reference herein in its entirety.

For score analysis, all types of cancers were stratified in the training set but only breast, lung, uterine, colorectal, melanoma and renal have individual labels. The other cancer types were labeled together as "other."

Each genotypic data construct 126 in the plurality of genotypic data constructs of the training set were formatted into corresponding vector sets 130 comprising a corresponding one or more vectors 132, thereby creating a plurality of vector sets.

Figure 1B:
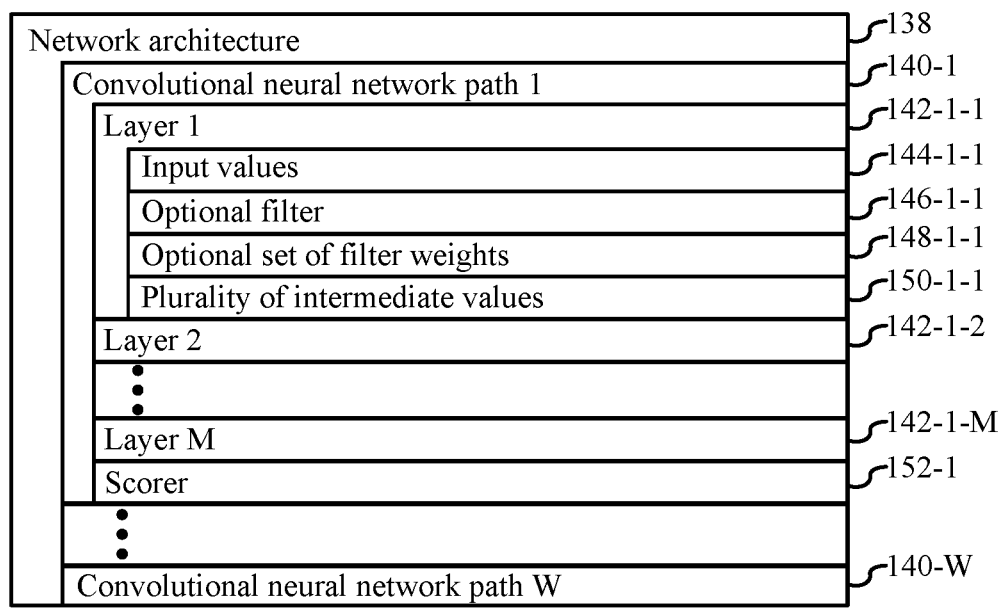

The vector sets were provided to a network architecture 138 comprising a first convolutional neural network path 140, which in turn is comprised of a first plurality of layers including a first convolutional layer 302 associated with a first comprising a first set of filter weights 148 (FIG. 1B), for sequentially receiving vector sets 130 in the plurality of vector sets. The network architecture also included a scorer 152. More particularly, FIG. 3 illustrates a network architecture 138 that is used in this example. As illustrated in FIG. 3, within each convolutional neural network path 140, the output of each layer in the plurality of layers of the network path 140 other than a final layer serves as input into another layer in the plurality of layers. The plurality of layers comprises a second convolutional layer 306. The first convolutional layer 302 includes at least a first filter 146 comprising a first set of filter weights 148. The second convolutional layer 306 includes at least a second filter 146 comprising a second set of weights 148. As further illustrated in FIG. 3, each convolutional neural network path 140 further comprises a first pooling layer 304 and a second pooling layer 308.

Responsive to input of a respective vector set 130 in the plurality of vector sets 130 into the network architecture 138, a procedure is performed. The procedure comprises (a) inputting a first plurality of input values into the first convolutional layer 302 as a first function of values in the respective vector set, (b) causing the first convolutional layer to feed a first plurality of intermediate values computed as a second function of: (i) at least the first set of filter weights and (ii) the first plurality of input values, into another layer in the convolutional neural network path, (c) causing the second convolutional layer to feed second intermediate values, as a third function of (i) the second set of filter weights and (ii) input values received by the second convolutional layer 306 from another layer in the first convolutional neural network path, and (d) causing a final layer in the first convolutional neural network path to feed a plurality of values from the final layer into the scorer 152. The procedure further causes the first pooling layer 304 to feed a third plurality of intermediate values computed as a first pooling function of the first plurality of intermediate values from the first convolutional layer 302 into the second convolutional layer 306. The procedure further causes the second pooling layer 308 to feed a fourth plurality of intermediate values computed as a second pooling function of the second plurality of intermediate values from the second convolutional layer 308 into the scorer 152 as illustrated in FIG. 3. The scorer 152 provides a k-dimensional score for each respective vector set 130 in the plurality of vector sets. Each element in the k-dimensional score represents a probability or likelihood that the training subject associated with the respective vector set has a corresponding cancer condition in the plurality of cancer conditions.

In this example, the scorer 152 computes the k-dimensional score for each respective vector set in the plurality of vector sets using a normalized exponential function of the output of the final layer of each of 22 convolutional neural network paths, each path representing one of the 22 human autosomal chromosomes. This is illustrated in FIG. 3. The network architecture 138 includes 22 convolutional neural network paths, one for each of the 22 autosomal human chromosomes. In this example, each vector 132 in each vector set 130 consists of the genotypic information for a corresponding different human autosomal chromosome. The inputting step of the procedure inputs, for each respective vector 132 in a respective vector set 130, the respective vector into the first convolutional layer 302 of the respective convolutional neural network path 140 that represents the chromosome associated with the respective vector 132. The maxpooling layer 308 of each convolutional neural network path 140 feeds a different plurality of values into the scorer 152.

In this way, a plurality of scores are obtained from the scorer. Each score in the plurality of scores corresponds to the input of a vector set 130 in the plurality of vector sets into the network architecture 138. A comparison of respective scores in the plurality of scores to the corresponding cancer condition 124 (cancer type in this example) of the corresponding training subject in the plurality of training subjects to adjust the filter weights of the first and second convolutional layers (302, 306) of each convolutional neural network path 140 thereby training the network architecture 138 to classify a cancer condition, in the plurality of cancer conditions, for humans.

Figure 4:
FIG. 4 illustrates an example set of filter weights of a chromosome in the plurality of convolutional neural network paths in a network architecture in accordance with an embodiment of the present disclosure.

FIG. 4 illustrates the filter weights 148 associated with a chromosome in a convolutional neural network path 140 in the network architecture 138 of FIG. 3. That is, the filter weights 148 of the first convolutional layer 302 for a chromosome is horizontally displayed in FIG. 4. Each filter weight in the set of filter weights of the first filter is convolved against the first convolutional layer 302 meaning that a dot product is taken between a weight in the set of filter weights and a value of a corresponding element in the convolutional layer 302. As illustrated in FIG. 4, the set of filter weights of the filter 146 includes 22 weights, each weight ranging in value where the range of values is grey-scaled between a low value (light color) and a high value (dark grey). Thus, when convolving the filter, the dot product of each weight of the set of filter weights of the filter and a corresponding element of the first convolutional filter 302 is taken. FIG. 4 represents the filter weights after they have been trained using the data of the training subject.

Figure 6:
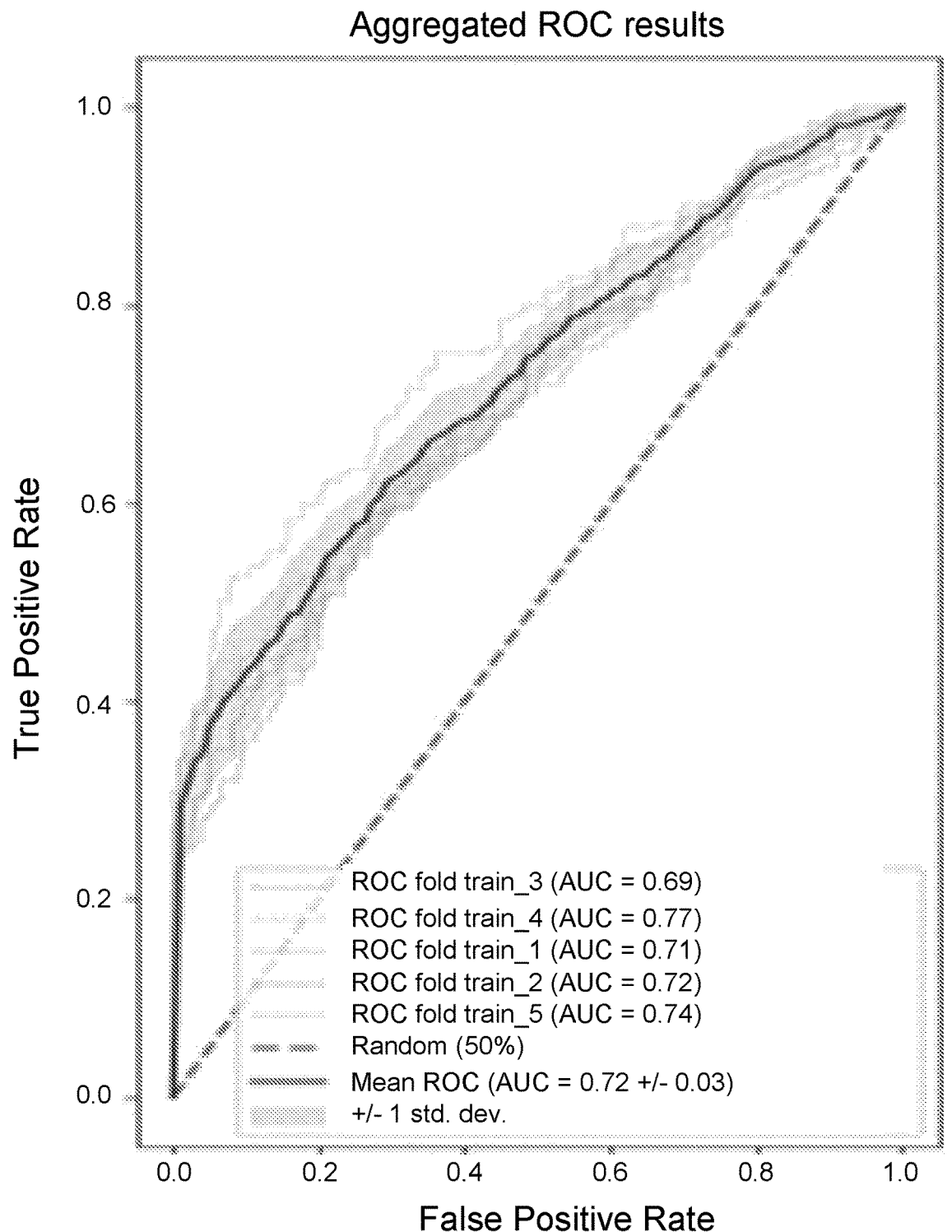
FIG. 6 illustrates the model performance, in the form of a receiver operating characteristic (ROC) curve, of a network architecture using a genotypic data construct for respective training subjects that includes cell-free nucleic acid data in the form of bin counts. For example, each respective bin counts is representative of a number of sequence reads in sequencing information measured from cell-free nucleic acid in biological samples obtained from the training subjects that maps onto a different region of the genome of the species represented by the respective bins for the training subjects, in which contribution from white blood cells to bin counts has not been masked, in accordance with an embodiment of the present disclosure. As shown here, the analysis was done with a 5-fold validation.
Figure 7:
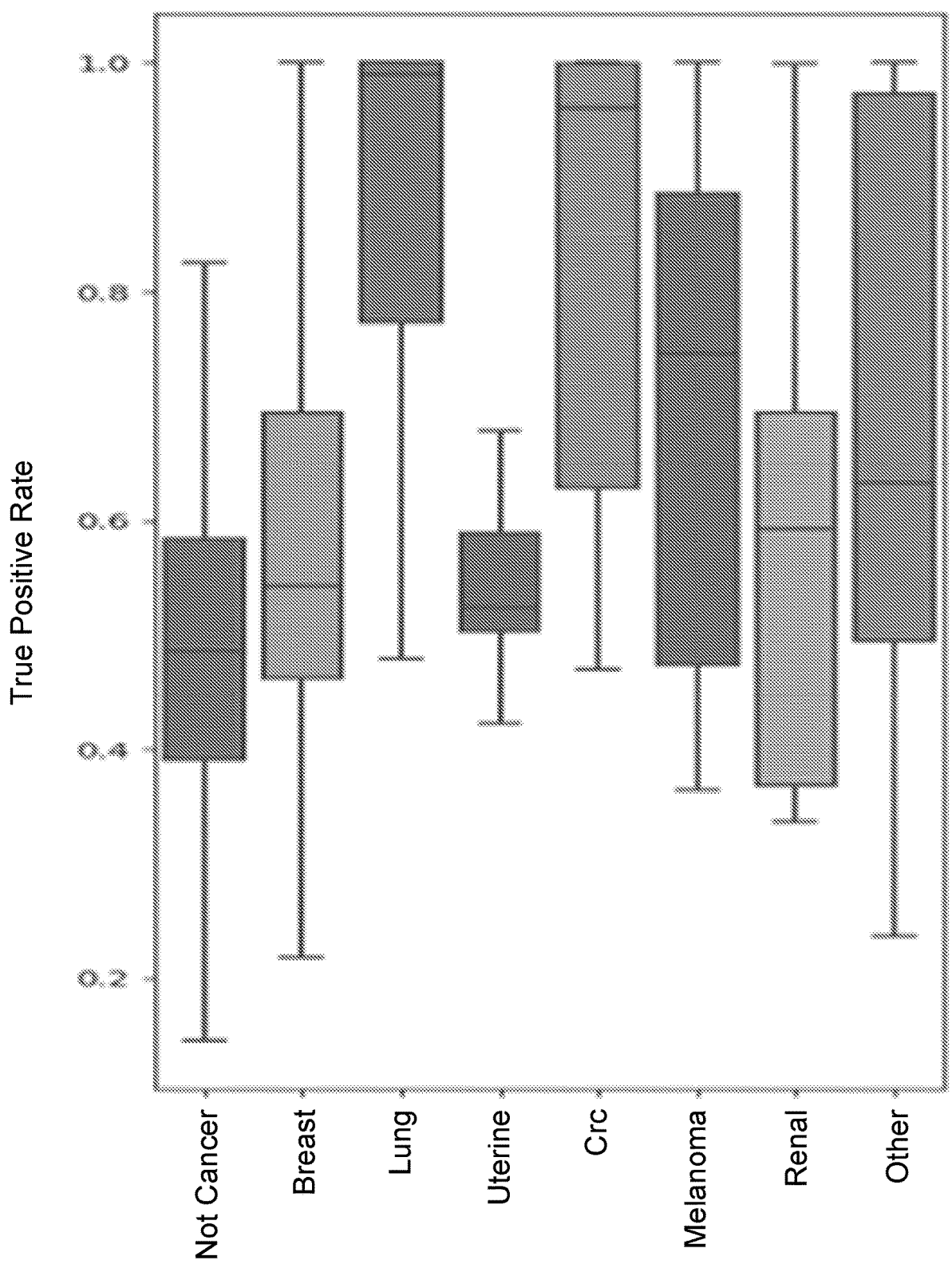
FIG. 7 illustrates the model performance of the model of FIG. 6, in the form of true positive rate as a function of tissue of origin, of a single track network architecture in accordance with an embodiment of the present disclosure.
Figure 8:
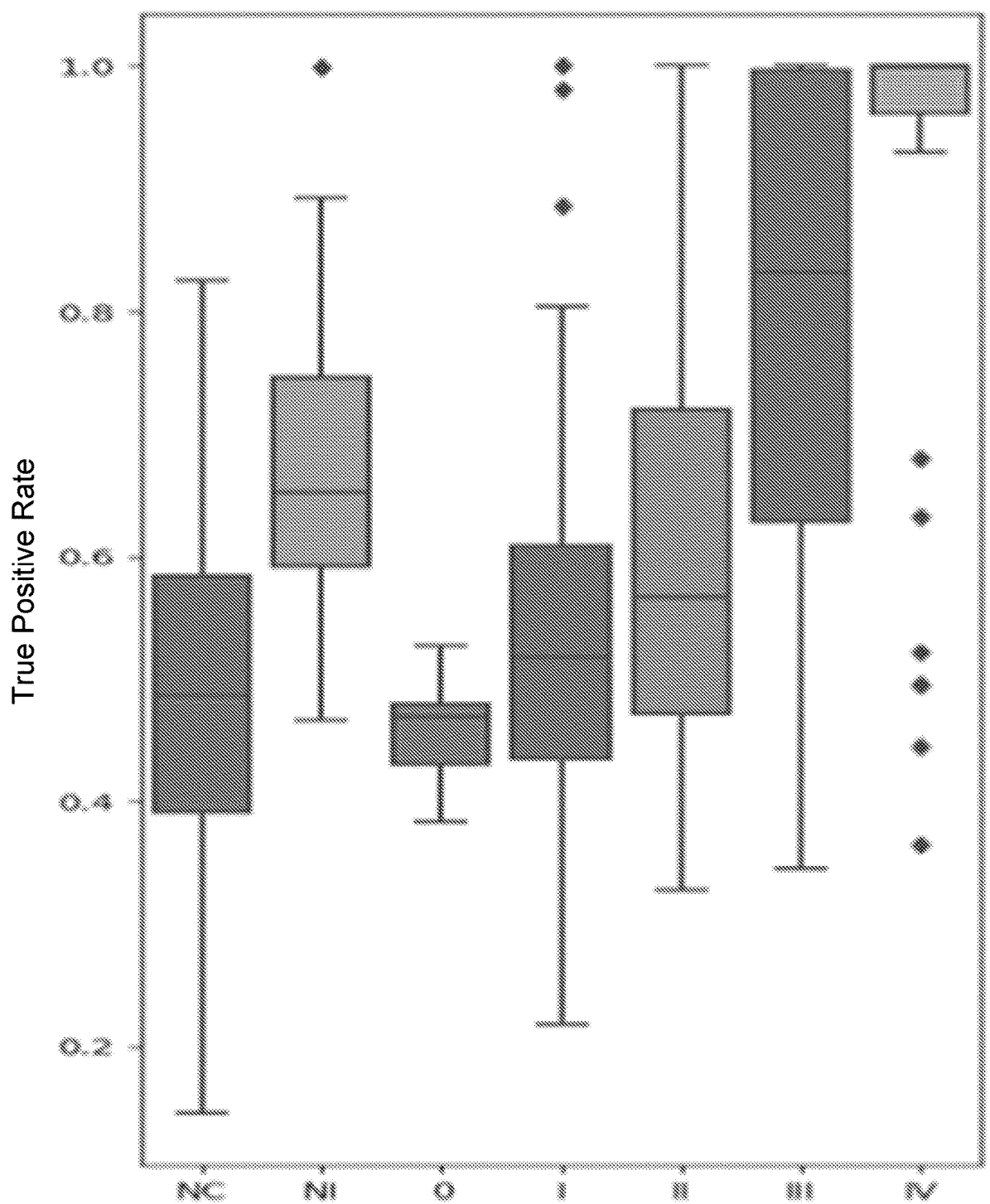
FIG. 8 illustrates the model performance of the model of FIG. 6, in the form of true positive rate as a function of cancer stage (all cancer types) in accordance with an embodiment of the present disclosure. NC: non-cancer; NI: non-informative; and O: other.

FIG. 6 illustrates the model performance, in the form of a receiver operating characteristic (ROC) curve of false positive rate versus true positive rate of the network architecture illustrated in FIG. 3 using a genotypic data construct 126 for each respective training subject in the training set. Each such genotypic data construct includes cell-free nucleic acid data in the form of single track bin counts representative of a number of sequence reads in sequencing information measured from cell-free nucleic acid in biological samples obtained from the training subjects that maps onto the different portions of the genome of the species represented by the respective bins for the training subjects. For these bin counts, contributions from white blood cells to bin counts has not been masked. Thus, FIG. 6 shows the ability of the network architecture 138 to determine the correct cancer type for each respective training subject in the training set. The ROC curve shows that the network architecture 138 described in FIG. 3 has a performance that is in line with the performance of a B-score based classifier. B-score based classifiers are described in U.S. patent application Ser. No. 16/352,739, entitled "Method and System for Selecting, Managing, and Analyzing Data of High Dimensionality," filed Mar. 13, 2019, which is hereby incorporated by reference. FIG. 7 illustrates the performance of the network architecture of FIG. 6 on a cancer type by cancer type basis. That is, in FIG. 7, the true positive rate of the network architecture 138 of FIG. 3 (in single track form) for all the training subjects in the training set that have breast cancer, lung cancer, uterine cancer, colorectal (Crc) cancer, a melanoma, renal cancer or other cancer (any of the other cancers in the CCGA training set), respectively, is provided on a cancer type by cancer type basis. FIG. 8 illustrates the performance of the network architecture of FIG. 6 on a cancer stage by cancer stage basis. That is, in FIG. 8, the true positive rate of the above-described network architecture 138 in determining the cancer type of training subjects in the training set as a function of undefined stage (NI), stage 0, stage 1, stage II, stage III, and stage IV cancer (regardless of cancer type) in the CCGA training set, is provided.

Figure 9:
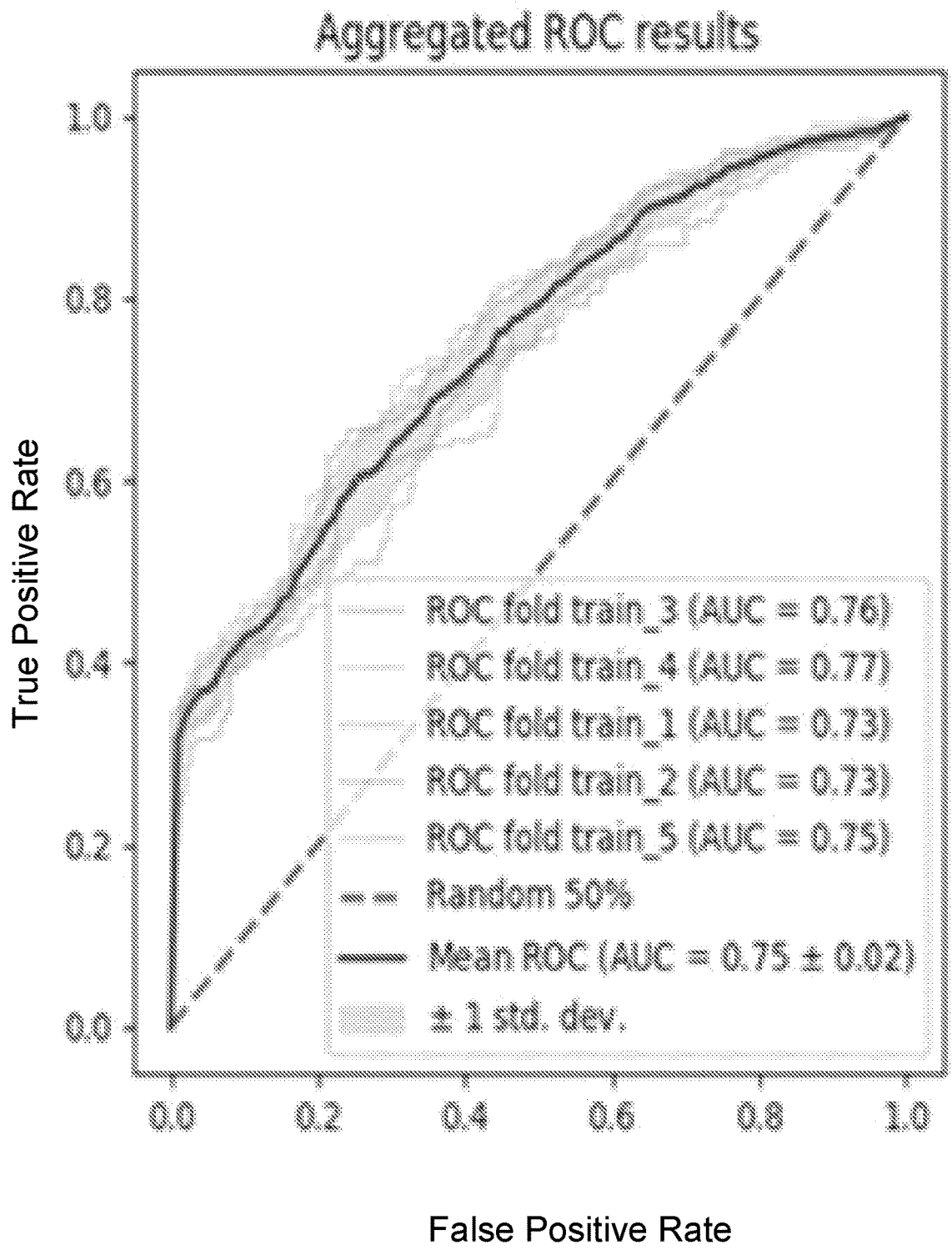
FIG. 9 illustrates example model performance, in the form of a receiver operating characteristic (ROC) curve of false positive rate versus true positive rate, of a network architecture using genotypic data constructs for training subjects that includes cell-free nucleic acid data in the form of single track bin counts. For example, each respective bin counts is representative of a number of sequence reads in sequencing information measured from cell-free nucleic acid in biological samples obtained from the training subjects that maps onto a different region of the genome of the species represented by the respective bin for the training subjects, in which contribution from white blood cells to bin count has been masked, for the training subjects in accordance with an embodiment of the present disclosure. As shown here, the analysis was done with a 5-fold validation.
Figure 10:
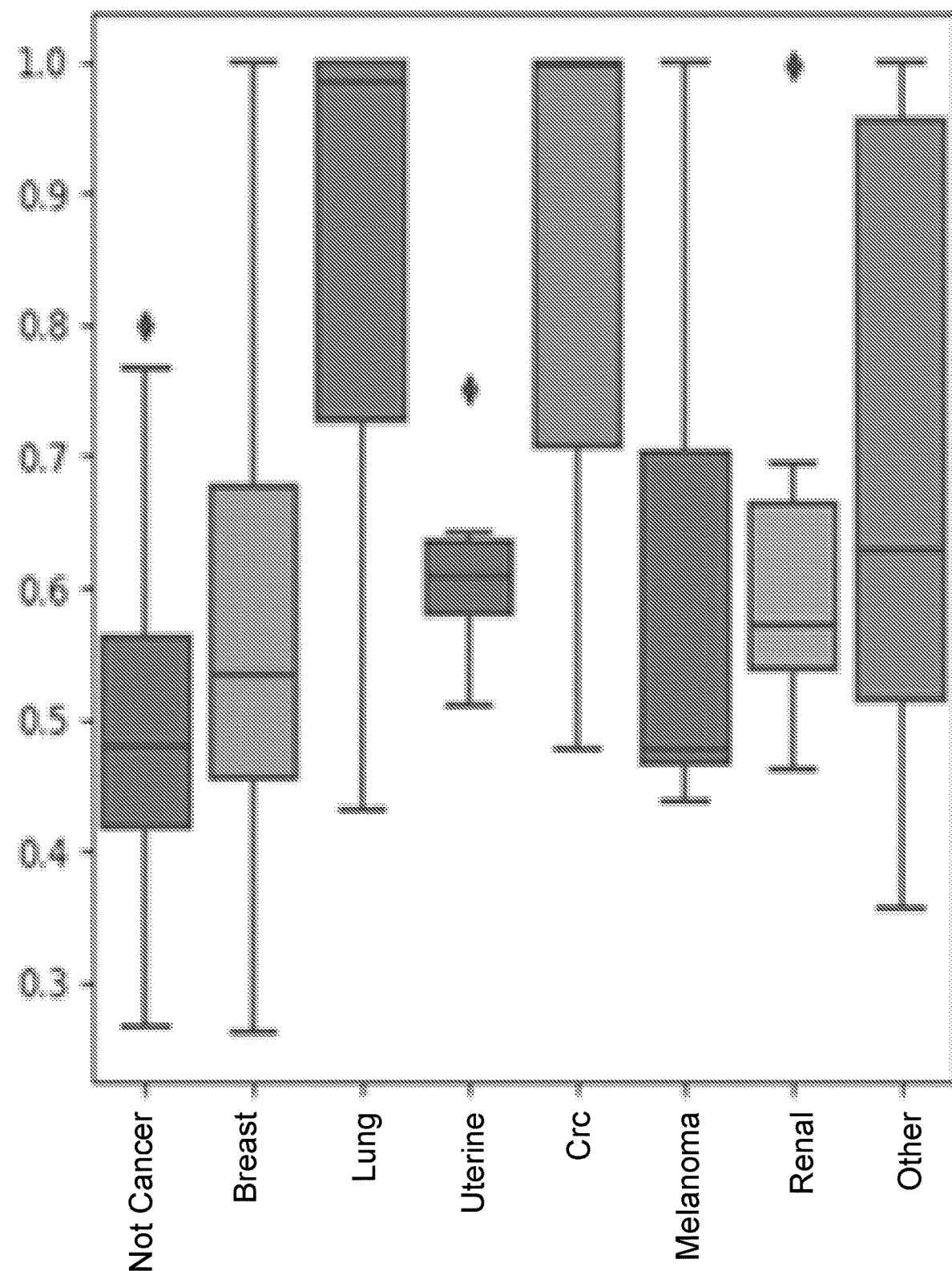
FIG. 10 illustrates example model performance of the model of FIG. 9, in the form of true positive rate as a function of tissue of origin, of a single track network architecture in accordance with an embodiment of the present disclosure.
Figure 11:
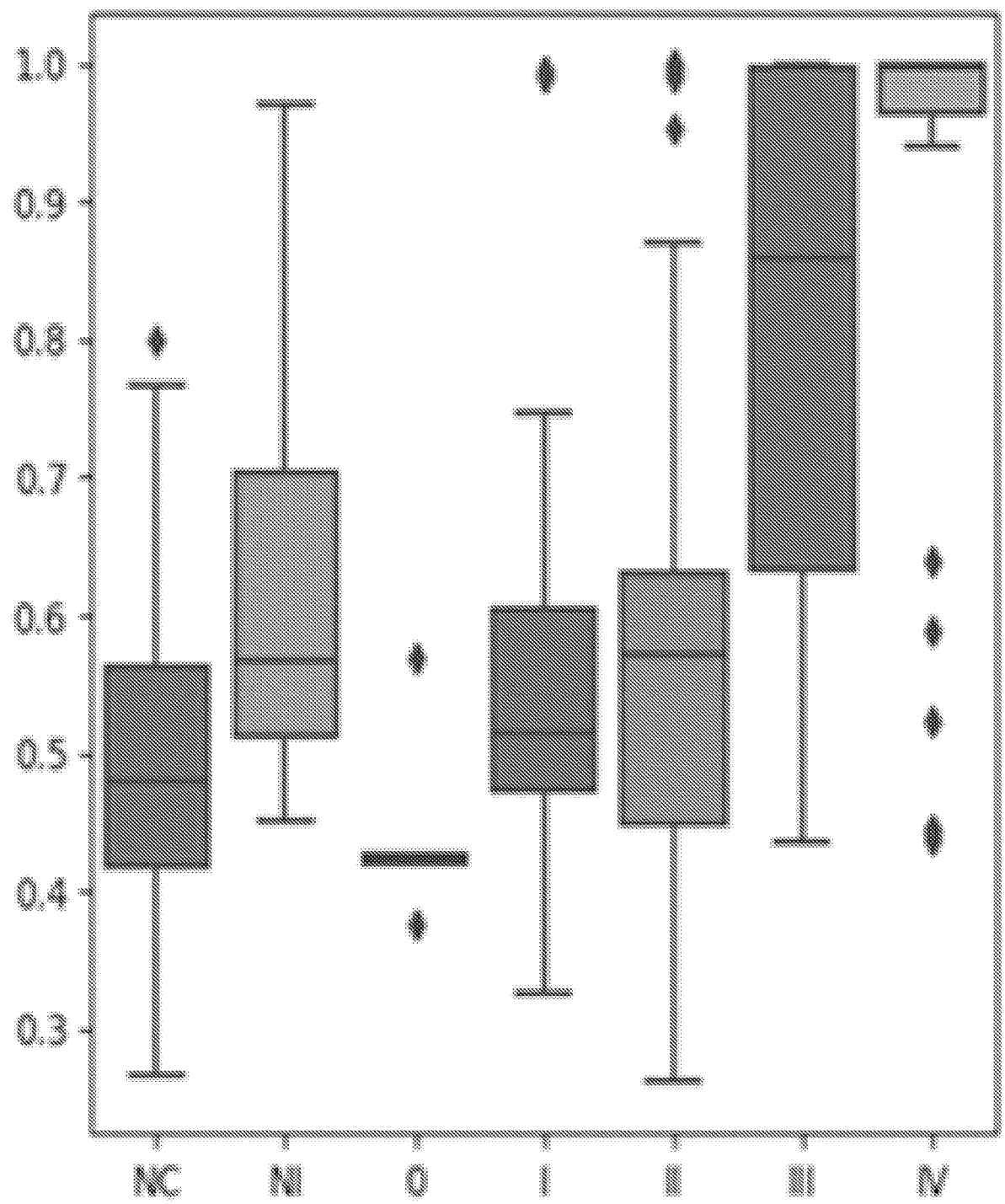
FIG. 11 illustrates example model performance of the model of FIG. 9, in the form of true positive rate as a function of cancer stage (all cancer types) in accordance with an embodiment of the present disclosure. NC: non-cancer; NI: non-informative; and O: other.

FIG. 9 illustrates the performance, in the form of an ROC curve of false positive rate versus true positive rate, of the network architecture of FIG. 3 in single track form (22 convolutional neural network paths) using genotypic data constructs for training subjects that includes cell-free nucleic acid data in the form of single track bin counts representative of a number of sequence reads in sequencing information measured from cell-free nucleic acid in biological samples obtained from the training subjects that maps onto the different portions of the genome of the species represented by the respective bins for the training subjects, in which contribution from white blood cells to bin count has been masked, for the training subjects. The ROC curve shows that masking the contribution from white blood cells to bin count improves baseline values observed in FIG. 6, where white blood cell contribution was not masked, by about three percent. FIG. 10 illustrates the performance of the network architecture of FIG. 9 on a cancer type by cancer type basis. That is, in FIG. 10, the true positive rate of the above-described network architecture used for FIG. 9, for all the training subjects in the training set that have breast cancer, lung cancer, uterine cancer, colorectal (Crc) cancer, a melanoma, renal cancer or other cancer (any of the other cancers in the CCGA training set), respectively, is provided on a cancer type by cancer type basis. FIG. 11 illustrates the performance of the network architecture of FIG. 9 on a cancer stage by cancer stage basis. That is, in FIG. 11, the true positive rate of the network architecture of FIG. 9 in determining the cancer type of training subjects in the training set as a function of undefined stage (NI), stage 0, stage 1, stage II, stage III, and stage IV cancer (regardless of cancer type) in the CCGA training set, is provided.

Figure 12:
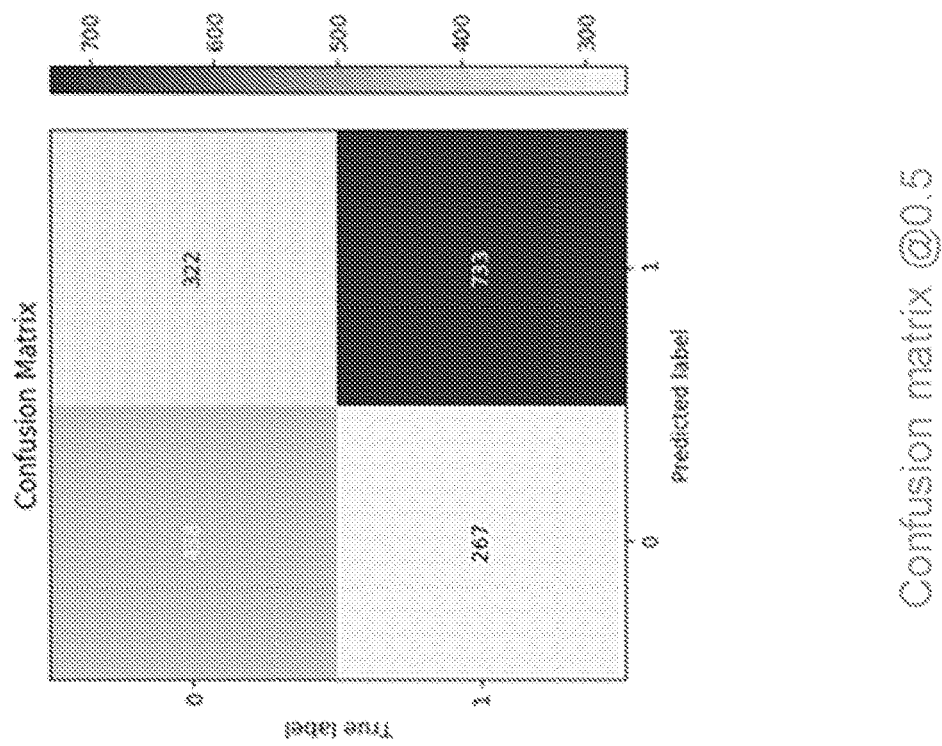
FIG. 12 illustrates example model performance of various track network architectures using a genotypic data construct for respective training subjects that includes cell-free nucleic acid data in the form of bin counts representative of a number of sequence reads in sequencing information measured from cell-free nucleic acid in biological samples obtained from the training subjects that maps onto the different regions of the genome of the species represented by the respective bins for the training subjects in accordance with an embodiment of the present disclosure.

FIG. 12 illustrates the model performance of various track network architectures using a genotypic data construct 126 for respective training subjects that includes cell-free nucleic acid data in the form of bin counts representative of a number of sequence reads in sequencing information measured from cell-free nucleic acid in biological samples obtained from the training subjects that maps onto the different region of the genome of the species represented by the respective bins for the training subjects. In particular, FIG. 12 shows the relative performance of masking of cell-free nucleic acid data from white blood cells (masking, no masking) and presenting cell-free nucleic acid data from white blood cell data as a separate track from cell-free nucleic acid data from cells other than white blood cells (double track in which there are 44 convolutional neural network paths) as opposed to simply not including white cell blood data (single track in which there are 44 convolutional neural network paths).

Figure 13:
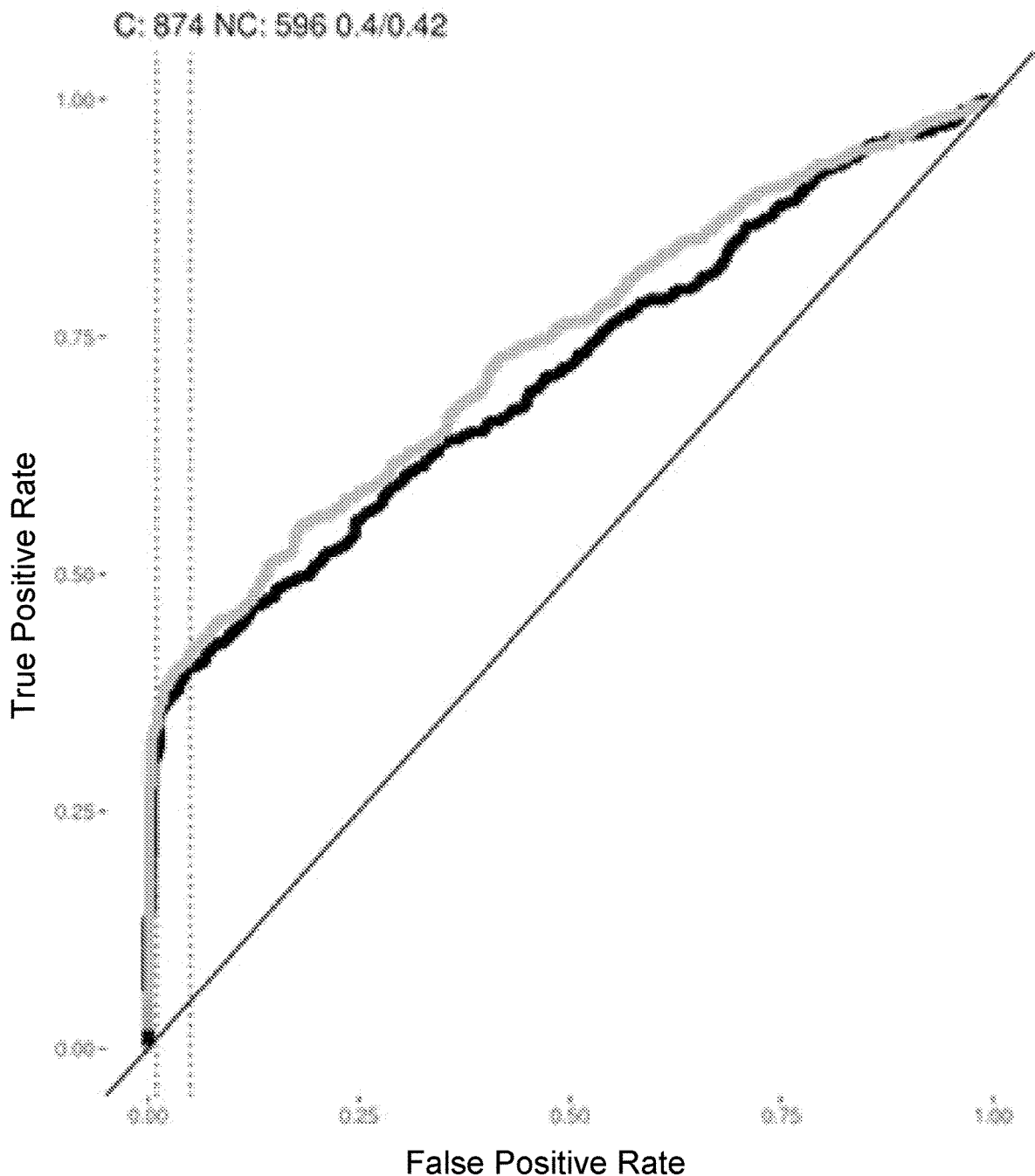
FIG. 13 shows head to head sample model performance, in the form of a ROC curves of the network architecture of FIG. 3 using a genotypic data construct for respective training subjects that includes cell-free nucleic acid data in the form of bin counts representative of a number of sequence reads in sequencing information measured from cell-free nucleic acid in biological samples obtained from the training subjects. Sequence reads for different bin counts map onto different regions of the genome of the species represented by the respective bins for the training subjects. In this example, contribution from white blood cells to bin score count has been masked (black line) and subject to neural network analysis and then compared with B-score analysis of the same training set (grey line), in accordance with an embodiment of the present disclosure.

FIG. 13 shows head to head model performance, in the form of ROC curves, of the network architecture of FIG. 3, in single track form using a genotypic data construct for respective training subjects that includes cell-free nucleic acid data in the form of bin counts representative of a number of sequence reads in sequencing information measured from cell-free nucleic acid in biological samples obtained from the training subjects that maps onto the different region of the genome of the species represented by the respective bins for the training subjects, in which contribution from white blood cells to bin score count has been masked (black line), to classification of the same training subject using a B-score classifier (grey line). Classification based on B-score classifiers is described in U.S. patent application Ser. No. 16/352,739, entitled "Method and System for Selecting, Managing, and Analyzing Data of High Dimensionality," filed Mar. 13, 2019, which is hereby incorporated by reference. FIG. 13 is across all 1764 subjects of the training set.

Figure 14:
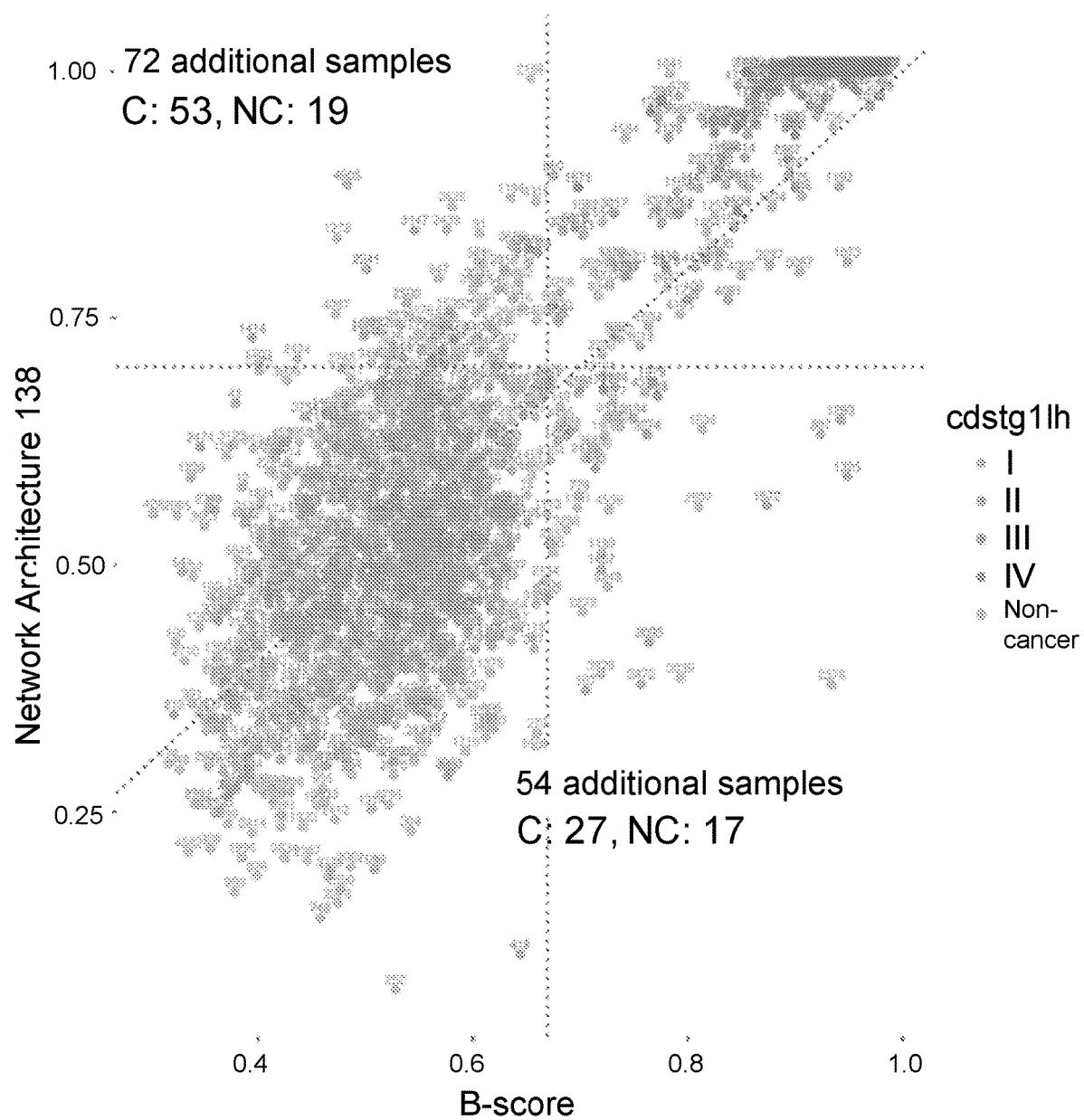
FIG. 14 illustrates a sample scatterplot comparison of the true positive rate as a function of cancer stage, across a training population of a convolutional network based network architecture versus a B-score classifier, in accordance with an embodiment of the present disclosure.

FIG. 14 illustrates a scatter plot comparison of the true positive rate as a function of cancer stage, across a training population of the convolutional network based network architecture of FIG. 3, in single track form, versus a B-score classifier. For FIG. 14, genotypic data constructs 126 for the respective training subjects that includes cell-free nucleic acid data in the form of bin counts representative of a number of sequence reads in sequencing information measured from cell-free nucleic acid in biological samples obtained from the training subjects that maps onto the region of the genome of the species represented by the respective bins for the training subjects, in which contribution from white blood cells to bin score count has been masked, is provided to the network architecture of FIG. 3 to evaluate the cancer type of these subjects. The performance of this network architecture under these conditions is compared to B-score analysis of the same training set of this Example. In FIG. 14, the data is broken out by cancer stage. FIG. 14 indicates that a classifier that combines B-score and the score from the network architecture 138 of FIG. 3 may be advantageous because the B-score classifies some subjects correctly that the network architecture 138 did not classify correctly and vice versa.

Figure 15:
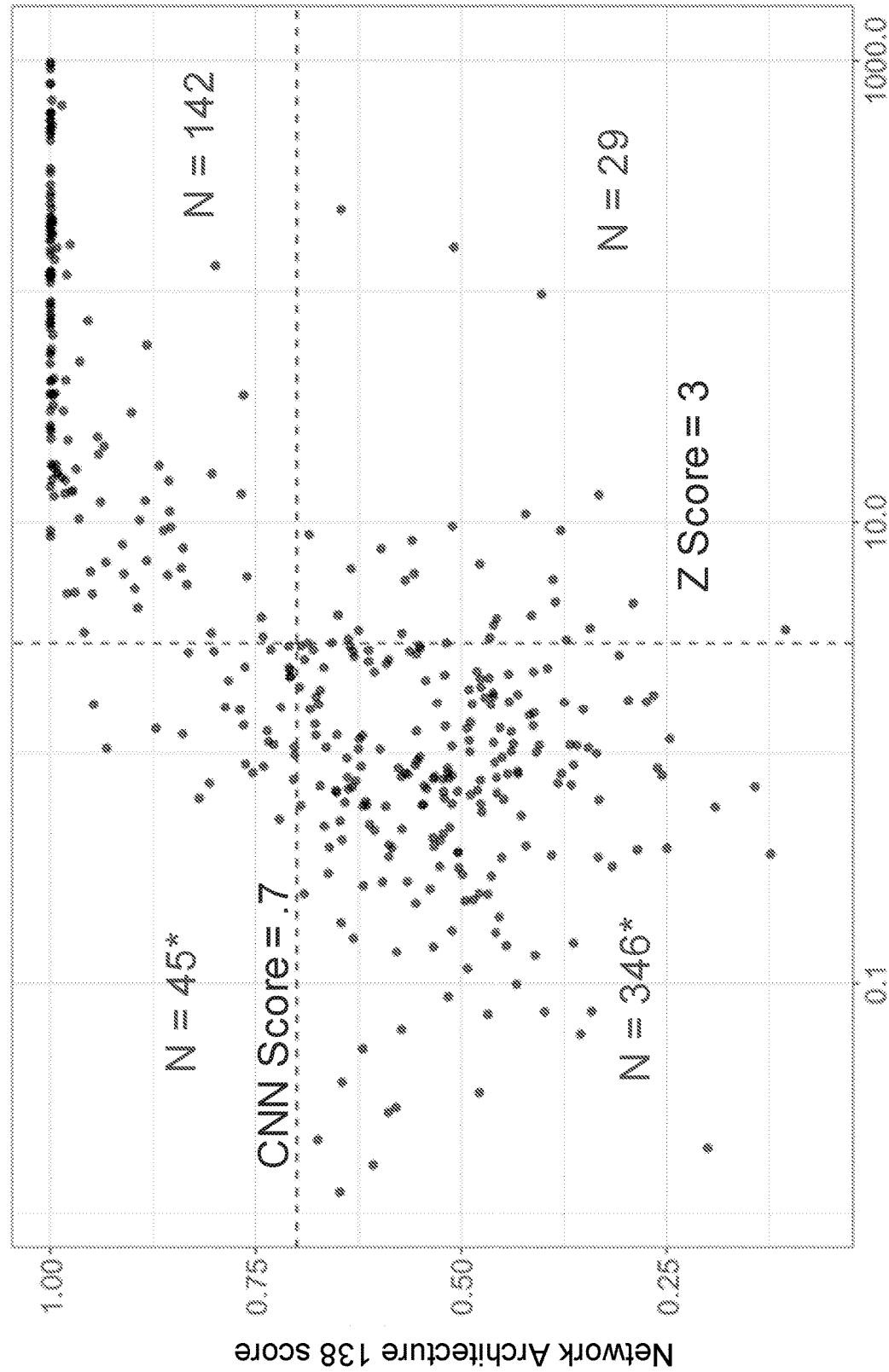
FIG. 15 illustrates how sample model performance of a network architecture, using a genotypic data construct for respective training subjects that includes cell-free nucleic acid data in the form of bin counts for the training subjects, correlates with the number of somatic copy number alterations (SCNAs) in such training subjects in accordance with an embodiment of the present disclosure.

FIG. 15 illustrates how the model performance of a network architecture, using a genotypic data construct for respective training subjects that includes cell-free nucleic acid data in the form of bin counts for the training subjects, correlates with the number of somatic copy number alterations (SCNAs) in such training subjects. See, for example, United States Patent Publication Number 2014/0100121, filed as application Ser. No. 13/801,748 on Mar. 13, 2013, which is hereby incorporated by reference, for disclosure on determining somatic copy number alteration count.

Figure 16:
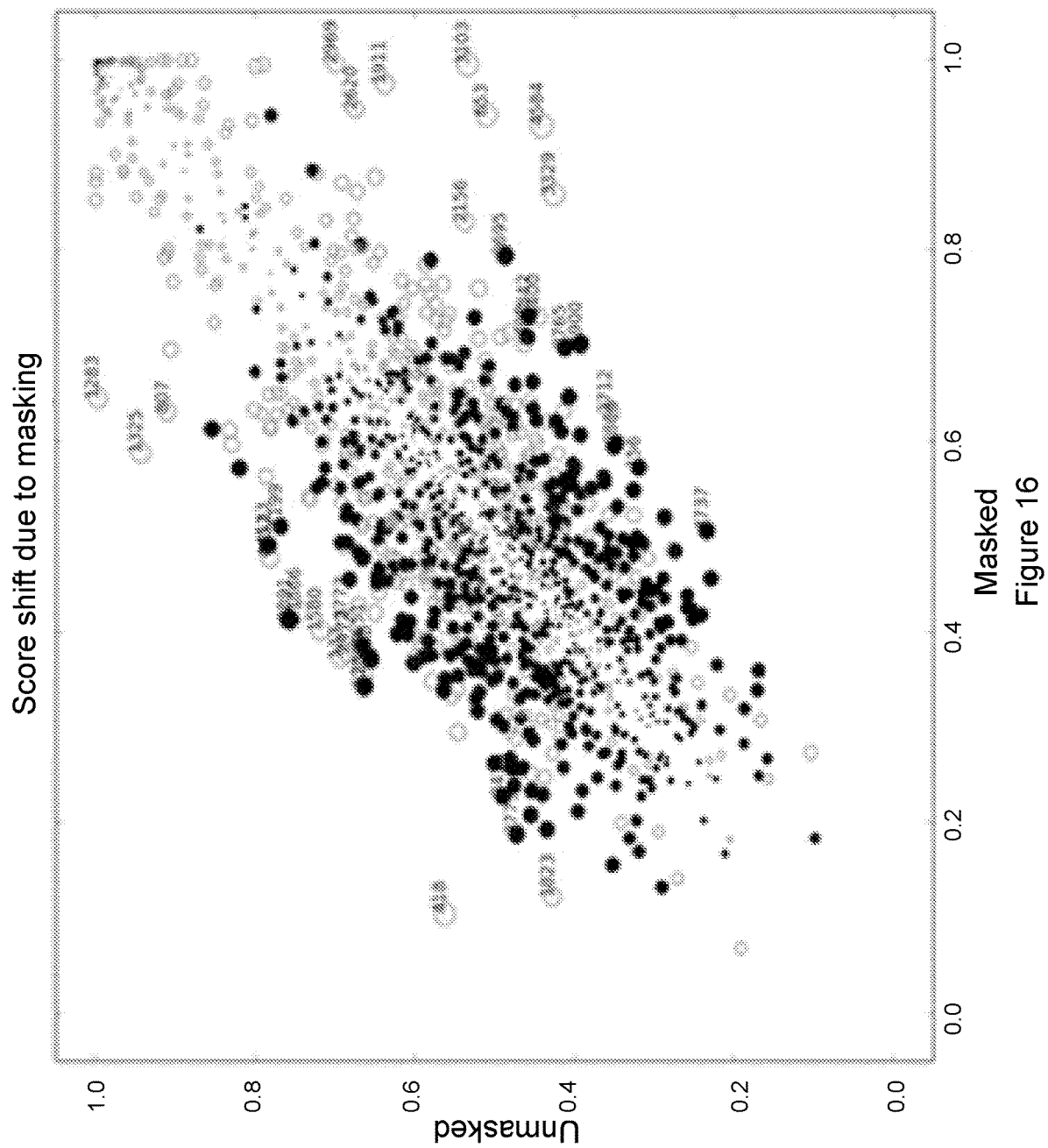

FIGS. 16 and 17 illustrate how the model performance of the network architecture 138, using a genotypic data construct 126 for respective training subjects that includes cell-free nucleic acid data in the form of single track bin counts representative of a number of sequence reads in sequencing information measured from cell-free nucleic acid in biological samples obtained from the training subjects that maps onto the different region of the genome of the species represented by the respective bins, for the training subjects in the training set, is affected by masking contribution from white blood cells to bin count, on a training subject by training subject basis. FIG. 16 illustrates that masking causes the network architecture 138 score to shift in the correct direction (black circles) fifty-seven percent of the time. FIG. 17 shows the top eight most dramatic shifts in the training set.

Figure 18:
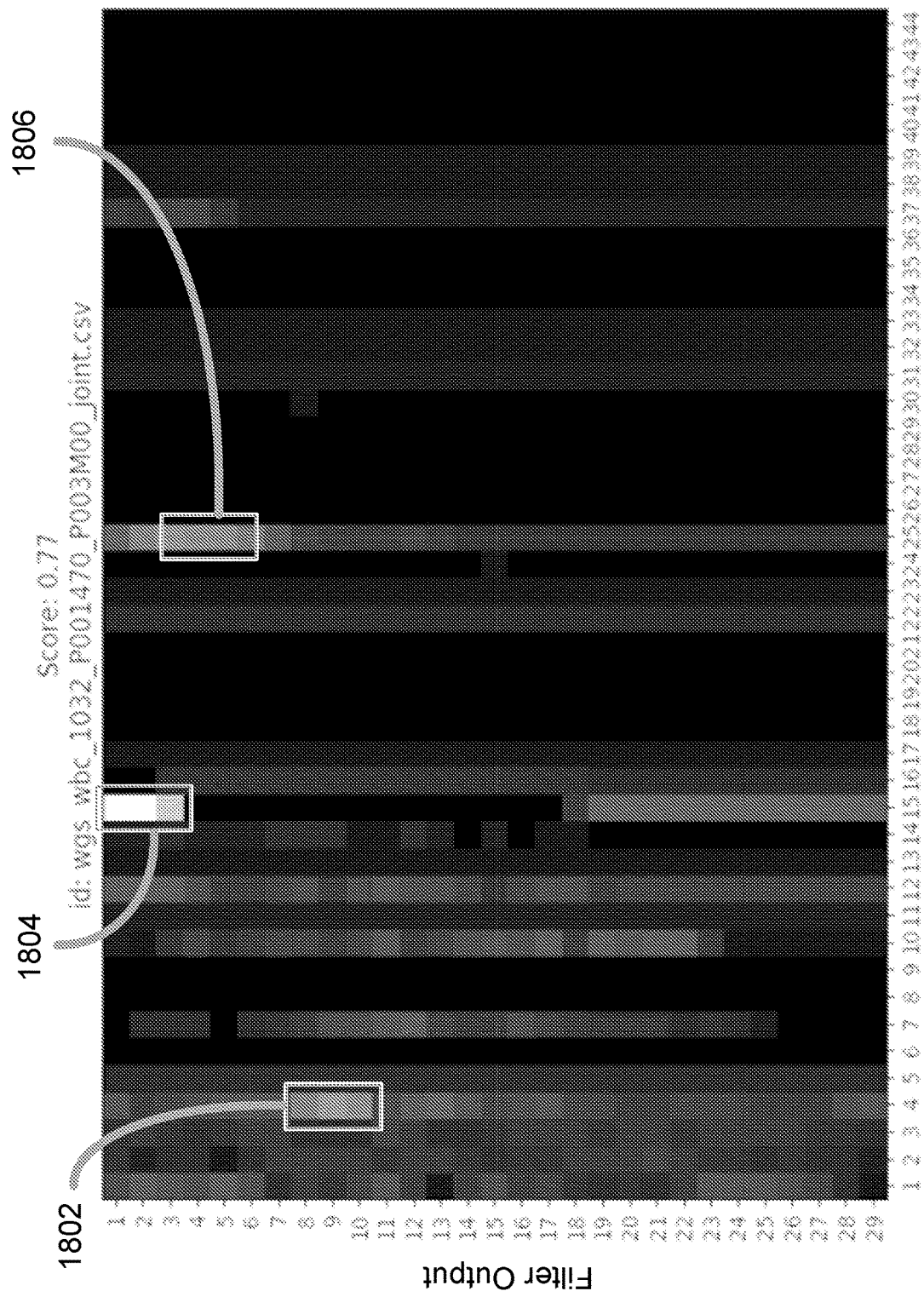
FIGS. 18 and 19 illustrate how a network architecture of the present disclosure is able to discern somatic deletions in a particular in accordance with an embodiment of the present disclosure.
Figure 19:
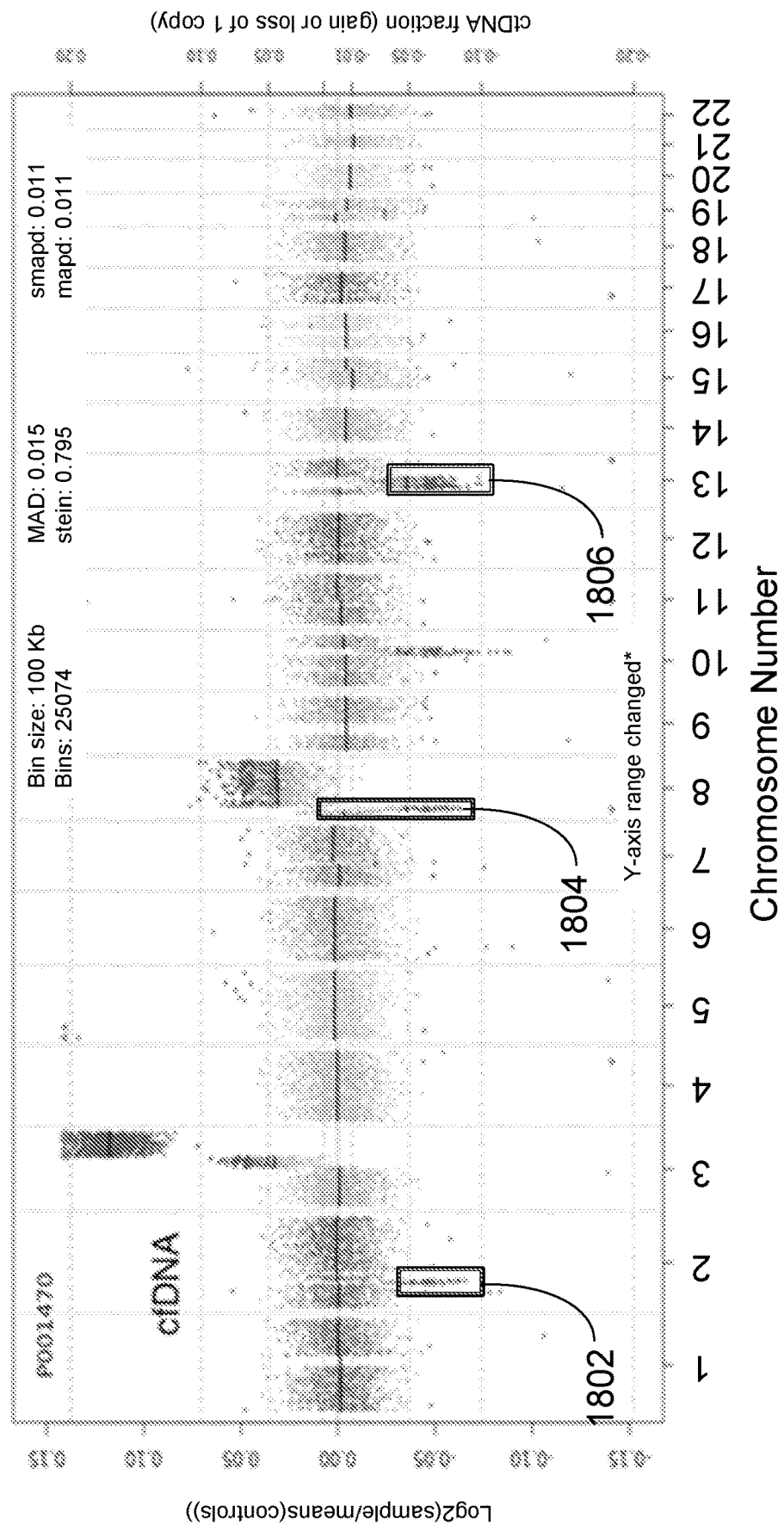

FIGS. 18 and 19 illustrate how the network architecture 138 of FIG. 3 is able to discern somatic deletions in a particular subject in accordance with an embodiment of the present disclosure. More particularly, FIG. 18 illustrates running the network architecture 138 in single track mode, where the respective output from the second pooling layer 308 in each convolutional neural network path 140 of the 22 convolutional neural network paths 140 (one for each chromosome) in the network architecture 138 illustrated in FIG. 3 is provided. That is, the output of the pooling layer 308 of the 22 convolutional neural network paths 140 is provided FIG. 18. Thus, in FIG. 18, there are two columns for each convolutional neural network path. The first column for a respective chromosome is the output of the pooling layer 308 as it pertains to pooling against the output from the first filter of the pooling layer 308 of the convolutional neural network path associated with the respective chromosome. The second column for a respective chromosome is the output of the pooling layer 308 as it pertains to pooling against the output from the second filter of the pooling layer 308 of the convolutional neural network path associated with the respective chromosome. As illustrated in FIG. 18, each column includes 29 elements, each element ranging in value where the range of values is grey-scaled between a low value (light color) and a high value (dark grey). FIG. 18 illustrates three regions (1802, 1804, 1806) for the convolutional neural network paths 140 corresponding to chromosomes 2, 8, and 13 where the outputs of the pooling layer is relatively low for the particular subject that forms the basis for the values presented in FIG. 18. Turning to FIG. 19, these three regions correlate with deletions on chromosomes 2, 8, and 13 of the training subject used for FIG. 18 as determined by reduced mean fragment length of paired sequence reads mapping to these chromosomes.

Figure 20:
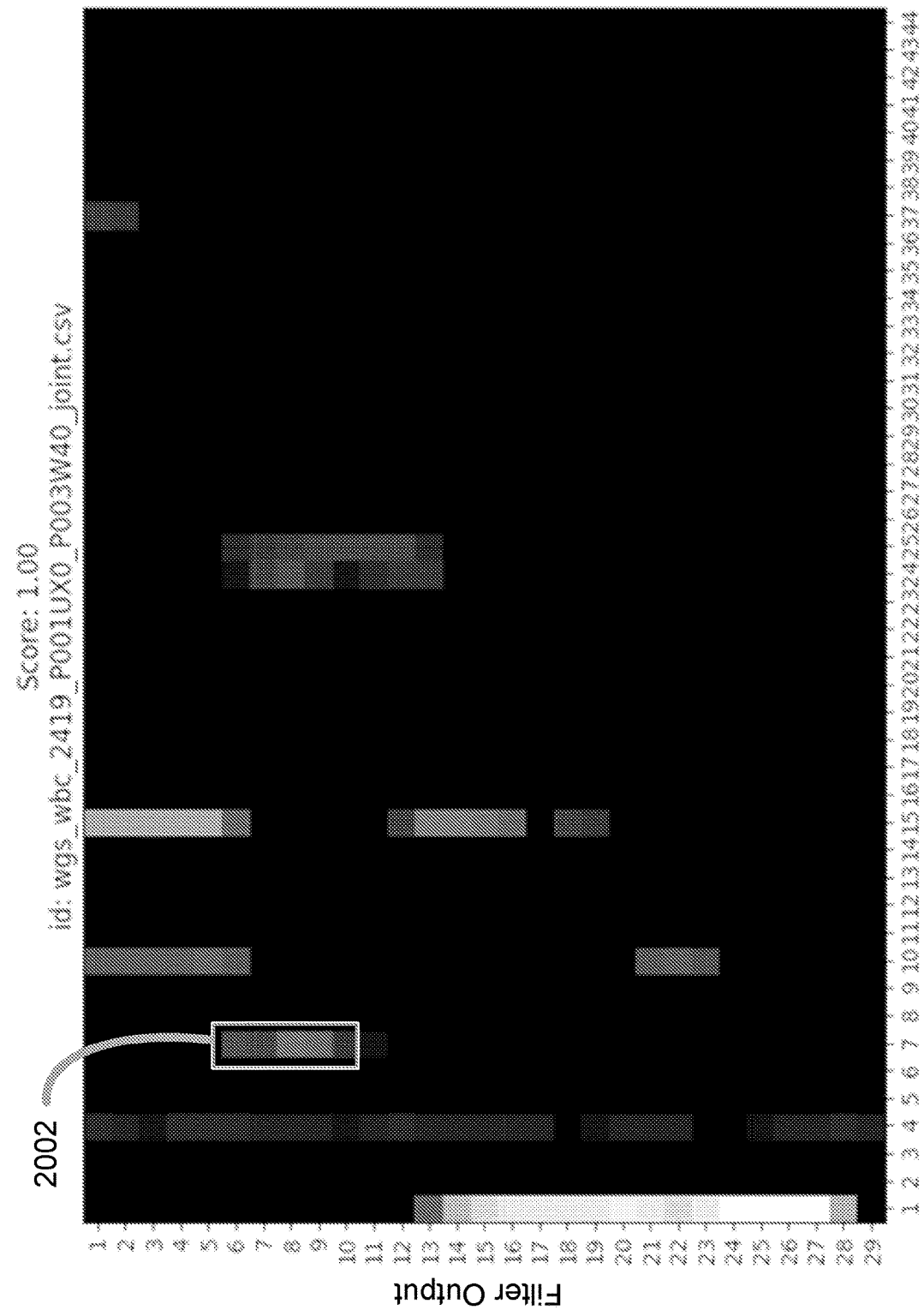
FIGS. 20 and 21 illustrate how a sample network architecture of the present disclosure is able to discern somatic copy number alterations (SCNAs) in a particular subject in accordance with an embodiment of the present disclosure.
Figure 21:
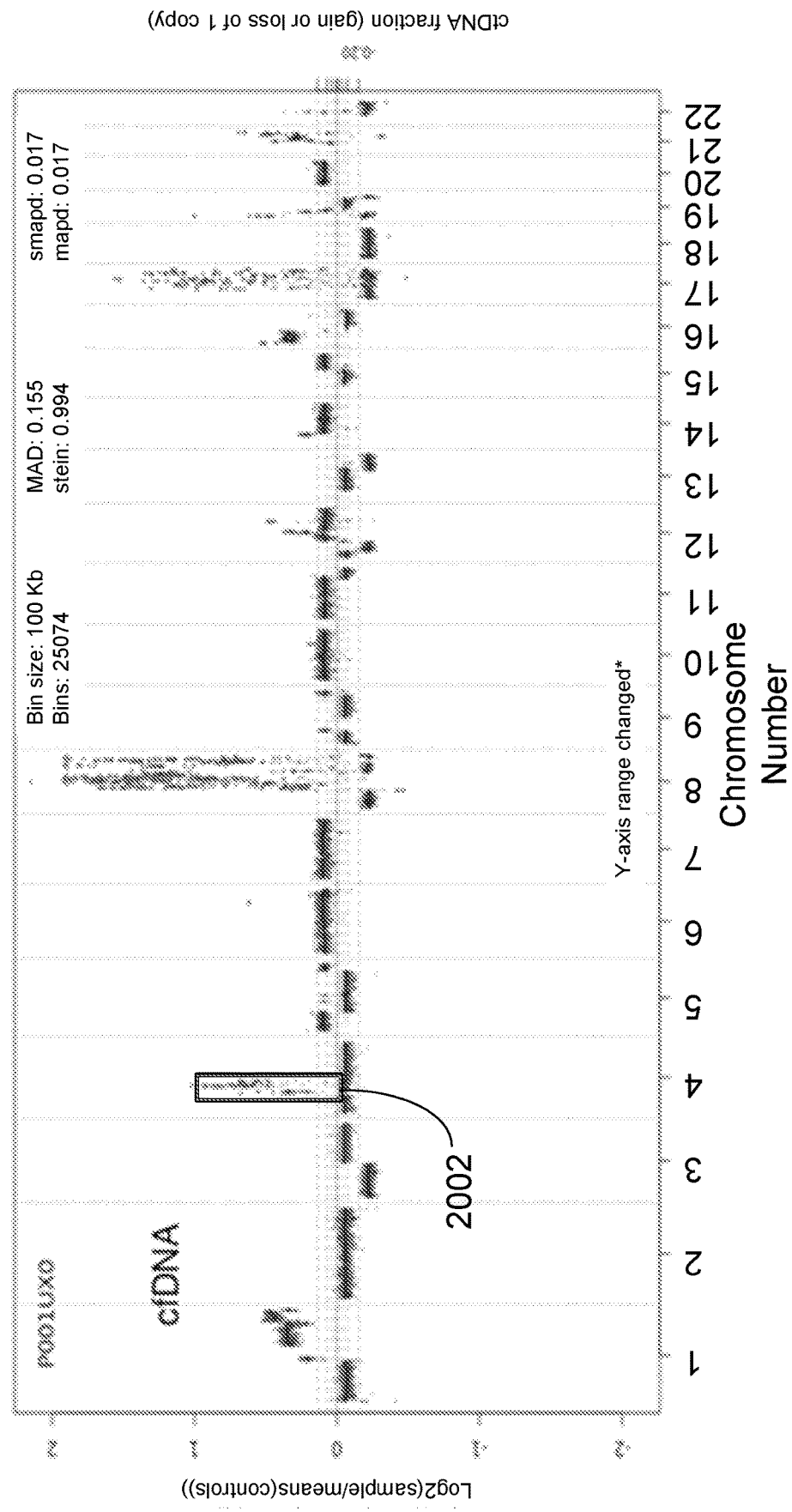

FIGS. 20 and 21 illustrate how the network architecture 138 of FIG. 3 is able to discern somatic copy number alterations in a particular subject. See, for example, United States Patent Publication Number 2014/0100121, filed as application Ser. No. 13/801,748 on Mar. 13, 2013, which is hereby incorporated by reference, for disclosure on determining somatic copy number alteration count. More particularly, FIG. 20 illustrates running the network architecture 138 in single track mode, where the respective output from the second pooling layer 308 in each convolutional neural network path 140 of the 22 convolutional neural network paths 140 (one for each chromosome) in the network architecture 138 illustrated in FIG. 3 is provided. That is, the output of the pooling layer 308 of the 22 convolutional neural network paths 140 is provided FIG. 20. Thus, in FIG. 20, there are two columns for each convolutional neural network path 140. The first column for a respective chromosome is the output of the pooling layer 308 as it pertains to pooling against the output from the first filter of the pooling layer 308 of the convolutional neural network path associated with the respective chromosome. The second column for a respective chromosome is the output of the pooling layer 308 as it pertains to pooling against the output from the second filter of the pooling layer 308 of the convolutional neural network path associated with the respective chromosome. As illustrated in FIG. 20, each column includes 29 elements, each element ranging in value where the range of values is grey-scaled between a low value (light color) and a high value (dark grey). FIG. 20 illustrates a particular region (2020) for the convolutional neural network path 140 corresponding to chromosome 4 where the output of the pooling layer is relatively low for the particular subject that forms the basis for the values presented in FIG. 20. Turning to FIG. 21, this region correlates with significant somatic copy number alteration of a training subject as determined by an increased number of sequence reads mapping to chromosome 4.

Example 5: Convolutional Neural Network for Cancer Classification Performance

Referring to FIGS. 5 and 27-40, an example for classifying a cancer condition, in a plurality of different cancer conditions, for humans is provided. In this example, the performance of the classifier illustrated in FIG. 3 and described in further detail in Example 6 below was evaluated. In FIGS. 27-41, the scorer 152 outputs a binary classification (k=2), where one of the two outputs is for the designation "cancer" and the other of the two outputs is for the designation "non-cancer." Moreover, the scores of "cancer" and "non-cancer" sum up to one in this Example. Thus, the "CNN score" in FIGS. 27-41 is the score for the "Cancer class" (also referred to as the positive class score).

Figure 27:
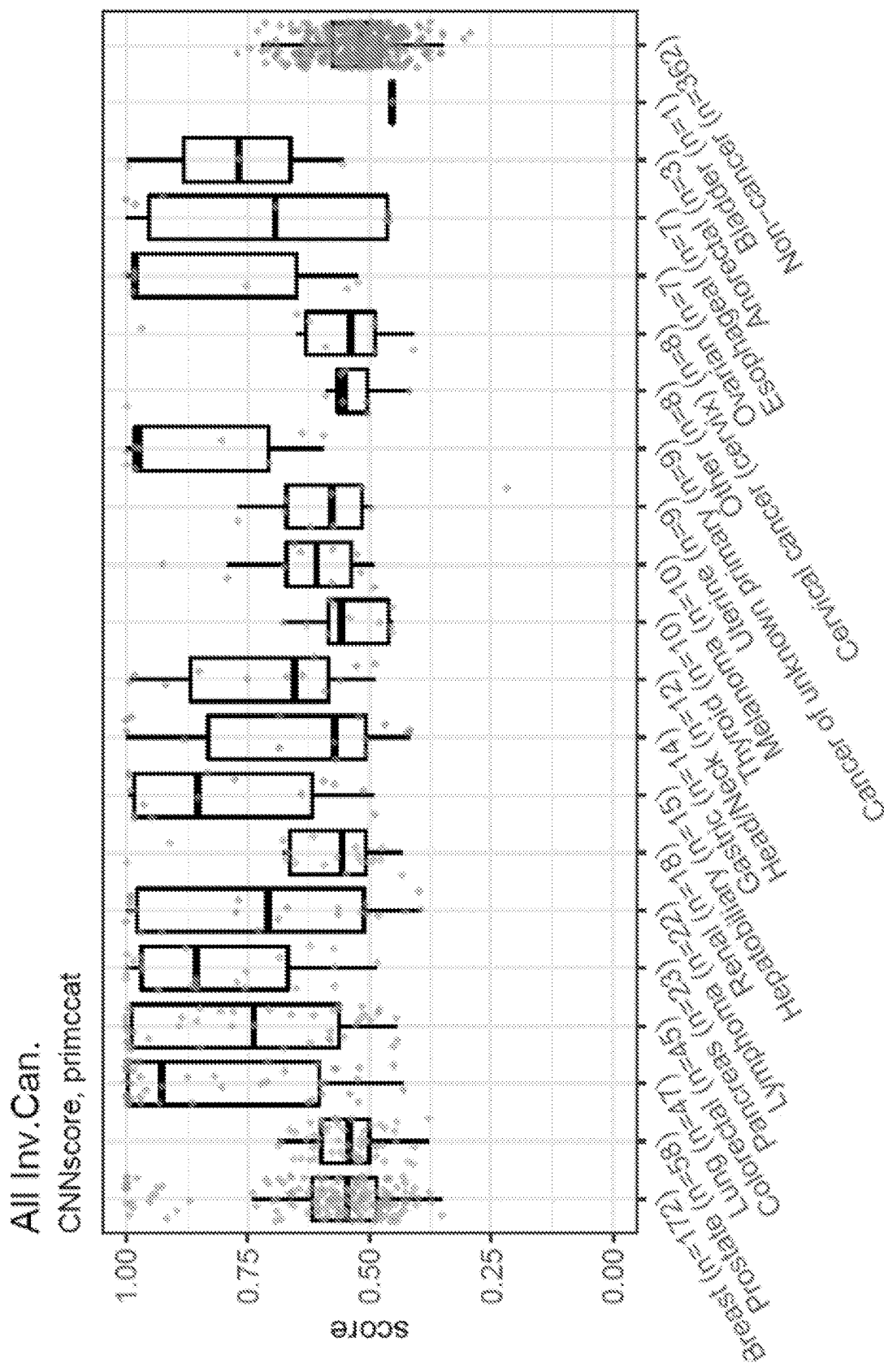
FIG. 27 illustrates a sample boxplot of the convolutional network architecture scores of the instant disclosure for cancer type classification broken out by cancer type and specifying the number of training subjects in each cancer type were used in accordance with an embodiment of the present disclosure.

FIG. 27 illustrates a boxplot of the convolutional network architecture scores of the instant disclosure for cancer type classification broken out by cancer type and specifying the number of training subjects in each cancer type that were used in accordance with an embodiment of the present disclosure. For FIG. 27, the scorer 152 returned score values for both "cancer" (positive class score) and "non-cancer" for each subject in the population. These two score values sum to one. Thus, for example, what is shown in FIG. 27 for the breast cancer population is the positive class score (has cancer) that the scorer 152 of network architecture 138 gave for each of the 172 subjects that have breast cancer. Likewise, what is shown in FIG. 27 for the prostate population is the positive class score (has cancer) that the scorer 152 of network architecture 138 gave for each of the 58 subjects that have prostate cancer.

Figure 28:
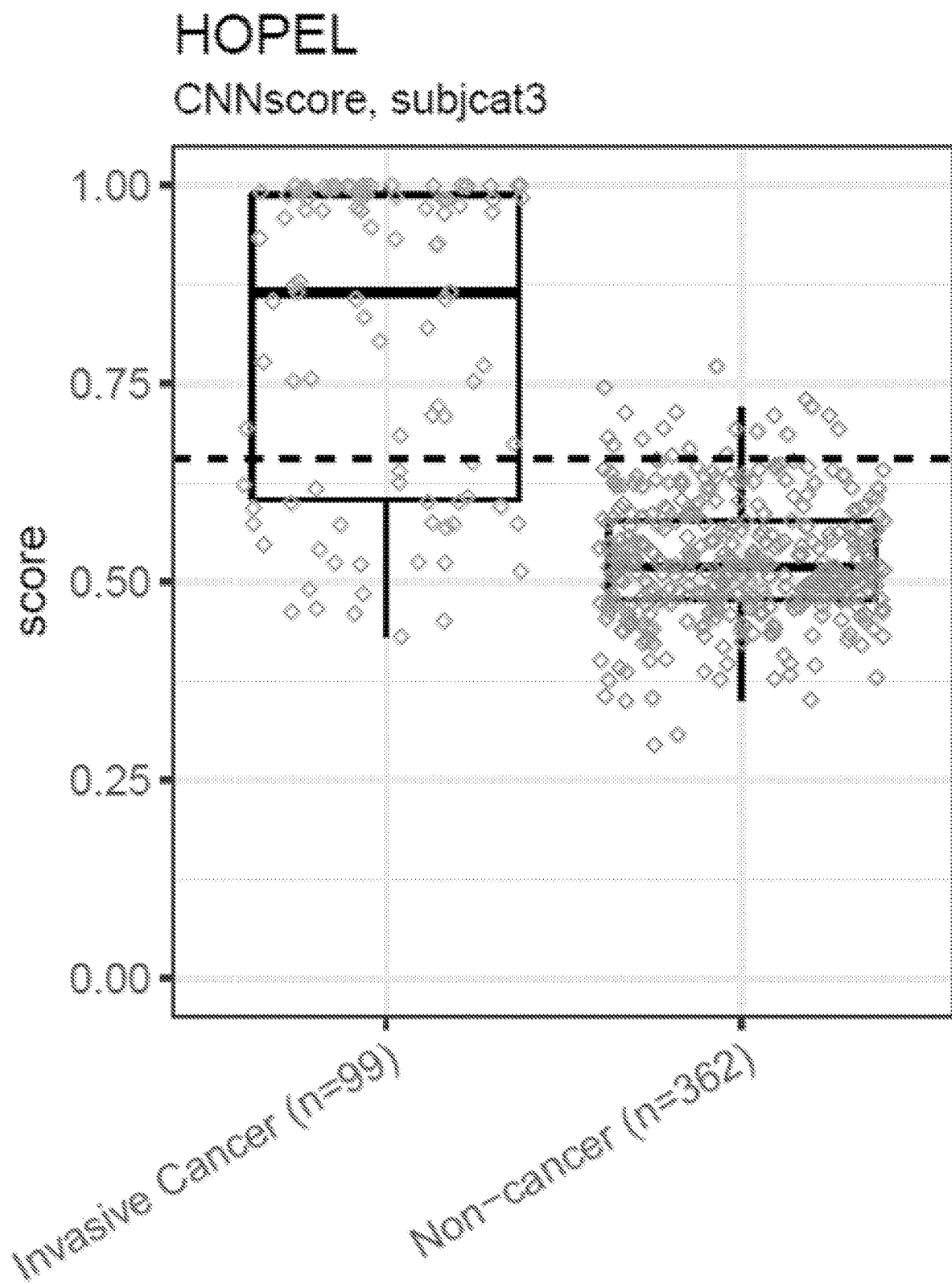
FIG. 28 illustrates sample convolutional network architecture scores of the instant disclosure for cancer type classification for the high mortality cancers: hepatobiliary, ovarian, pancreatic, esophageal, lung (HOPEL) by invasive cancer and non-cancer status in accordance with an embodiment of the present disclosure.
Figure 29:
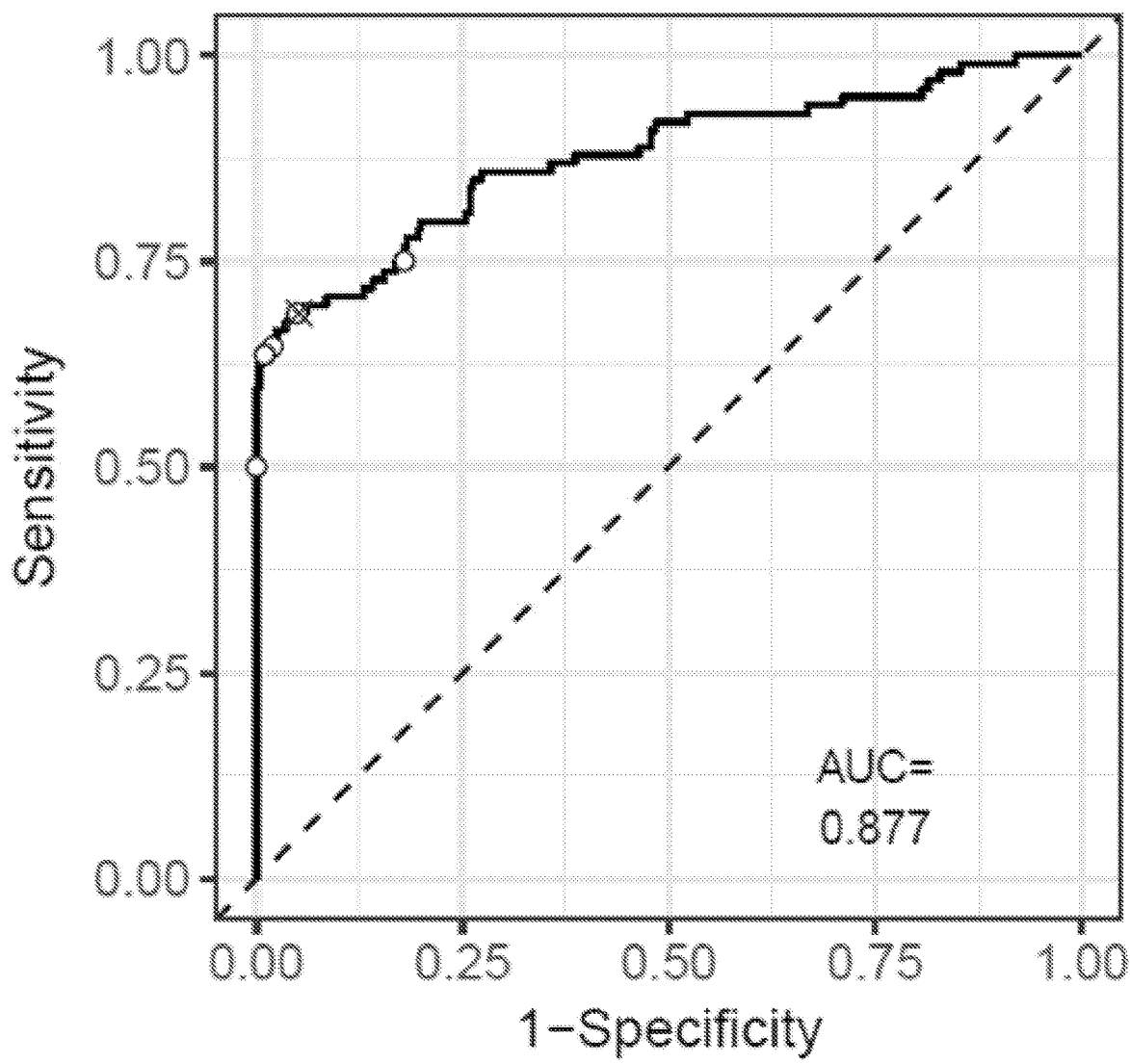
FIG. 29 illustrates a ROC for sample convolutional network architecture scores of the instant disclosure for HOPEL in accordance with an embodiment of the present disclosure.

FIG. 28 illustrates the convolutional network architecture 138 positive class scores "has cancer" for cancer type classification for the high mortality cancers: hepatobiliary, ovarian, pancreatic, esophageal, lung (HOPEL) by invasive cancer and non-cancer status. In FIG. 28, a total of 99 training subjects have high mortality cancer and a total of 362 training subjects that do not have high mortality cancer are evaluated. For FIG. 28, the scorer 152 returned score values for both "cancer" (positive class score) and "non-cancer" for each subject in the population tested. These two score values sum to one. Thus, for example, what is shown in FIG. 28 is the positive class score (has cancer) that the scorer 152 of network architecture 138 gave for each of the 99 subjects that have a HOPEL cancer. What is also shown in FIG. 28 is the positive class score (has cancer) that the scorer 152 of network architecture 138 gave for each of the 362 subjects that do not have a HOPEL cancer. The positive class score provided by the network architecture for the subjects that do not have a HOPEL cancer is lower than the positive class score for the subjects that do have a HOPEL cancer, indicating that the network architecture is able to discriminate between HOPEL cancer and not having HOPEL cancer. FIG. 29 illustrates a ROC for the convolutional network architecture 138 scores for the data of FIG. 28.

Figure 30:
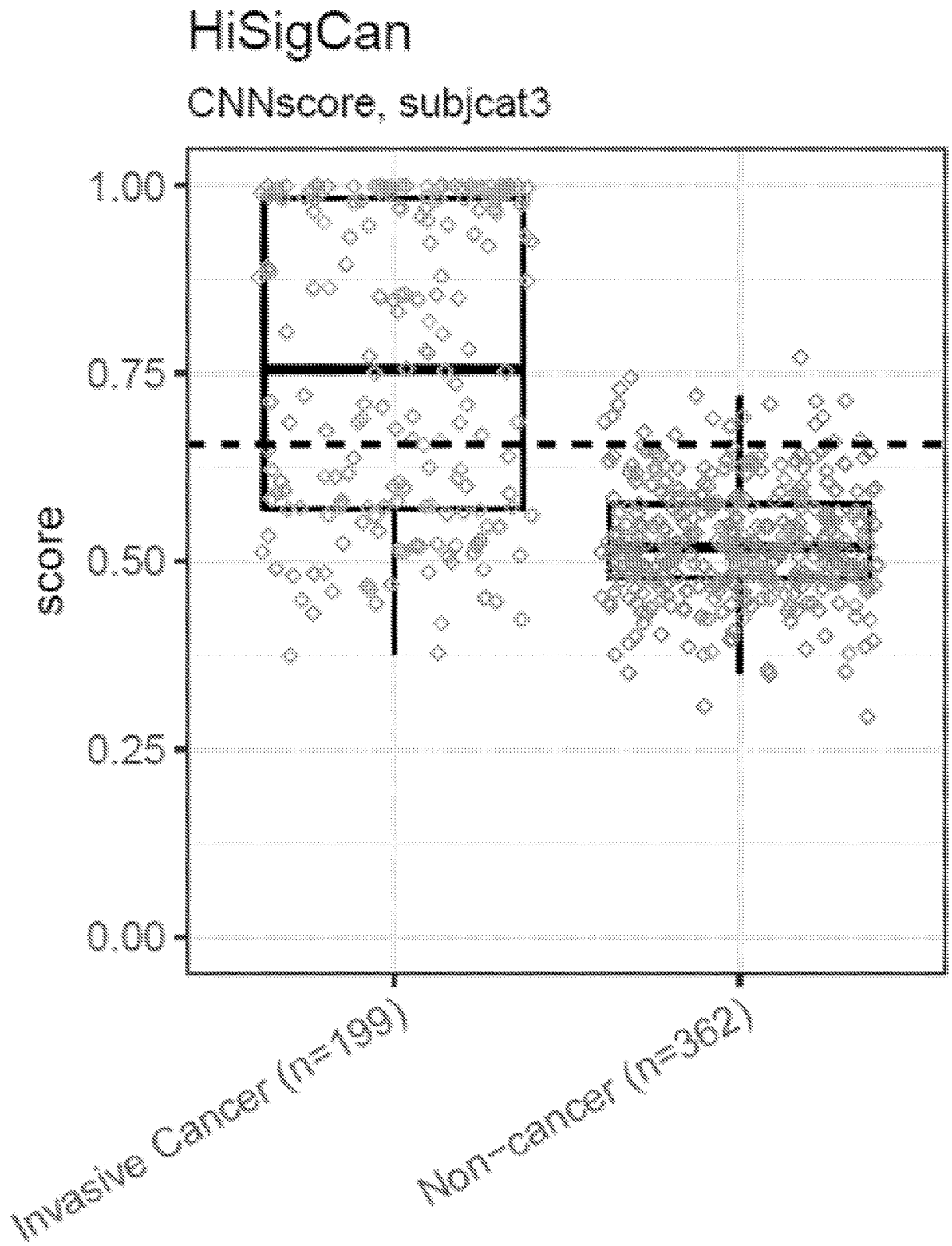
FIG. 30 illustrates sample convolutional network architecture scores of the instant disclosure for high signal cancers (HiSigCan), which are defined as single primary invasive cancer of: ER– breast, colorectal, lung, pancreatic, ovarian, hepatobiliary, gastric, head and neck, and esophageal cancer, in accordance with an embodiment of the present disclosure.
Figure 31:
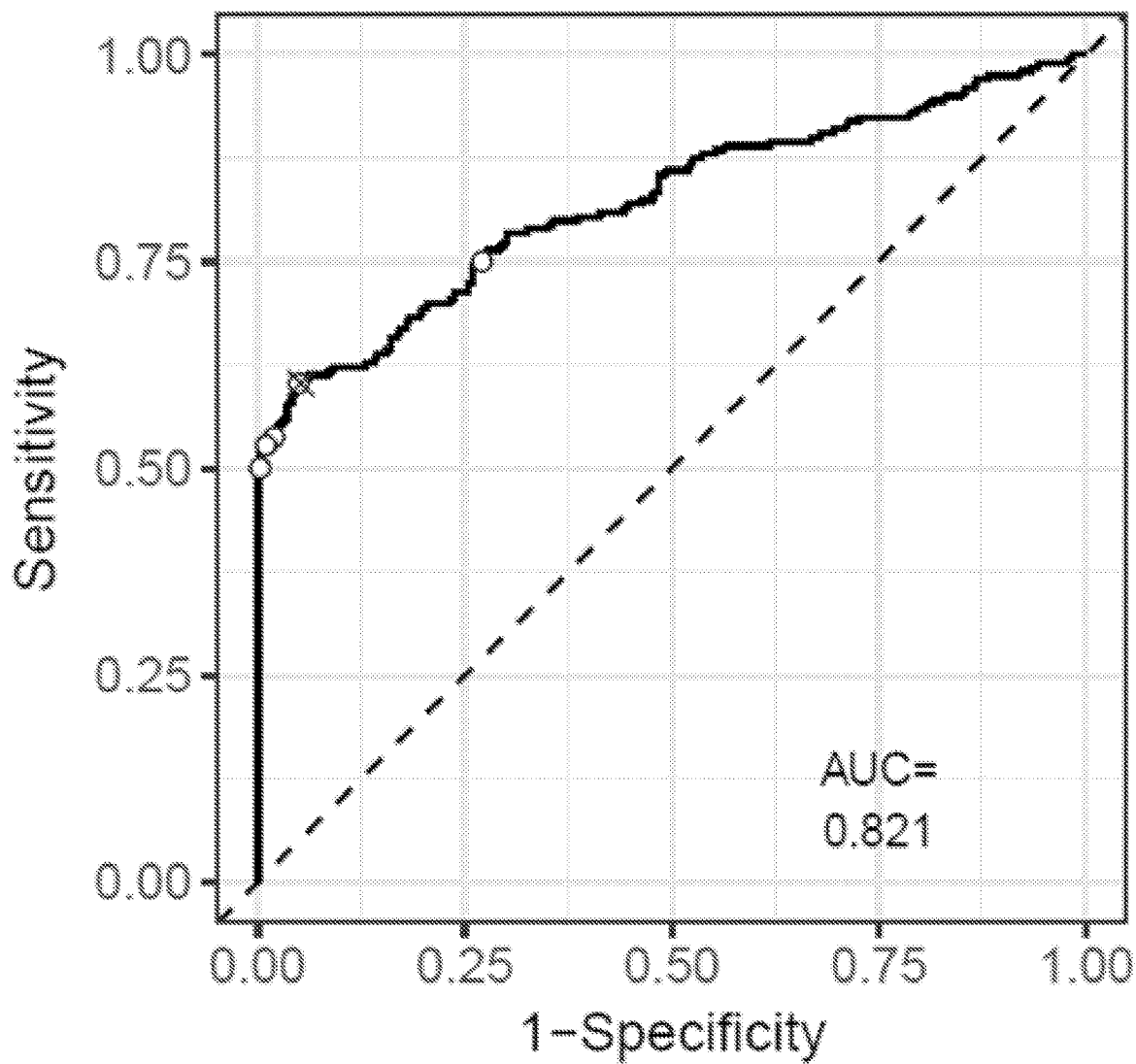
FIG. 31 illustrates a ROC for sample convolutional network architecture scores of the instant disclosure for HiSigCan in accordance with an embodiment of the present disclosure.

FIG. 30 illustrates the convolutional network architecture 138 scores of the instant disclosure for high signal cancers (HiSigCan), which are defined as single primary invasive cancer of: ER− breast, colorectal, lung, pancreatic, ovarian, hepatobiliary, gastric, head and neck, and esophageal cancer. In FIG. 30, a total of 199 training subjects have high signal cancer and a total of 362 training subjects that do not have high signal cancer are evaluated. For FIG. 30, the scorer 152 returned score values for both "cancer" (positive class score) and "non-cancer" for each subject in the population tested. These two score values sum to one. Thus, for example, what is shown in FIG. 30 is the positive class score (has cancer) that the scorer 152 of network architecture 138 gave for each of the 199 subjects that have a HiHigCan cancer. What is also shown in FIG. 30 is the positive class score (has cancer) that the scorer 152 of network architecture 138 gave for each of the 362 subjects that do not have a HiHigCan cancer. The positive class score provided by the network architecture for the subjects that do not have a HiHigCan cancer is lower than the positive class score for the subjects that do have a HiHigCan cancer, indicating that the network architecture 138 is able to discriminate between HiHigCan cancer and not having HiHigCan cancer. FIG. 31 illustrates a ROC for the convolutional network architecture scores for the data of FIG. 30.

Figure 32:
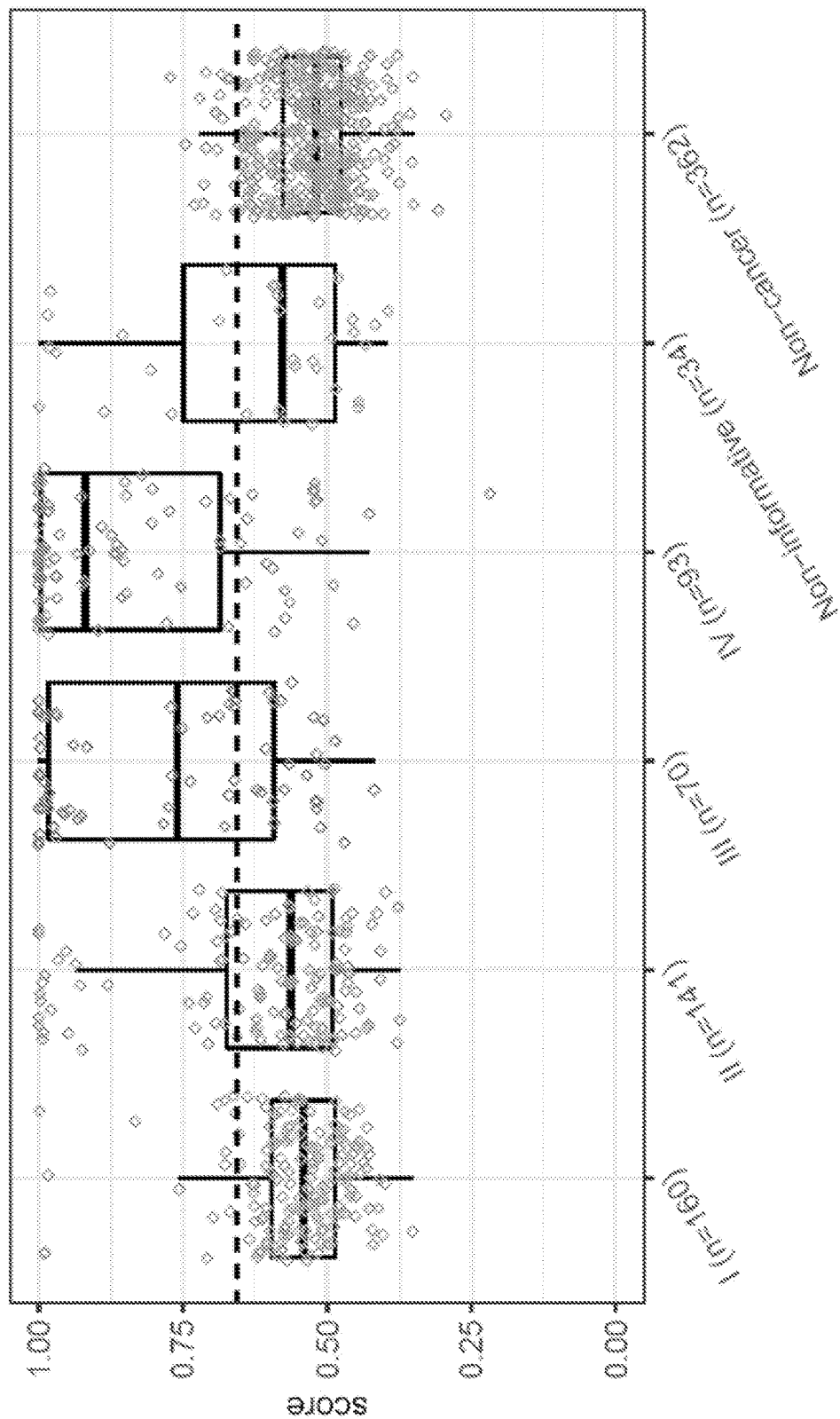

FIGS. 32 and 33 illustrate the convolutional network architecture 138 scores of the instant disclosure for invasive cancers, which are histologically confirmed invasive cancers, by cancer stage, in accordance with an embodiment of the present disclosure. In FIGS. 32 and 33, 160 subjects that have stage I of an invasive cancer, 141 subjects that have stage II of an invasive cancer, 70 subjects that have stage III of an invasive cancer, 34 subjects that are non-informative, and 362 subjects that do not have cancer are evaluated. For FIG. 32, the scorer 152 returned score values for both "cancer" (positive class score) and "non-cancer" for each subject in the population. These two score values sum to one. Thus, for example, what is shown in FIG. 32 for the stage I population is the positive class score (has cancer) that the scorer 152 of network architecture 138 gave for each of the 160 subjects that have stage I cancer (across all the cancers represented by the 160 subjects). Likewise, what is shown in FIG. 32 for stage II cancer is the positive class score (has cancer) that the scorer 152 of network architecture 138 gave for each of the 141 subjects that have stage II cancer. What is seen in FIG. 32 is a general trend to a higher positive class score as the stage of cancer progresses.

Figure 34:
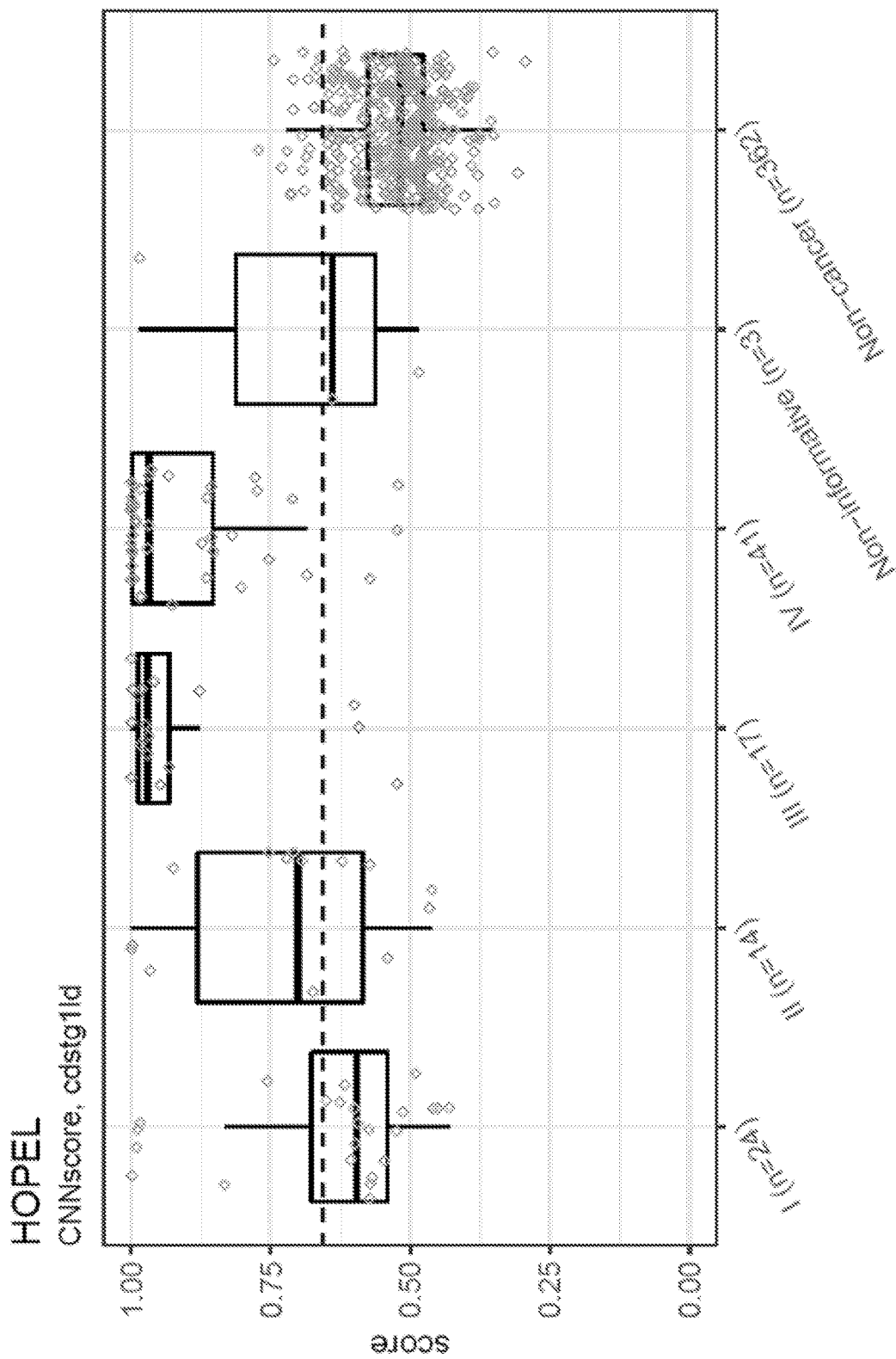

FIGS. 34 and 35 illustrate the convolutional network architecture 138 scores of the instant disclosure for cancer type classification for the high mortality cancers: hepatobiliary, ovarian, pancreatic, esophageal, lung (HOPEL) broken out by cancer stage, in accordance with an embodiment of the present disclosure. In FIGS. 34 and 35, 24 training subjects that have stage I of a HOPEL cancer, 14 training subjects that have stage II of a HOPEL cancer, 17 training subjects that have stage III of a HOPEL cancer, 41 training subjects that have stage IV of a HOPEL cancer, and 362 training subjects that do not have cancer are evaluated. For FIG. 34, the scorer 152 returned score values for both "cancer" (positive class score) and "non-cancer" for each subject in the population tested for these Figures. These two score values sum to one. Thus, for example, what is shown in FIG. 34 for the stage I population is the positive class score (has cancer) that the scorer 152 of network architecture 138 gave for each of the 24 subjects that has a HOPEL cancer that is in stage I. Likewise, what is shown in FIG. 34 for stage II cancer is the positive class score (has cancer) that the scorer 152 of network architecture 138 gave for each of the 14 subjects that have a HOPEL cancer that is in stage II. What is seen in FIG. 34 is a general trend to a higher positive class score as the stage of HOPEL cancer progresses.

Figure 36:
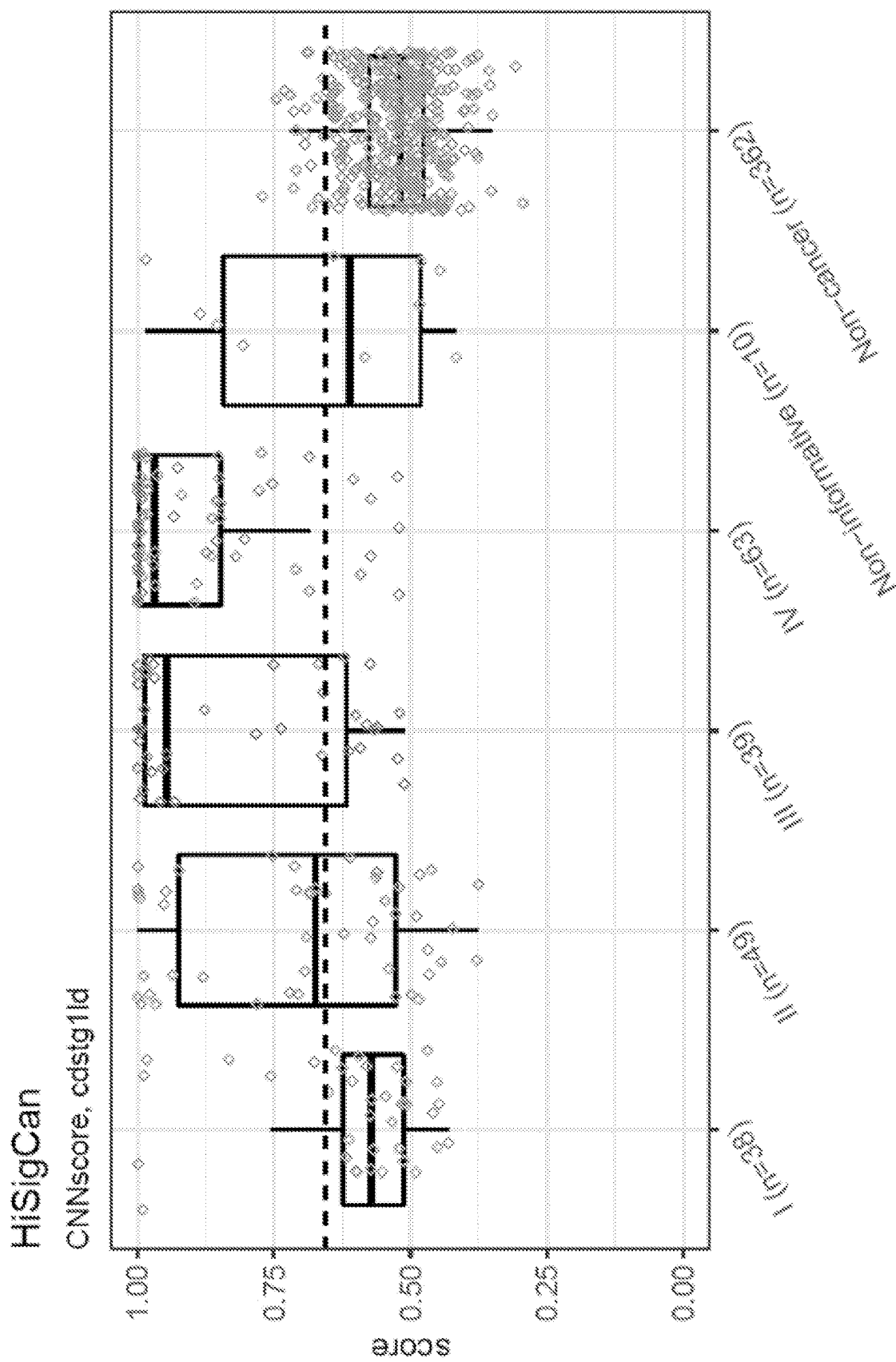
Figure 38:
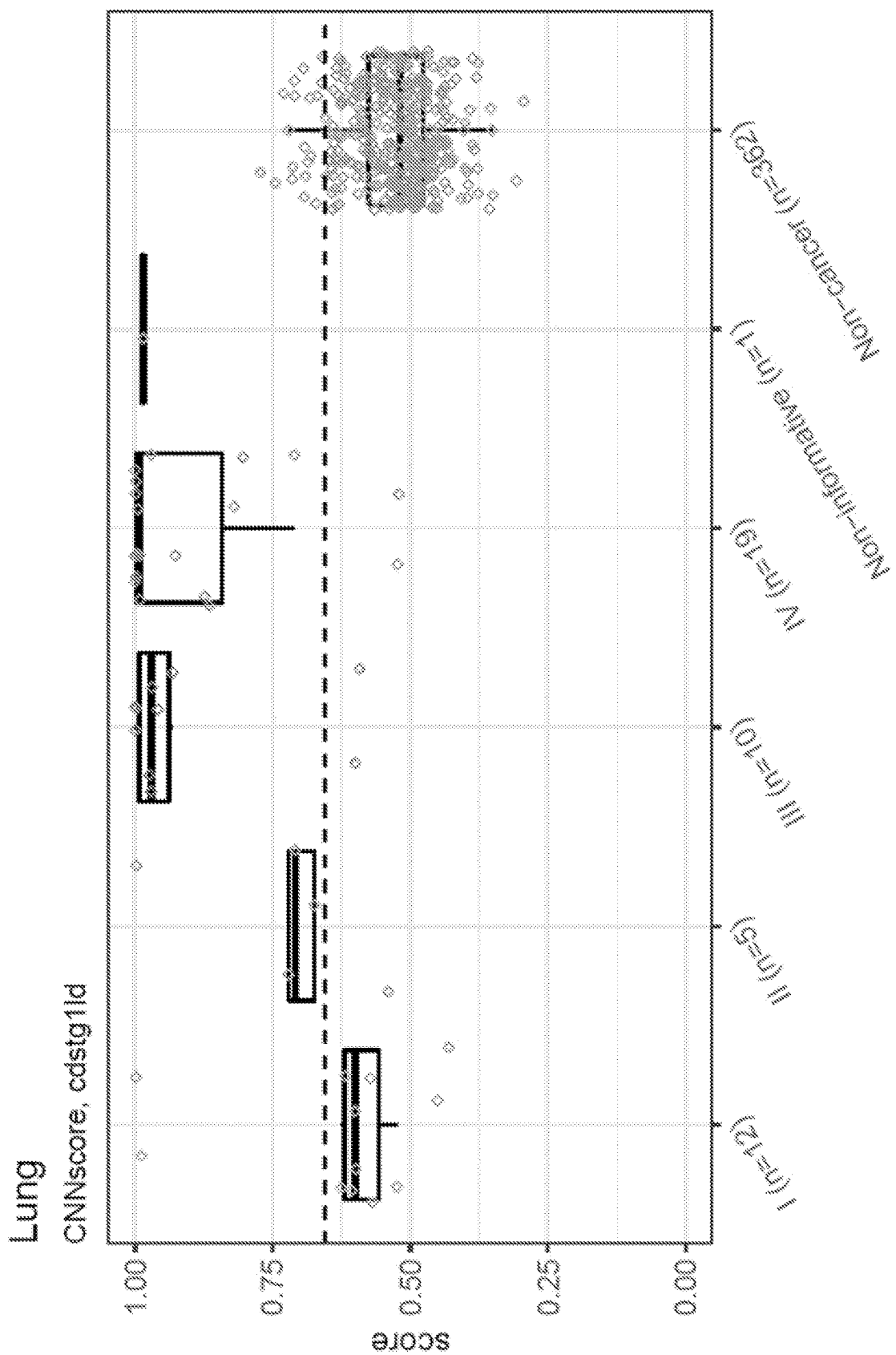

FIGS. 36 and 37 illustrate the convolutional network architecture scores of the instant disclosure for high signal cancers (HiSigCan), which are defined as single primary invasive cancer of: ER− breast, colorectal, lung, pancreatic, ovarian, hepatobiliary, gastric, head and neck, and esophageal cancer, broken out by cancer stage. In FIGS. 36 and 37, 38 training subjects that have stage I of a HiSigCan cancer, 49 training subjects that have stage II of a HiSigCan cancer, 39 training subjects that have stage III of a HiSigCan cancer, 63 training subjects that have stage IV of a HiSigCan cancer, 10 training subject that are non-informative and 362 training subjects that do not have cancer are evaluated. For FIG. 36, the scorer 152 returned score values for both "cancer" (positive class score) and "non-cancer" for each subject in the population tested for these Figures. These two score values sum to one. Thus, for example, what is shown in FIG. 36 for the stage I population is the positive class score (has cancer) that the scorer 152 of network architecture 138 gave for each of the 38 subjects that has a HiSigCan cancer that is in stage I. Likewise, what is shown in FIG. 34 for stage II cancer is the positive class score (has cancer) that the scorer 152 of network architecture 138 gave for each of the 49 subjects that have a HiSigCan cancer that is in stage II. What is seen in FIG. 36 is a general trend to a higher positive class score as the stage of HiSigCan cancer progresses.

FIGS. 38 and 39 illustrate the convolutional network architecture 138 scores of the instant disclosure for lung cancer, broken out by cancer stage, in accordance with an embodiment of the present disclosure. In FIGS. 38 and 39, 12 training subjects that have stage I lung cancer, 5 training subjects that have stage II lung cancer, 10 training subjects that have stage III lung cancer, 19 training subjects that have stage IV lung cancer, 1 training subject that is non-informative, and 362 training subjects that do not have cancer are evaluated. For FIG. 38, the scorer 152 returned score values for both "cancer" (positive class score) and "non-cancer" for each subject in the population tested for these Figures. These two score values sum to one. Thus, for example, what is shown in FIG. 38 for the stage I population is the positive class score (has cancer) that the scorer 152 of network architecture 138 gave for each of the 12 subjects that have stage I lung cancer. Likewise, what is shown in FIG. 34 for stage II cancer is the positive class score (has cancer) that the scorer 152 of network architecture 138 gave for each of the 5 subjects that have stage II lung cancer. What is seen in FIG. 38 is a general trend to a higher positive class score as the stage of lung cancer progresses.

Figure 40:
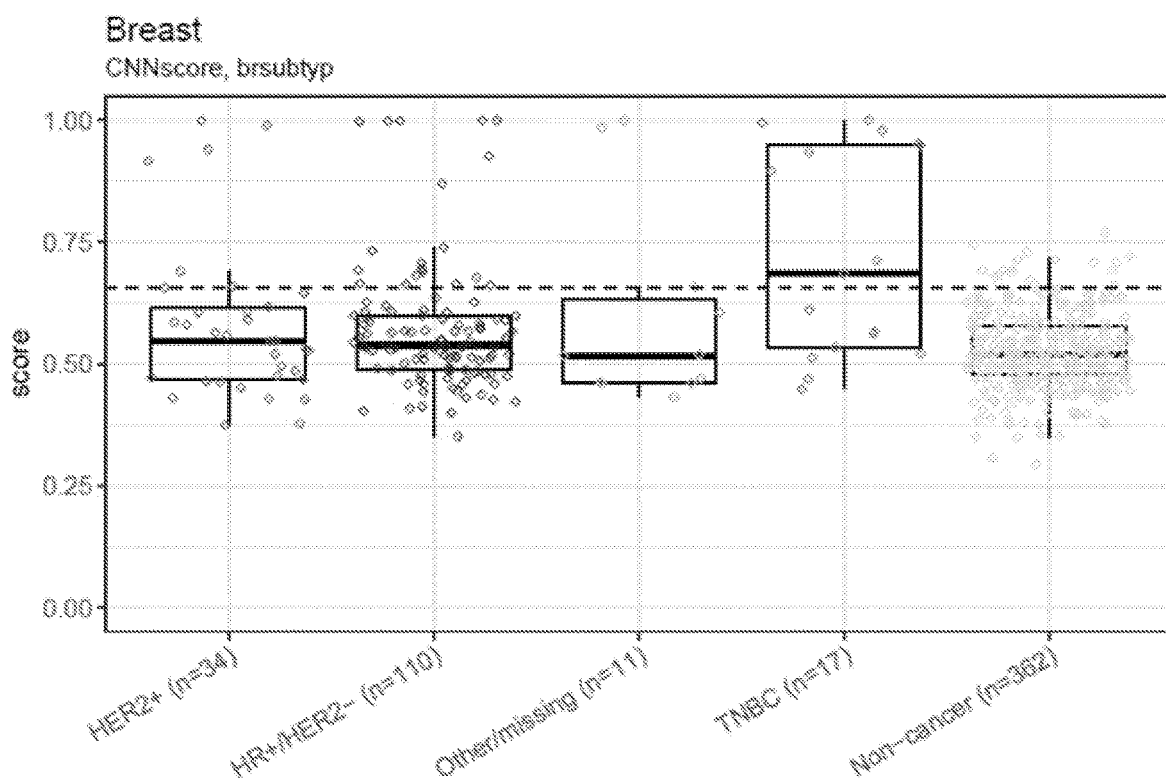
FIGS. 40 and 41 illustrates sample convolutional network architecture scores of the instant disclosure for breast cancer, broken out by sub-types, in accordance with an embodiment of the present disclosure.
Figure 41:
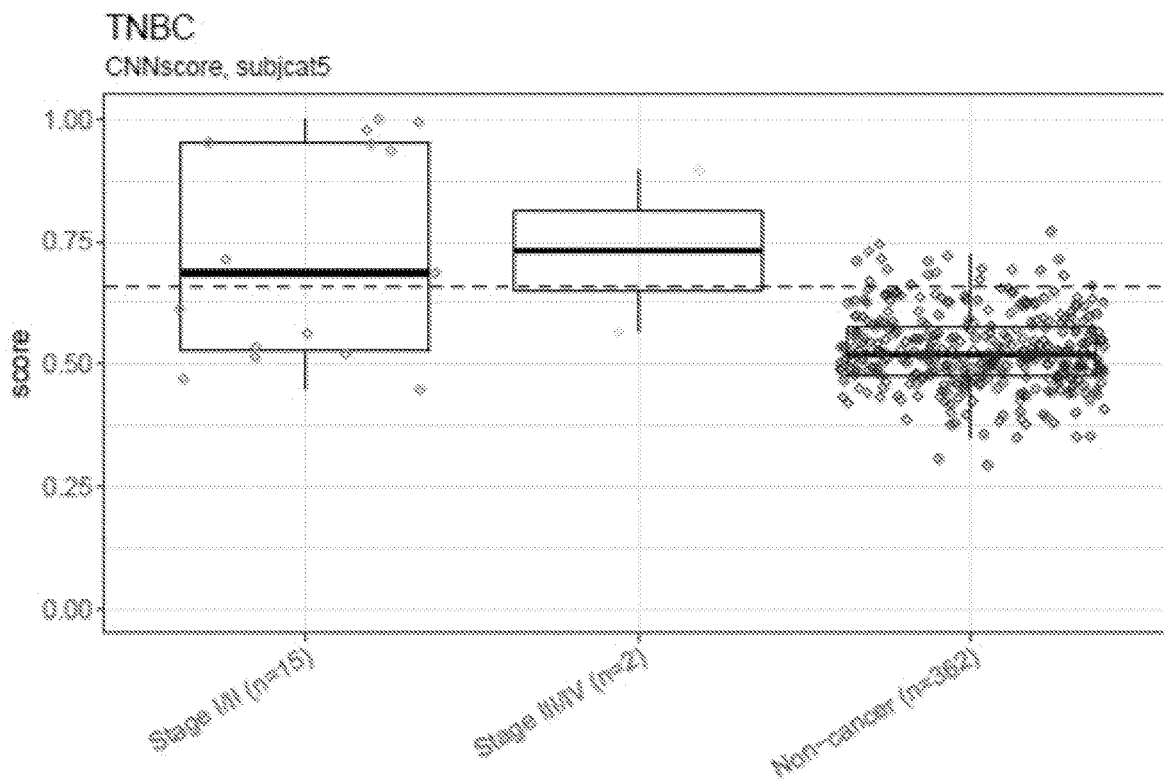

FIG. 40 illustrates the convolutional network architecture scores 138 for lung cancer, broken out by sub-types, in accordance with an embodiment of the present disclosure.

Figure 5:
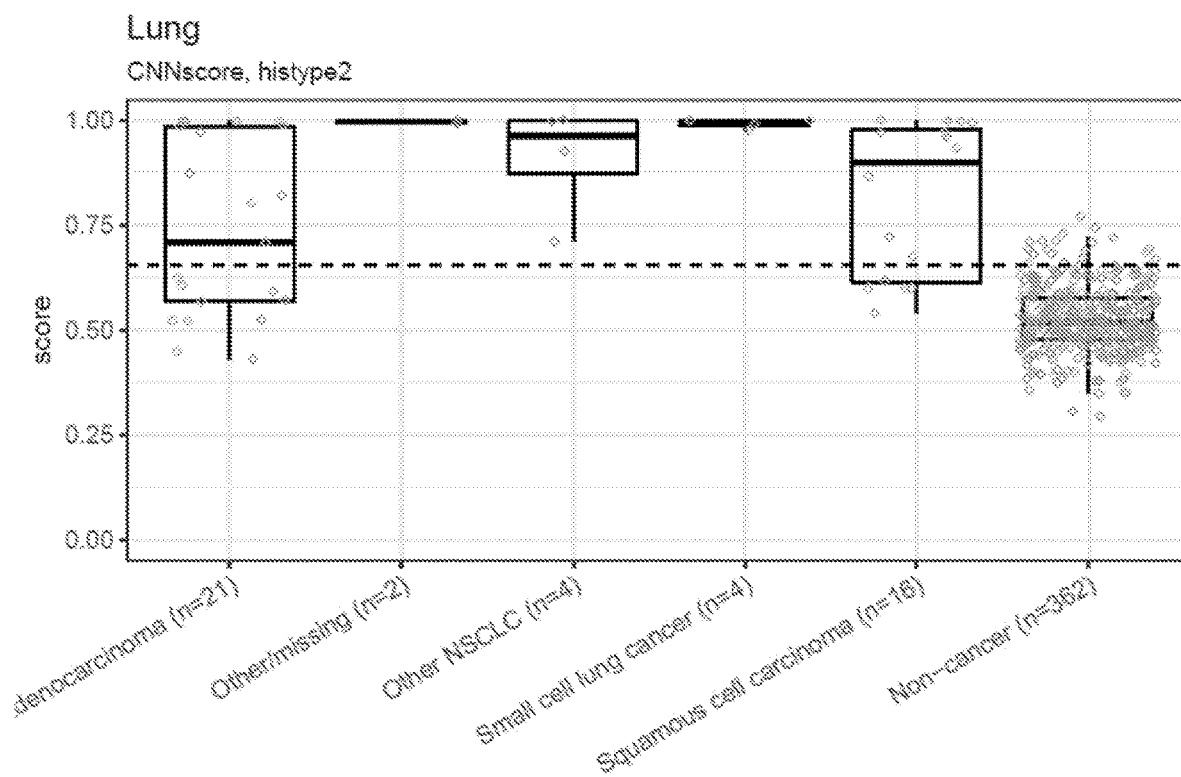
FIG. 5 illustrates the convolutional network architecture scores of the instant disclosure for triple-negative breast cancer (breast cancers that that tested negative for estrogen receptors (ER–), progesterone receptors (PR–), and HER2 (HER2–) separated by cancer stages, in accordance with an embodiment of the present disclosure.

FIG. 5 illustrates the convolutional network architecture 138 scores for triple-negative breast cancer (breast cancers that that tested negative for estrogen receptors (ER−), progesterone receptors (PR−), and HER2 (HER2−) separated by cancer stages.

Example 6: Convolutional Neural Network Run Times

In this example some metrics for the network architecture 138 of the present disclosure is provided. All computations were performed on an NVidia DGX-Station deep learning system.

Training. The framework used to encode the network architecture is Tensorflow. See the Internet at https://www- .tensorflow.org/. The total number of trainable parameters was 4094. This included the first weights for the first and second convolutional layers. The number of training epochs was 1000. The number of training subjects in the training batch was 128. The average training step time (per epoch) was 800 milliseconds. There were 12 steps per epoch. The average training time per epoch step was 9.6 seconds. The average training time for 1000 epochs was 2.66 hours. Thus, the total average training time for 10 fold cross validated models was 10*2.66 hrs for a total of 26.6 hrs. These metrics assume 100% availability of the DGX-Station—with no other CPU or GPU intensive process is running. The training was distributed to all four V100 GPUs in the Nvidia box. The hardware is highly optimized for deep learning and training could take much longer (weeks) on conventional workstations.

Evaluation. The framework used was Tensorflow. A single epoch was used for evaluation. The evaluation batch size was approximately 900 subjects. The steps per epoch was 1. The average evaluation time per epoch was 10.89 seconds. All samples were evaluated in one batch so there is only one step.

Model architecture is Tensorflow. Table 1 below shows the model architecture of the network architecture 138 that was used in accordance with this example.

TABLE 1

Network architecture 138 used in this example.

| Layer No. | Layer Type | Output Shape | Paramaters |
|---|---|---|---|
| 1 | input_1 (InputLayer) | (None, 1, 2239, 22) | 0 |
| 2 | depthwise_conv2d_1 | (Depthwise (None, 1, 555, 44) | 1012 |
| 3 | max_pooling2d_1 | (MaxPooling2 (None, 1, 185, 44) | 0 |
| 4 | depthwise_conv2d_2 | (Depthwise (None, 1, 59, 44) | 528 |
| 5 | max_pooling2d_2 | (MaxPooling2 (None, 1, 29, 44) | 0 |
| 6 | flatten_1 (Flatten) | (None, 1276) | 0 |
| 7 | dropout_1 (Dropout) | (None, 1276) | 0 |
| 8 | x_train_out (Dense) | (None, 2) | 2554 |

Layer number 1 of Table 1 is an input layer for receiving vector sets 130.

Layer number 2 of Table 1 is illustrated as convolutional filter layer 302 of FIG. 3. The network architecture 138 runs the data in two track mode, with the contribution from white blood cells to cell-free nucleic acids in a biological sample from each of the twenty-two autosomal chromosomes routed to twenty-two different first convolutional layers 302 and the contribution from non-white blood cells to cell-free nucleic acids in the biological sample from each of the twenty-two autosomal chromosomes routed to twenty-two additional first convolutional layers 302 for a total of 44 convolutional neural network paths and 1012 trainable weights associated with these first convolutional layers 302.

Layer number 3 of Table 1 is illustrated as Max pooling layer 304 of FIG. 3 and has no trainable parameters.

Layer number 4 of Table 1 is illustrates as convolutional filter layer 306 of FIG. 3. The network architecture 138 runs the data in two track mode, with a total of 44 convolutional neural network paths and 528 trainable weights associated the convolutional layers 306 of these convolutional neural network paths 140.

Layer number 5 of Table 1 is illustrated as Max pooling layer 308 of FIG. 3 and has no trainable parameters.

Layers 6 and 7 of Table 1 are processing layers that are not illustrated in FIG. 3.

Layer 8 of Table 1 is illustrated as scorer 152 of FIG. 3 and has 2554 trainable parameters.

Example 7: Comparison of Convolutional Neural Network Performance to Other Classifiers Table 2 below provides a comparison of the performance of the network architecture of FIG. 3 and Example 6 (termed "CNN" in Table 2) versus the B-score classifier (termed "B-score in Table 2) (see U.S. patent application Ser. No. 16/352,739, entitled "Method and System for Selecting, Managing, and Analyzing Data of High Dimensionality," filed Mar. 13, 2019) as well the M-Score classifier (termed "M-Score" in Table 2) (see U.S. patent application Ser. No. 16/352,602 entitled "Anomalous Fragment Detection and classification," filed Mar. 13, 2019, which is hereby incorporated by reference). In Table 2 the term "Inv. Can" stands for invasive cancer and is defined as histologically confirmed invasive cancers. In Table 2 "Sn@95Sp" stands for "average sensitivity at 95 percent specificity, Sn@98Sp" stands for "average sensitivity at 98 percent specifity", and Sn@99Sp" stands for "average sensitivity at 99 percent specificity." Thus, Sn@95Sp, for example is the average sensitivity of a classifier at a particular specificity level. As used in Table 2, sensitivity is the ability of a classifier to correctly classify an individual as having cancer. As used in Table 2 specificity is the ability of a classifier to correctly classify an individual as disease-free. Thus, Table 2 uses various specificity cut-off values (95 percent, 98 percent or 99 percent) in which to evaluate the sensitivity of the classifiers.

TABLE 2

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M-score Sn@95Sp |
|---|---|---|---|---|---|
| All Inv.Can. (omit NonInf): subjcat3: Non-cancer (362) vs Invasive Cancer (464) | 0.317 (0.275-0.361) | 0.364 (0.32-0.41) | 0.293 (0.252-0.337) | 0.289 (0.248-0.332) | 0.366 (0.322-0.412) |
| Anorectal(omit NonInf): subjcat3: Non-cancer (362) vs Invasive Cancer (2) | 1 (0.158-1) | 1 (0.158-1) | 1 (0.158-1) | 1 (0.158-1) | 1 (0.158-1) |
| Anorectal: subjcat3: Non-cancer (362) vs Invasive Cancer (3) | 1 (0.292-1) | 0.667 (0.094-0.992) | 0.667 (0.094-0.992) | 0.667 (0.094-0.992) | 0.667 (0.094-0.992) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M- score Sn@95Sp |
|---|---|---|---|---|---|
| Bladder(omit NonInf): subjcat3: Non-cancer (362) vs Invasive Cancer (1) | 0 (0-0.975) | 0 (0-0.975) | 0 (0-0.975) | 0 (0-0.975) | 0 (0-0.975) |
| Bladder: subjcat3: Non-cancer (362) vs Invasive Cancer (1) | 0 (0-0.975) | 0 (0-0.975) | 0 (0-0.975) | 0 (0-0.975) | 0 (0-0.975) |
| Breast(HR−): subjcat3: Non-cancer (362) vs Invasive Cancer (22) | 0.364 (0.172-0.593) | 0.454 (0.244-0.678) | 0.409 (0.207-0.636) | 0.364 (0.172-0.593) | 0.364 (0.172-0.593) |
| Breast (omit NonInf)(HR−): subjcat3: Non-cancer (362) vs Invasive Cancer (22) | 0.364 (0.172-0.593) | 0.454 (0.244-0.678) | 0.409 (0.207-0.636) | 0.364 (0.172-0.593) | 0.364 (0.172-0.593) |
| Breast(omit NonInf): subjcat3: Non-cancer (362) vs Invasive Cancer (170) | 0.141 (0.093-0.203) | 0.206 (0.148-0.275) | 0.135 (0.088-0.196) | 0.129 (0.083-0.189) | 0.159 (0.107-0.223) |
| Breast: subjcat3: Non-cancer (362) vs Invasive Cancer (172) | 0.14 (0.091-0.2) | 0.204 (0.146-0.271) | 0.134 (0.087-0.194) | 0.128 (0.082-0.187) | 0.157 (0.106-0.22) |
| Cancer of unknown primary(omit NonInf): subjcat3: Non-cancer (362) vs Invasive Cancer (8) | 0.625 (0.245-0.915) | 0.75 (0.349-0.968) | 0.625 (0.245-0.915) | 0.625 (0.245-0.915) | 0.875 (0.473-0.997) |
| Cancer of unknown primary: subjcat3: Non-cancer (362) vs Invasive Cancer (9) | 0.667 (0.299-0.925) | 0.778 (0.4-0.972) | 0.667 (0.299-0.925) | 0.667 (0.299-0.925) | 0.889 (0.518-0.997) |
| Cervical cancer (cervix)(omit NonInf): subjcat3: Non-cancer (362) vs Invasive Cancer (8) | 0.25 (0.032-0.651) | 0.125 (0.003-0.527) | 0.125 (0.003-0.527) | 0.125 (0.003-0.527) | 0.5 (0.157-0.843) |
| Cervical cancer (cervix): subjcat3: Non-cancer (362) vs Invasive Cancer (8) | 0.25 (0.032-0.651) | 0.125 (0.003-0.527) | 0.125 (0.003-0.527) | 0.125 (0.003-0.527) | 0.5 (0.157-0.843) |
| Colorectal(omit NonInf): subjcat3: Non-cancer (362) vs Invasive Cancer (39) | 0.564 (0.396-0.722) | 0.59 (0.421-0.744) | 0.513 (0.348-0.676) | 0.513 (0.348-0.676) | 0.641 (0.472-0.788) |
| Colorectal: subjcat3: Non-cancer (362) vs Invasive Cancer (45) | 0.533 (0.379-0.683) | 0.578 (0.422-0.723) | 0.511 (0.358-0.663) | 0.511 (0.358-0.663) | 0.622 (0.465-0.762) |
| Esophageal(omit NonInf): subjcat3: Non-cancer (362) vs Invasive Cancer (7) | 0.429 (0.099-0.816) | 0.571 (0.184-0.901) | 0.429 (0.099-0.816) | 0.429 (0.099-0.816) | 0.429 (0.099-0.816) |
| Esophageal: subjcat3: Non-cancer (362) vs Invasive Cancer (7) | 0.429 (0.099-0.816) | 0.571 (0.184-0.901) | 0.429 (0.099-0.816) | 0.429 (0.099-0.816) | 0.429 (0.099-0.816) |
| Gastric(omitNonInf): subjcat3: Non-cancer (362) vs Invasive Cancer (13) | 0.462 (0.192-0.749) | 0.462 (0.192-0.749) | 0.308 (0.091-0.614) | 0.308 (0.091-0.614) | 0.462 (0.192-0.749) |
| Gastric: subjcat3: Non-cancer (362) vs Invasive Cancer (14) | 0.429 (0.177-0.711) | 0.429 (0.177-0.711) | 0.286 (0.084-0.581) | 0.286 (0.084-0.581) | 0.429 (0.177-0.711) |
| Head/Neck(omit NonInf): subjcat3: Non-cancer (362) vs Invasive Cancer (12) | 0.333 (0.099-0.651) | 0.5 (0.211-0.789) | 0.417 (0.152-0.723) | 0.417 (0.152-0.723) | 0.5 (0.211-0.789) |
| Head/Neck: subjcat3: Non-cancer (362) vs Invasive Cancer (12) | 0.333 (0.099-0.651) | 0.5 (0.211-0.789) | 0.417 (0.152-0.723) | 0.417 (0.152-0.723) | 0.5 (0.211-0.789) |
| Hepatobiliary(omit NonInf): subjcat3: Non-cancer (362) vs Invasive Cancer (14) | 0.643 (0.351-0.872) | 0.714 (0.419-0.916) | 0.714 (0.419-0.916) | 0.714 (0.419-0.916) | 0.786 (0.492-0.953) |
| Hepatobiliary: subjcat3: Non-cancer (362) vs Invasive Cancer (15) | 0.6 (0.323-0.837) | 0.667 (0.384-0.882) | 0.667 (0.384-0.882) | 0.667 (0.384-0.882) | 0.733 (0.449-0.922) |
| HiSigCan (omit NonInf): subjcat3: Non-cancer (362) vs Invasive Cancer (189) | 0.54 (0.466-0.612) | 0.614 (0.54-0.684) | 0.545 (0.471-0.617) | 0.534 (0.461-0.607) | 0.624 (0.551-0.694) |
| HOPEL (omit NonInf): subjcat3: Non-cancer (362) vs Invasive Cancer (96) | 0.625 (0.52-0.722) | 0.698 (0.596-0.787) | 0.656 (0.552-0.75) | 0.646 (0.542-0.741) | 0.719 (0.618-0.806) |
| Lung (noNonInf): subjcat3: Non-cancer (362) vs Invasive Cancer (46) | 0.609 (0.454-0.749) | 0.674 (0.52-0.805) | 0.63 (0.475-0.768) | 0.609 (0.454-0.749) | 0.696 (0.542-0.823) |
| Lung(omit NonInf): subjcat3: Non-cancer (362) vs Invasive Cancer (46) | 0.609 (0.454-0.749) | 0.674 (0.52-0.805) | 0.63 (0.475-0.768) | 0.609 (0.454-0.749) | 0.696 (0.542-0.823) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M- score Sn@95Sp |
|---|---|---|---|---|---|
| Lung: subjcat3: Non-cancer (362) vs Invasive Cancer (47) | 0.617 (0.464-0.755) | 0.681 (0.529-0.809) | 0.638 (0.485-0.773) | 0.617 (0.464-0.755) | 0.702 (0.551-0.827) |
| Lymphoma(omit NonInf): subjcat3: Non-cancer (362) vs Invasive Cancer (18) | 0.611 (0.357-0.827) | 0.556 (0.308-0.785) | 0.444 (0.215-0.692) | 0.444 (0.215-0.692) | 0.722 (0.465-0.903) |
| Lymphoma: subjcat3: Non-cancer (362) vs Invasive Cancer (22) | 0.591 (0.364-0.793) | 0.591 (0.364-0.793) | 0.5 (0.282-0.718) | 0.5 (0.282-0.718) | 0.682 (0.451-0.861) |
| Melanoma(omit NonInf): subjcat3: Non-cancer (362) vs Invasive Cancer (8) | 0.5 (0.157-0.843) | 0.25 (0.032-0.651) | 0.25 (0.032-0.651) | 0.25 (0.032-0.651) | 0.375 (0.085-0.755) |
| Melanoma: subjcat3: Non-cancer (362) vs Invasive Cancer (10) | 0.4 (0.122-0.738) | 0.3 (0.067-0.652) | 0.2 (0.025-0.556) | 0.2 (0.025-0.556) | 0.3 (0.067-0.652) |
| Other(omit NonInf): subjcat3: Non-cancer (362) vs Invasive Cancer (7) | 0.143 (0.004-0.579) | 0.143 (0.004-0.579) | 0.143 (0.004-0.579) | 0.143 (0.004-0.579) | 0.286 (0.037-0.71) |
| Other: subjcat3: Non-cancer (362) vs Invasive Cancer (8) | 0.125 (0.003-0.527) | 0.125 (0.003-0.527) | 0.125 (0.003-0.527) | 0.125 (0.003-0.527) | 0.25 (0.032-0.651) |
| Ovarian(omit NonInf): subjcat3: Non-cancer (362) vs Invasive Cancer (7) | 0.714 (0.29-0.963) | 0.714 (0.29-0.963) | 0.714 (0.29-0.963) | 0.714 (0.29-0.963) | 0.714 (0.29-0.963) |
| Ovarian: subjcat3: Non-cancer (362) vs Invasive Cancer (7) | 0.714 (0.29-0.963) | 0.714 (0.29-0.963) | 0.714 (0.29-0.963) | 0.714 (0.29-0.963) | 0.714 (0.29-0.963) |
| Pancreas(omit NonInf): subjcat3: Non-cancer (362) vs Invasive Cancer (22) | 0.682 (0.451-0.861) | 0.773 (0.546-0.922) | 0.727 (0.498-0.893) | 0.727 (0.498-0.893) | 0.818 (0.597-0.948) |
| Pancreas: subjcat3: Non-cancer (362) vs Invasive Cancer (23) | 0.652 (0.427-0.836) | 0.739 (0.516-0.898) | 0.696 (0.471-0.868) | 0.696 (0.471-0.868) | 0.783 (0.563-0.925) |
| Prostate(omit NonInf): subjcat3: Non-cancer (362) vs Invasive Cancer (55) | 0 (0-0.065) | 0.036 (0.004-0.125) | 0 (0-0.065) | 0 (0-0.065) | 0 (0-0.065) |
| Prostate: subjcat3: Non-cancer (362) vs Invasive Cancer (58) | 0 (0-0.062) | 0.052 (0.011-0.144) | 0 (0-0.062) | 0 (0-0.062) | 0 (0-0.062) |
| Renal(omit NonInf): subjcat3: Non-cancer (362) vs Invasive Cancer (13) | 0.231 (0.05-0.538) | 0.308 (0.091-0.614) | 0.077 (0.002-0.36) | 0.077 (0.002-0.36) | 0.231 (0.05-0.538) |
| Renal: subjcat3: Non-cancer (362) vs Invasive Cancer (18) | 0.222 (0.064-0.476) | 0.278 (0.097-0.535) | 0.111 (0.014-0.347) | 0.111 (0.014-0.347) | 0.222 (0.064-0.476) |
| Thyroid(omit NonInf): subjcat3: Non-cancer (362) vs Invasive Cancer (5) | 0.2 (0.005-0.716) | 0.2 (0.005-0.716) | 0 (0-0.522) | 0 (0-0.522) | 0 (0-0.522) |
| Thyroid: subjcat3: Non-cancer (362) vs Invasive Cancer (10) | 0.1 (0.003-0.445) | 0.1 (0.003-0.445) | 0 (0-0.308) | 0 (0-0.308) | 0 (0-0.308) |
| Uterine(omit NonInf): subjcat3: Non-cancer (362) vs Invasive Cancer (9) | 0.222 (0.028-0.6) | 0.333 (0.075-0.701) | 0.111 (0.003-0.482) | 0.111 (0.003-0.482) | 0.333 (0.075-0.701) |
| Uterine: subjcat3: Non-cancer (362) vs Invasive Cancer (9) | 0.222 (0.028-0.6) | 0.333 (0.075-0.701) | 0.111 (0.003-0.482) | 0.111 (0.003-0.482) | 0.333 (0.075-0.701) |
| Breast: brsubtyp2b: HR+ (139) vs Non-cancer (362) | 0.101 (0.056-0.163) | 0.166 (0.108-0.238) | 0.086 (0.045-0.146) | 0.086 (0.045-0.146) | 0.122 (0.073-0.189) |
| Breast: brsubtyp2b: HR− (22) vs Non-cancer (362) | 0.364 (0.172-0.593) | 0.454 (0.244-0.678) | 0.409 (0.207-0.636) | 0.364 (0.172-0.593) | 0.364 (0.172-0.593) |
| Breast: brsubtyp2: HER2+/HR+ (29) vs Non-cancer (362) | 0.103 (0.022-0.274) | 0.138 (0.039-0.317) | 0.103 (0.022-0.274) | 0.103 (0.022-0.274) | 0.103 (0.022-0.274) |
| Breast: brsubtyp2: HER2+/HR− (5) vs Non-cancer (362) | 0.2 (0.005-0.716) | 0.2 (0.005-0.716) | 0.2 (0.005-0.716) | 0.2 (0.005-0.716) | 0.2 (0.005-0.716) |
| Breast: brsubtyp: HER2+ (34) vs Non-cancer (362) | 0.118 (0.033-0.275) | 0.147 (0.05-0.311) | 0.118 (0.033-0.275) | 0.118 (0.033-0.275) | 0.118 (0.033-0.275) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M-score Sn@95Sp |
|---|---|---|---|---|---|
| Breast: brsubtyp: HR+/HER2− (110) vs Non-cancer (362) | 0.1 (0.051-0.172) | 0.173 (0.107-0.257) | 0.082 (0.038-0.15) | 0.082 (0.038-0.15) | 0.127 (0.071-0.204) |
| Breast: brsubtyp: TNBC (17) vs Non-cancer (362) | 0.412 (0.184-0.671) | 0.529 (0.278-0.77) | 0.471 (0.23-0.722) | 0.412 (0.184-0.671) | 0.412 (0.184-0.671) |
| Breast(no StgNonInf): brsubtyp2b: HR+ (137) vs Non-cancer (362) | 0.102 (0.057-0.166) | 0.168 (0.11-0.241) | 0.088 (0.046-0.148) | 0.088 (0.046-0.148) | 0.124 (0.074-0.191) |
| Breast(no StgNonInf): brsubtyp2b: HR− (22) vs Non-cancer (362) | 0.364 (0.172-0.593) | 0.454 (0.244-0.678) | 0.409 (0.207-0.636) | 0.364 (0.172-0.593) | 0.364 (0.172-0.593) |
| Breast(no StgNonInf): brsubtyp2: HER2+/HR+ (28) vs Non-cancer (362) | 0.107 (0.023-0.282) | 0.143 (0.04-0.327) | 0.107 (0.023-0.282) | 0.107 (0.023-0.282) | 0.107 (0.023-0.282) |
| Breast(no StgNonInf): brsubtyp2: HER2+/HR− (5) vs Non-cancer (362) | 0.2 (0.005-0.716) | 0.2 (0.005-0.716) | 0.2 (0.005-0.716) | 0.2 (0.005-0.716) | 0.2 (0.005-0.716) |
| Breast(no StgNonInf): brsubtyp: HER2+ (33) vs Non-cancer (362) | 0.121 (0.034-0.282) | 0.152 (0.051-0.319) | 0.121 (0.034-0.282) | 0.121 (0.034-0.282) | 0.121 (0.034-0.282) |
| Breast(no StgNonInf): brsubtyp: HR+/HER2− (109) vs Non-cancer (362) | 0.101 (0.051-0.173) | 0.174 (0.108-0.259) | 0.083 (0.038-0.151) | 0.083 (0.038-0.151) | 0.128 (0.072-0.206) |
| Breast(no StgNonInf): brsubtyp: TNBC (17) vs Non-cancer (362) | 0.412 (0.184-0.671) | 0.529 (0.278-0.77) | 0.471 (0.23-0.722) | 0.412 (0.184-0.671) | 0.412 (0.184-0.671) |
| IBC: Dx method: cohort.cdmethod: IBC: scrnd (94) vs NC: NA (362) | 0.043 (0.012-0.105) | 0.085 (0.037-0.161) | 0.021 (0.003-0.075) | 0.011 (0-0.058) | 0.043 (0.012-0.105) |
| IBC: Dx method: cohort.cdmethod: IBC: scrnd (78) vs NC: NA (362) | 0.256 (0.164-0.368) | 0.346 (0.242-0.462) | 0.269 (0.175-0.382) | 0.269 (0.175-0.382) | 0.295 (0.197-0.409) |
| Lung: histype: Adenocarcinoma (21) vs Non-cancer (362) | 0.476 (0.257-0.702) | 0.524 (0.298-0.743) | 0.476 (0.257-0.702) | 0.476 (0.257-0.702) | 0.619 (0.384-0.819) |
| Lung: histype: Non-small cell lung cancer (4) vs Non-cancer (362) | 0.75 (0.194-0.994) | 1 (0.398-1) | 1 (0.398-1) | 0.75 (0.194-0.994) | 1 (0.398-1) |
| Lung: histype: Small cell lung cancer (4) vs Non-cancer (362) | 1 (0.398-1) | 1 (0.398-1) | 1 (0.398-1) | 1 (0.398-1) | 1 (0.398-1) |
| Lung: histype: Squamous cell carcinoma (16) vs Non-cancer (362) | 0.625 (0.354-0.848) | 0.688 (0.413-0.89) | 0.625 (0.354-0.848) | 0.625 (0.354-0.848) | 0.625 (0.354-0.848) |
| Lung (noNonInf): subjcat3: Non-cancer (362) vs Invasive Cancer (46) | 0.609 (0.454-0.749) | 0.674 (0.52-0.805) | 0.63 (0.475-0.768) | 0.609 (0.454-0.749) | 0.696 (0.542-0.823) |
| Lung: Resect: res = F (22) vs Non-cancer (362) | 0.864 (0.651-0.971) | 0.909 (0.708-0.989) | 0.909 (0.708-0.989) | 0.864 (0.651-0.971) | 0.909 (0.708-0.989) |
| Lung: Resect: res = T (24) vs Non-cancer (362) | 0.375 (0.188-0.594) | 0.458 (0.256-0.672) | 0.375 (0.188-0.594) | 0.375 (0.188-0.594) | 0.5 (0.291-0.709) |
| All Inv.Can.: cdstg1ld: I (160) vs Non-cancer (362) | 0.062 (0.03-0.112) | 0.088 (0.049-0.142) | 0.038 (0.014-0.08) | 0.038 (0.014-0.08) | 0.106 (0.063-0.165) |
| All Inv.Can.: cdstg1ld: II (141) vs Non-cancer (362) | 0.184 (0.124-0.258) | 0.262 (0.192-0.343) | 0.177 (0.118-0.251) | 0.17 (0.112-0.243) | 0.213 (0.148-0.29) |
| All Inv.Can.: cdstg1ld: III (70) vs Non-cancer (362) | 0.557 (0.433-0.676) | 0.657 (0.534-0.767) | 0.529 (0.406-0.649) | 0.529 (0.406-0.649) | 0.629 (0.505-0.741) |
| All Inv.Can.: cdstg1ld: IV (93) vs Non-cancer (362) | 0.774 (0.676-0.854) | 0.774 (0.676-0.854) | 0.731 (0.629-0.818) | 0.72 (0.618-0.809) | 0.85 (0.76-0.915) |
| All Inv.Can. (omit NonInf): subjcat3: Non-cancer (362) vs Invasive Cancer (464) | 0.317 (0.275-0.361) | 0.364 (0.32-0.41) | 0.293 (0.252-0.337) | 0.289 (0.248-0.332) | 0.366 (0.322-0.412) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M-score Sn@95Sp |
|---|---|---|---|---|---|
| All Inv.Can.: subjcat3: Non-cancer (362) vs Invasive Cancer (498) | 0.311 (0.271-0.354) | 0.361 (0.319-0.405) | 0.291 (0.252-0.333) | 0.287 (0.248-0.329) | 0.357 (0.315-0.401) |
| All Inv.Can.: subjcat5b: Stage I/II/III (371) vs Non-cancer (362) | 0.202 (0.162-0.247) | 0.262 (0.217-0.309) | 0.183 (0.145-0.226) | 0.181 (0.143-0.224) | 0.245 (0.202-0.292) |
| All Inv.Can.: subjcat5b: Stage IV (93) vs Non-cancer (362) | 0.774 (0.676-0.854) | 0.774 (0.676-0.854) | 0.731 (0.629-0.818) | 0.72 (0.618-0.809) | 0.85 (0.76-0.915) |
| All Inv.Can.: subjcat5: Stage I/II (301) vs Non-cancer (362) | 0.12 (0.085-0.162) | 0.169 (0.129-0.217) | 0.103 (0.071-0.143) | 0.1 (0.068-0.139) | 0.156 (0.117-0.202) |
| All Inv.Can.: subjcat5: Stage III/IV (163) vs Non-cancer (362) | 0.681 (0.604-0.752) | 0.724 (0.649-0.791) | 0.644 (0.566-0.717) | 0.638 (0.559-0.712) | 0.755 (0.681-0.819) |
| Anorectal: subjcat5b: Stage I/II/III (1) vs Non-cancer (362) | 1 (0.025-1) | 1 (0.025-1) | 1 (0.025-1) | 1 (0.025-1) | 1 (0.025-1) |
| Anorectal: subjcat5b: StageIV (1) vs Non-cancer (362) | 1 (0.025-1) | 1 (0.025-1) | 1 (0.025-1) | 1 (0.025-1) | 1 (0.025-1) |
| Bladder: subjcat5b: Stage I/II/III (1) vs Non-cancer (362) | 0 (0-0.975) | 0 (0-0.975) | 0 (0-0.975) | 0 (0-0.975) | 0 (0-0.975) |
| Breast(HR−): subjcat5b: Stage I/II/III (19) vs Non-cancer (362) | 0.316 (0.126-0.566) | 0.421 (0.203-0.665) | 0.368 (0.163-0.616) | 0.316 (0.126-0.566) | 0.316 (0.126-0.566) |
| Breast(HR−): subjcat5b: Stage IV (3) vs Non-cancer (362) | 0.667 (0.094-0.992) | 0.667 (0.094-0.992) | 0.667 (0.094-0.992) | 0.667 (0.094-0.992) | 0.667 (0.094-0.992) |
| Breast: subjcat5b: Stage I/II/III (165) vs Non-cancer (362) | 0.121 (0.076-0.181) | 0.188 (0.131-0.256) | 0.115 (0.071-0.174) | 0.109 (0.066-0.167) | 0.139 (0.09-0.202) |
| Breast: subjcat5b: Stage IV (5) vs Non-cancer (362) | 0.8 (0.284-0.995) | 0.8 (0.284-0.995) | 0.8 (0.284-0.995) | 0.8 (0.284-0.995) | 0.8 (0.284-0.995) |
| Cancer of unknown primary: subjcat5b: Stage I/II/III (1) vs Non-cancer (362) | 0 (0-0.975) | 1 (0.025-1) | 0 (0-0.975) | 0 (0-0.975) | 1 (0.025-1) |
| Cancer of unknown primary: subjcat5b: Stage IV (7) vs Non-cancer (362) | 0.714 (0.29-0.963) | 0.714 (0.29-0.963) | 0.714 (0.29-0.963) | 0.714 (0.29-0.963) | 0.857 (0.421-0.996) |
| Cervical cancer (cervix): subjcat5b: Stage I/II/III (6) vs Non-cancer (362) | 0.333 (0.043-0.777) | 0.167 (0.004-0.641) | 0.167 (0.004-0.641) | 0.167 (0.004-0.641) | 0.333 (0.043-0.777) |
| Cervical cancer (cervix): subjcat5b: Stage IV (2) vs Non-cancer (362) | 0 (0-0.842) | 0 (0-0.842) | 0 (0-0.842) | 0 (0-0.842) | 1 (0.158-1) |
| Colorectal: subjcat5b: Stage I/II/III (29) vs Non-cancer (362) | 0.414 (0.235-0.611) | 0.448 (0.264-0.643) | 0.345 (0.179-0.543) | 0.345 (0.179-0.543) | 0.517 (0.325-0.706) |
| Colorectal: subjcat5b: Stage IV (10) vs Non-cancer (362) | 1 (0.692-1) | 1 (0.692-1) | 1 (0.692-1) | 1 (0.692-1) | 1 (0.692-1) |
| Esophageal: subjcat5b: Stage I/II/III (7) vs Non-cancer (362) | 0.429 (0.099-0.816) | 0.571 (0.184-0.901) | 0.429 (0.099-0.816) | 0.429 (0.099-0.816) | 0.429 (0.099-0.816) |
| Gastric: subjcat5b: Stage I/II/III (9) vs Non-cancer (362) | 0.444 (0.137-0.788) | 0.444 (0.137-0.788) | 0.333 (0.075-0.701) | 0.333 (0.075-0.701) | 0.333 (0.075-0.701) |
| Gastric: subjcat5b: Stage IV (4) vs Non-cancer (362) | 0.5 (0.068-0.932) | 0.5 (0.068-0.932) | 0.25 (0.006-0.806) | 0.25 (0.006-0.806) | 0.75 (0.194-0.994) |
| Head/Neck: subjcat5b: Stage I/II/III (7) vs Non-cancer (362) | 0.143 (0.004-0.579) | 0.286 (0.037-0.71) | 0.143 (0.004-0.579) | 0.143 (0.004-0.579) | 0.286 (0.037-0.71) |
| Head/Neck: subjcat5b: Stage IV (5) vs Non-cancer (362) | 0.6 (0.147-0.947) | 0.8 (0.284-0.995) | 0.8 (0.284-0.995) | 0.8 (0.284-0.995) | 0.8 (0.284-0.995) |
| Hepatobiliary: subjcat5b: Stage I/II/III (8) vs Non-cancer (362) | 0.375 (0.085-0.755) | 0.5 (0.157-0.843) | 0.5 (0.157-0.843) | 0.5 (0.157-0.843) | 0.625 (0.245-0.915) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M- score Sn@95Sp |
|---|---|---|---|---|---|
| Hepatobiliary: subjcat5b: Stage IV (6) vs Non-cancer (362) | 1 (0.541-1) | 1 (0.541-1) | 1 (0.541-1) | 1 (0.541-1) | 1 (0.541-1) |
| HER2+/HR+: subjcat5b: Stage I/II/III (28) vs Non-cancer (362) | 0.107 (0.023-0.282) | 0.143 (0.04-0.327) | 0.107 (0.023-0.282) | 0.107 (0.023-0.282) | 0.107 (0.023-0.282) |
| HER2+/HR−: subjcat5b: Stage I/II/III (3) vs Non-cancer (362) | 0 (0-0.708) | 0 (0-0.708) | 0 (0-0.708) | 0 (0-0.708) | 0 (0-0.708) |
| HER2+/HR−: subjcat5b: Stage IV (2) vs Non-cancer (362) | 0.5 (0.013-0.987) | 0.5 (0.013-0.987) | 0.5 (0.013-0.987) | 0.5 (0.013-0.987) | 0.5 (0.013-0.987) |
| HER2+: subjcat5b: Stage I/II/III (31) vs Non-cancer (362) | 0.097 (0.02-0.258) | 0.129 (0.036-0.298) | 0.097 (0.02-0.258) | 0.097 (0.02-0.258) | 0.097 (0.02-0.258) |
| HER2+: subjcat5b: Stage IV (2) vs Non-cancer (362) | 0.5 (0.013-0.987) | 0.5 (0.013-0.987) | 0.5 (0.013-0.987) | 0.5 (0.013-0.987) | 0.5 (0.013-0.987) |
| HR+/HER2−: subjcat5b: Stage I/II/III (107) vs Non-cancer (362) | 0.084 (0.039-0.154) | 0.159 (0.095-0.242) | 0.065 (0.027-0.13) | 0.065 (0.027-0.13) | 0.112 (0.059-0.188) |
| HR+/HER2−: subjcat5b: Stage IV (2) vs Non-cancer (362) | 1 (0.158-1) | 1 (0.158-1) | 1 (0.158-1) | 1 (0.158-1) | 1 (0.158-1) |
| HR+: subjcat5b: Stage I/II/III (135) vs Non-cancer (362) | 0.089 (0.047-0.15) | 0.156 (0.099-0.228) | 0.074 (0.036-0.132) | 0.074 (0.036-0.132) | 0.111 (0.064-0.177) |
| HR−: subjcat5b: Stage I/II/III (19) vs Non-cancer (362) | 0.316 (0.126-0.566) | 0.421 (0.203-0.665) | 0.368 (0.163-0.616) | 0.316 (0.126-0.566) | 0.316 (0.126-0.566) |
| HR+: subjcat5b: Stage IV (2) vs Non-cancer (362) | 1 (0.158-1) | 1 (0.158-1) | 1 (0.158-1) | 1 (0.158-1) | 1 (0.158-1) |
| HR−: subjcat5b: Stage IV (3) vs Non-cancer (362) | 0.667 (0.094-0.992) | 0.667 (0.094-0.992) | 0.667 (0.094-0.992) | 0.667 (0.094-0.992) | 0.667 (0.094-0.992) |
| Lung: subjcat5b: Stage I/II/III (27) vs Non-cancer (362) | 0.444 (0.255-0.647) | 0.518 (0.319-0.713) | 0.444 (0.255-0.647) | 0.444 (0.255-0.647) | 0.556 (0.353-0.745) |
| Lung: subjcat5b: Stage IV (19) vs Non-cancer (362) | 0.842 (0.604-0.966) | 0.895 (0.669-0.987) | 0.895 (0.669-0.987) | 0.842 (0.604-0.966) | 0.895 (0.669-0.987) |
| Lymphoma: subjcat5b: Stage I/II/III (13) vs Non-cancer (362) | 0.615 (0.316-0.861) | 0.615 (0.316-0.861) | 0.462 (0.192-0.749) | 0.462 (0.192-0.749) | 0.692 (0.386-0.909) |
| Lymphoma: subjcat5b: Stage IV (5) vs Non-cancer (362) | 0.6 (0.147-0.947) | 0.4 (0.053-0.853) | 0.4 (0.053-0.853) | 0.4 (0.053-0.853) | 0.8 (0.284-0.995) |
| Melanoma: subjcat5b: Stage I/II/III (5) vs Non-cancer (362) | 0.2 (0.005-0.716) | 0 (0-0.522) | 0 (0-0.522) | 0 (0-0.522) | 0 (0-0.522) |
| Melanoma: subjcat5b: Stage IV (3) vs Non-cancer (362) | 1 (0.292-1) | 0.667 (0.094-0.992) | 0.667 (0.094-0.992) | 0.667 (0.094-0.992) | 1 (0.292-1) |
| Other/missing: subjcat5b: Stage I/II/III (11) vs Non-cancer (362) | 0.182 (0.023-0.518) | 0.182 (0.023-0.518) | 0.182 (0.023-0.518) | 0.182 (0.023-0.518) | 0.182 (0.023-0.518) |
| Other: subjcat5b: Stage I/II/III (5) vs Non-cancer (362) | 0 (0-0.522) | 0 (0-0.522) | 0 (0-0.522) | 0 (0-0.522) | 0.2 (0.005-0.716) |
| Other: subjcat5b: Stage IV (2) vs Non-cancer (362) | 0.5 (0.013-0.987) | 0.5 (0.013-0.987) | 0.5 (0.013-0.987) | 0.5 (0.013-0.987) | 0.5 (0.013-0.987) |
| Ovarian: subjcat5b: Stage I/II/III (5) vs Non-cancer (362) | 0.6 (0.147-0.947) | 0.6 (0.147-0.947) | 0.6 (0.147-0.947) | 0.6 (0.147-0.947) | 0.6 (0.147-0.947) |
| Ovarian: subjcat5b: Stage IV (2) vs Non-cancer (362) | 1 (0.158-1) | 1 (0.158-1) | 1 (0.158-1) | 1 (0.158-1) | 1 (0.158-1) |
| Pancreas: subjcat5b: Stage I/II/III (8) vs Non-cancer (362) | 0.375 (0.085-0.755) | 0.5 (0.157-0.843) | 0.5 (0.157-0.843) | 0.5 (0.157-0.843) | 0.625 (0.245-0.915) |

TABLE 2-continued

Comparison of Convolutional Neural Network Performance to other Classifiers

| Row Name | B-score Ywbc: Sn@95Sp | CNN score Sn@95Sp | CNN score Sn@98Sp | CNN score Sn@99Sp | M-score Sn@95Sp |
|---|---|---|---|---|---|
| Pancreas: subjcat5b: Stage IV (14) vs Non-cancer (362) | 0.857 (0.572-0.982) | 0.929 (0.661-0.998) | 0.857 (0.572-0.982) | 0.857 (0.572-0.982) | 0.929 (0.661-0.998) |
| Prostate: subjcat5b: StageI/II/III (53) vs Non-cancer (362) | 0 (0-0.067) | 0.038 (0.005-0.13) | 0 (0-0.067) | 0 (0-0.067) | 0 (0-0.067) |
| Prostate: subjcat5b: Stage IV (2) vs Non-cancer (362) | 0 (0-0.842) | 0 (0-0.842) | 0 (0-0.842) | 0 (0-0.842) | 0 (0-0.842) |
| Renal: subjcat5b: Stage I/II/III (11) vs Non-cancer (362) | 0.182 (0.023-0.518) | 0.182 (0.023-0.518) | 0 (0-0.285) | 0 (0-0.285) | 0.182 (0.023-0.518) |
| Renal: subjcat5b: Stage IV (2) vs Non-cancer (362) | 0.5 (0.013-0.987) | 1 (0.158-1) | 0.5 (0.013-0.987) | 0.5 (0.013-0.987) | 0.5 (0.013-0.987) |
| Thyroid: subjcat5b: Stage I/II/III (3) vs Non-cancer (362) | 0 (0-0.708) | 0.333 (0.008-0.906) | 0 (0-0.708) | 0 (0-0.708) | 0 (0-0.708) |
| Thyroid: subjcat5b: Stage IV (2) vs Non-cancer (362) | 0.5 (0.013-0.987) | 0 (0-0.842) | 0 (0-0.842) | 0 (0-0.842) | 0 (0-0.842) |
| TNBC: subjcat5b: Stage I/II/III (16) vs Non-cancer (362) | 0.375 (0.152-0.646) | 0.5 (0.247-0.753) | 0.438 (0.198-0.701) | 0.375 (0.152-0.646) | 0.375 (0.152-0.646) |
| TNBC: subjcat5b: Stage IV (1) vs Non-cancer (362) | 1 (0.025-1) | 1 (0.025-1) | 1 (0.025-1) | 1 (0.025-1) | 1 (0.025-1) |
| Uterine: subjcat5b: Stage I/II/III (7) vs Non-cancer (362) | 0 (0-0.41) | 0.286 (0.037-0.71) | 0.143 (0.004-0.579) | 0.143 (0.004-0.579) | 0.143 (0.004-0.579) |
| Uterine: subjcat5b: Stage IV (2) vs Non-cancer (362) | 1 (0.158-1) | 0.5 (0.013-0.987) | 0 (0-0.842) | 0 (0-0.842) | 1 (0.158-1) |

Example 8: Combining Convolutional Neural Network (CNN) Analysis with Other Types of Analysis for Classifications FIG. 42A-42D depicts classification performance for a test of subjects when CNN analysis is combined with other types of analysis. Combined (ensemble) models were generated using cross-validated training set scores for two or more classifiers. Each participant's training set classifier scores (e.g., CNN analysis score, M-score) were used as features to predict cancer status in the training set using simple logistic regression. The trained models (the trained logistic regression) is then applied in the test set, where the test set classifier scores are the inputs to each model and the output is probability of cancer.

Most combined analysis (logistic regression models that use multiple classification model outputs as input) showed improvement at different specificity cutoff values. For example, a logistic regression model trained on the combined fragment length and CNN model scores showed consistent improvement over either analysis alone at specificity levels higher than 96%. Further, a logistic regression model that used both the M-score and CNN output score as inputs to the logistic regression model also showed consistent improvement over either analysis alone over specificity levels higher than 95%.

Figure 42A:
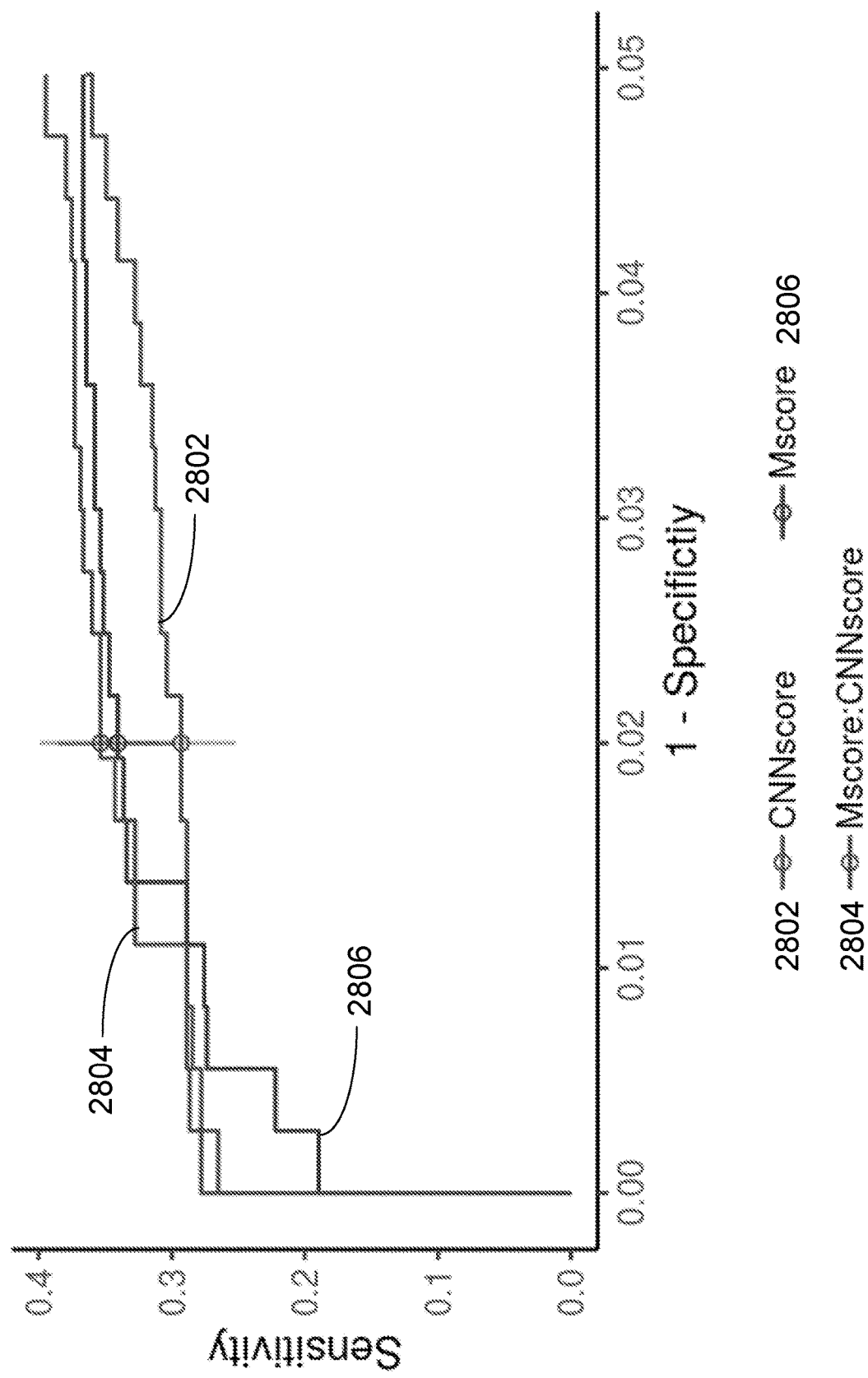
FIG. 42A through 42D depicts classification performance when CNN analysis is combined with other types of analysis (42A: M-score analysis; 42B: fragment length analysis; 42-C: B-score analysis, and 42D: allelic ratio analysis).

FIG. 42A shows the performance of a trained CNN score model of the present disclosure against a test population by itself (line 2802), the performance of the M-score classifier disclosed in U.S. patent application Ser. No. 16/352,602 entitled "Anomalous Fragment Detection and classification," filed Mar. 13, 2019, which is hereby incorporated by reference, against the same test population by itself (line 2806) and the performance of a logistic regression model that uses, as input features, the output scores of the CNN model and the M-score model against the same test population (line 2804).

Figure 42B:
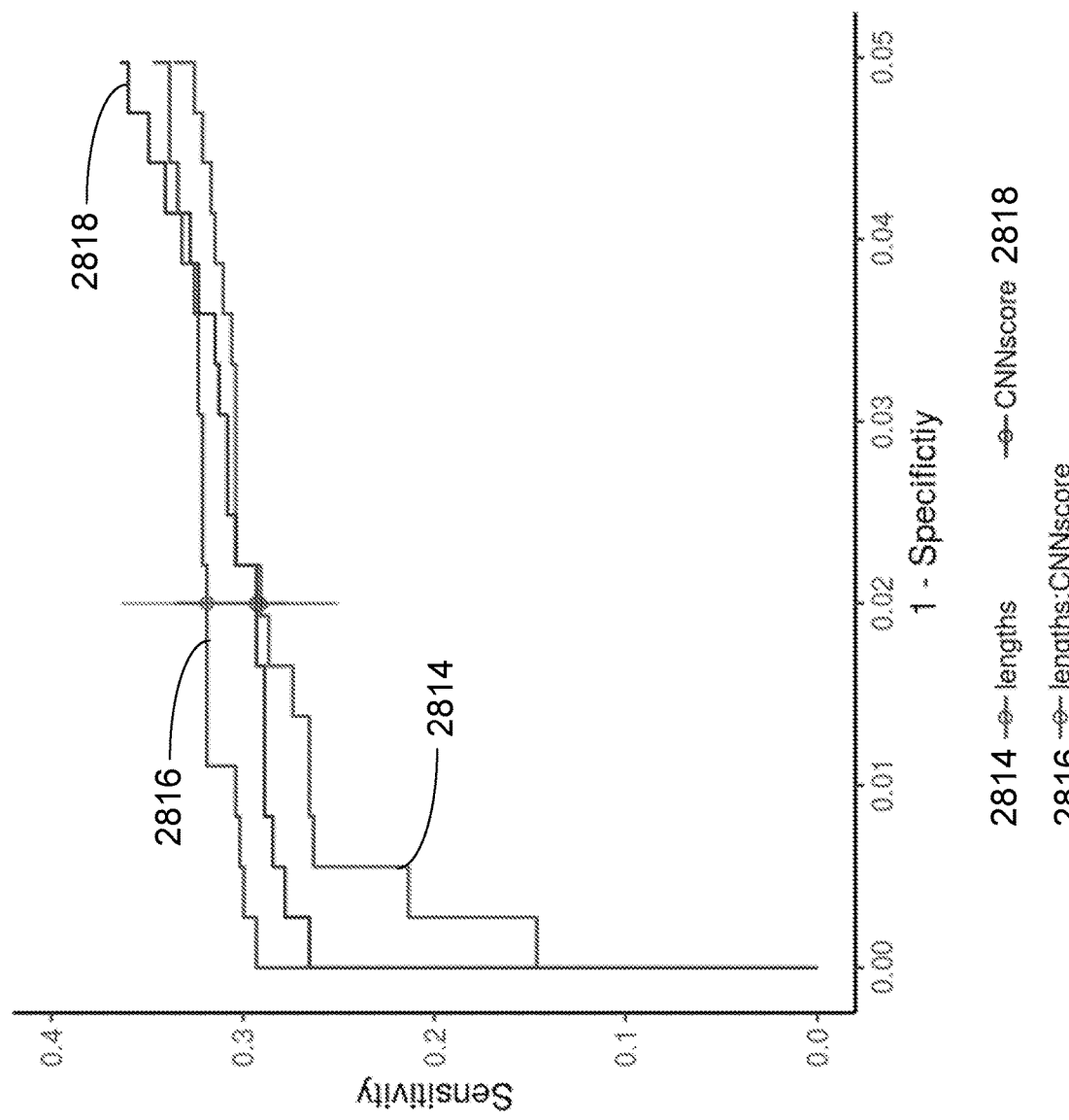

FIG. 42B shows the performance of a trained CNN score model of the present disclosure against a test population by itself (line 2818), the performance of a lengths classifier disclosed in U.S. Provisional Application No. 62/827,682, entitled "Systems and Methods for Using Fragment Lengths as a Predictor of Cancer," filed Apr. 1, 2019, which is hereby incorporated by reference, against the same test population by itself (line 2814) and the performance of a logistic regression model that uses, as input features, the output scores of the CNN model and the lengths classifier against the same test population (line 2816).

Figure 42C:
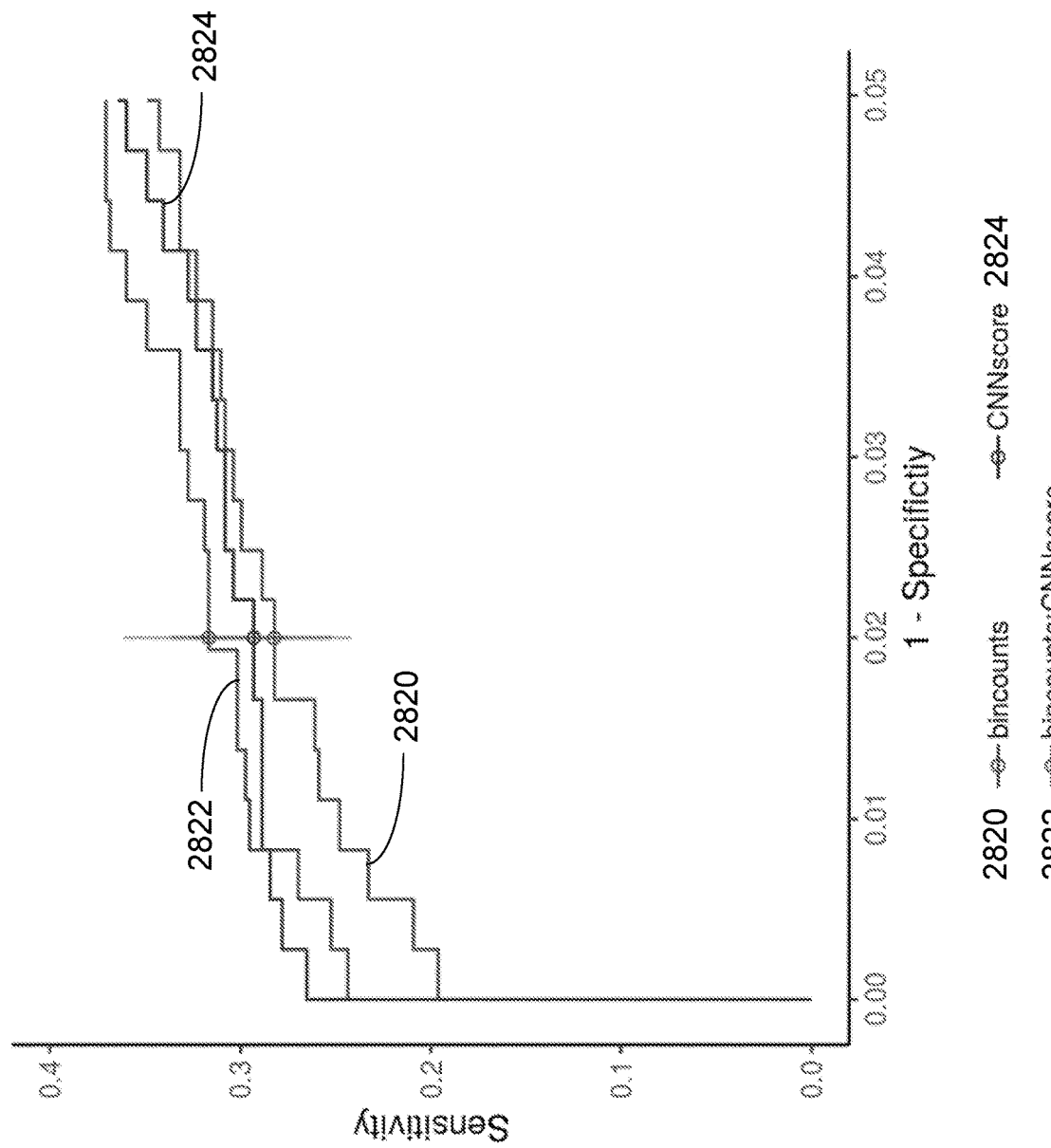

FIG. 42C shows the performance of a trained CNN score model of the present disclosure against a test population by itself (line 2824), the performance of a B-score classifier (bincounts) disclosed in U.S. patent application Ser. No. 16/352,739, entitled "Method and System for Selecting, Managing, and Analyzing Data of High Dimensionality," filed Mar. 13, 2019, which is hereby incorporated by reference, against the same test population by itself (line 2820) and the performance of a logistic regression model that uses, as input features, the output scores of the CNN model and the B-score classifier against the same test population (line 2822).

Figure 42D:
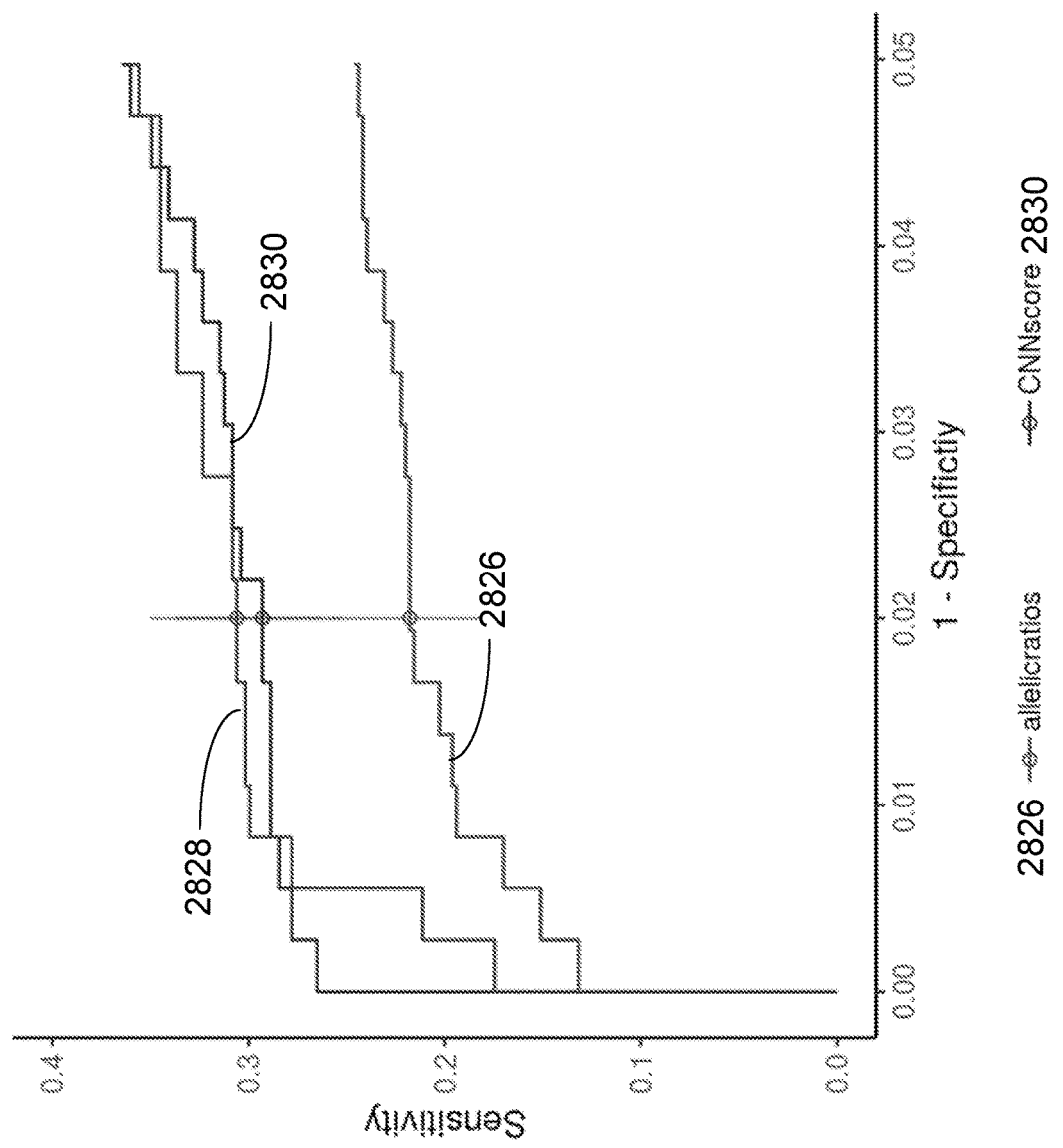

FIG. 42D shows the performance of a trained CNN score model of the present disclosure against a test population by itself (line 2830), the performance of an allelic ratios classifier disclosed in International Publication No. WO 2012/071621, filed Nov. 30, 2011, and entitled "Detection of Genetic or Molecular Aberrations Associated with Cancer," which is hereby incorporated by reference, against the same test population by itself (line 2826) and the performance of a logistic regression model that uses, as input features, the output scores of the CNN model and the allelic ratios classifier against the same test population (line 2828).

Although an overall predictive model in the form of logistic regression has been used in these examples, it will be appreciated that the output of any combination of the models (separate predictive models) disclosed in this example can serve as input to an overall predictive model that is other than a logistic regression. For example, any of the techniques for combining the output of separate predictive models into an overall predictive model disclosed in U.S. patent application Ser. No. 16/384,784 entitled "Multi-Assay Prediction Model for Cancer Detection," filed Apr. 15, 2019 (the "'784 application"), which is hereby incorporated by reference, may be used.

While the above examples each make use of the model scores of two different classification models as input into the overall predictive model, in other embodiments, the model scores from two, three, four, five, six, seven, eight, nine, ten, or more than ten different classification models can be used as input to the overall predictive model in other embodiments of the present disclosure.

CONCLUSION

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A computer system for classifying a cancer condition, in a plurality of different cancer conditions, the computer system comprising:
   at least one processor;
   a graphical processing unit having a graphical processing memory configured to store a network architecture; and
   a memory, the memory storing at least one program for execution by the at least one processor, the at least one program comprising instructions for:
   (A) obtaining, for each respective training subject in a plurality of training subjects of a species: (i) a cancer condition and (ii) a genotypic data construct that includes genotypic information corresponding to locations of a reference genome of the species, thereby obtaining a plurality of genotypic data constructs;
   (B) formatting each genotypic data construct in the plurality of genotypic data constructs into a corresponding vector set comprising one or more corresponding vectors, thereby creating a plurality of vector sets;
   (C) providing the plurality of vector sets to the network architecture that includes at least (i) a first neural network path comprising a first plurality of layers including at least a first network layer associated with at least a first filter comprising a first set of filter weights and (ii) a scorer, wherein the first network layer sequentially receives vector sets in the plurality of vector sets;

(D) obtaining a plurality of scores from the scorer, wherein each score in the plurality of scores corresponds to an input of one of the vector sets in the plurality of vector sets into the network architecture; and (E) using a comparison of respective scores in the plurality of scores to the corresponding cancer condition of the corresponding training subject in the plurality of training subjects to adjust at least the first set of filter weights thereby training the network architecture to classify a cancer condition, in the plurality of cancer conditions.

2. The computer system of claim 1, wherein the genotypic information comprises a methylation status of a plurality of CpG sites associated with at least a portion of a training subject genome and wherein the methylation status is obtained via performance of a DNA methylation assay.

3. The computer system of claim 1, wherein:
the scorer provides a k-dimensional score for each respective vector set in the plurality of vector sets, wherein k is a positive integer of 2 or greater, and
each element in the k-dimensional score represents a probability or likelihood that the training subject associated with the respective vector set has a corresponding cancer condition in the plurality of cancer conditions.

4. The computer system of claim 1, wherein
the scorer comprises a plurality of fully-connected layers and a multinomial logistic regression cost layer, and
a fully-connected layer in the plurality of fully-connected layers feeds into the multinomial logistic regression cost layer.

5. The computer system of claim 1, wherein the scorer comprises a binomial logistic regression cost layer.

6. The computer system of claim 1, wherein each vector in each vector set comprises the genotypic information for a corresponding different chromosome in a plurality of chromosomes of the species.

7. The computer system of claim 1, wherein:
the first plurality of layers further comprises a second network layer;
the second network layer includes at least a second filter that comprises a second set of filter weights;
the output of each layer in the first plurality of layers other than a final layer in the first plurality of layers serves as input into another layer in the first plurality of layers;
and wherein the providing (C), responsive to input of a respective vector set in the plurality of vector sets into the network architecture, performs a procedure comprising:
 (a) inputting a first plurality of input values into the first network layer as a first function of values in the respective vector set,
 (b) causing the first network layer to feed a first plurality of intermediate values computed as a second function of: (i) at least the first set of filter weights and (ii) the first plurality of input values, into another layer in the first neural network path,
 (c) causing the second network layer to feed a second plurality of intermediate values, as a third function of (i) at least the second set of filter weights and (ii) input values received by the second network layer from another layer in the first neural network path, and
 (d) causing a final layer in the first neural network path to feed a plurality of values from the final layer into the scorer.

8. The computer system of claim 7, wherein
the at least first filter of the first network layer comprises a pair of filters that are each independently initialized to randomized values prior to the providing (C), and
the at least second filter of the second network layer is a pair of filters that are independently initialized to randomized values prior to the providing (C).

9. The computer system of claim 7, wherein the first neural network path further comprises a first pooling layer and a second pooling layer, and wherein the procedure further comprises:
causing the first pooling layer to feed a third plurality of intermediate values computed as a first pooling function of the first plurality of intermediate values from the first network layer into another layer in the first neural network path, and
causing the second pooling layer to feed a fourth plurality of intermediate values computed as a second pooling function of the second plurality of intermediate values from the second network layer into another layer in the first neural network path or into the scorer.

10. The computer system of claim 7, wherein:
all or a portion of the reference genome is represented by a plurality of bins, each respective bin representing a different and non-overlapping region of the reference genome, and
the genotypic information for each respective training subject comprises a first bin count for each respective bin in the plurality of bins, each respective first bin count representative of first genotypic information that has been measured from a biological sample obtained from the respective training subject and that maps onto the region of the reference genome corresponding to the respective bin.

11. The computer system of claim 10, wherein the first bin count representative of first genotypic information is one of:
a number of sequence reads in sequencing data measured from cell-free nucleic acids in the biological sample that maps onto the region of the reference genome corresponding to the respective bin,
a number of sequence reads in sequencing data measured from white blood cells in the biological sample that maps onto the region of the reference genome corresponding to the respective bin,
a respective first number of paired sequence reads in sequencing data measured from cell-free nucleic acids in the biological sample that map onto the region of the reference genome corresponding to the respective bin, wherein each paired sequence read in the respective first number of paired sequence reads maps to a sequence in the region of the genome of the species that is within a first size range,
a number of sequence reads in sequencing data obtained using a methylation sequencing assay of cell-free nucleic acids in the biological sample that have a predetermined methylation state and that map onto the region of the reference genome corresponding to the respective bin,
a mean nucleic acid length of sequence reads in sequencing data measured from cell-free nucleic acids in the biological sample that map onto the portion of the reference genome corresponding to the respective bin,
an allelic ratio of sequence reads measured from cell-free nucleic acid fragments in the biological sample mapping onto the region of the reference genome corresponding to the respective bin, and a number of mutations identified in sequence reads measured from cell-free nucleic acid in the biological sample mapping onto the region of the reference genome corresponding to the respective bin.

12. The computer system of claim 10, wherein:

the genotypic information for each respective training subject comprises a second bin count for each respective bin in the plurality of bins, each respective second bin count representative of second genotypic information that has been measured from the biological sample and that maps onto the different region of the reference genome corresponding to the respective bin, a first vector set of a first training subject comprises a plurality of vectors that is divided into a first track comprising a first subset of the plurality of vectors of the vector set and a second subset of the plurality of vectors of the vector set, each respective vector in the first subset comprises the first bin count for the different chromosome in the plurality of chromosomes of the species corresponding to the vector, each respective vector in the second subset comprises the second bin count for the different chromosome in the plurality of chromosomes of the species corresponding to the respective vector, the network architecture comprises a plurality of neural network paths including a respective first neural network path and a respective second neural network path for each respective chromosome in the plurality of chromosomes, each respective first neural network path and respective second neural network path in the plurality of neural network paths comprises a first network layer and a second network layer, the inputting step (a) of the procedure inputs:

for each respective vector in the first subset of the first vector set, the respective vector into the first network layer of the respective first neural network path in the plurality of neural networks that represents the chromosome associated with the respective vector, and for each respective vector in the second subset of the first vector set, the respective vector into the first network layer of the respective second neural network path in the plurality of neural network paths that represents the chromosome associated with the respective vector, and the procedure causes a respective final layer of each neural network path in the plurality of neural network paths to feed a different plurality of values from the respective final layer into the scorer.

13. The computer system of claim 12, wherein the first bin count and the second bin count are different from each other and, for each respective bin in the plurality of bins, are each independently one of:

a number of sequence reads in sequencing data measured from cell-free nucleic acids in the biological sample that maps onto the region of the reference genome corresponding to the respective bin, a number of sequence reads in sequencing data measured from white blood cells in the biological sample that maps onto the region of the reference genome corresponding to the respective bin, a respective first number of paired sequence reads in sequencing data measured from cell-free nucleic acids in the biological sample that map onto the region of the reference genome corresponding to the respective bin, wherein each paired sequence read in the respective first number of paired sequence reads maps to a sequence in the region of the genome of the species that is within a first size range, a number of sequence reads in sequencing data obtained using a methylation sequencing assay of cell-free nucleic acids in the biological sample that have a predetermined methylation state and that map onto the region of the reference genome corresponding to the respective bin, a mean nucleic acid length of sequence reads in sequencing data measured from cell-free nucleic acids in the biological sample that map onto the region of the reference genome corresponding to the respective bin, an allelic ratio of sequence reads measured from cell-free nucleic acid fragments in the biological sample mapping onto the region of the reference genome corresponding to the respective bin, and a number of mutations identified in sequence reads measured from cell-free nucleic acid in the biological sample mapping onto the region of the reference genome corresponding to the respective bin.

14. The computer system of claim 10, wherein:

the genotypic information for each respective training subject comprises a second bin count for each respective bin in the plurality of bins, each respective second bin count representative of second genotypic information that has been measured from the biological sample and that maps onto the different region of the reference genome corresponding to the respective bin, the genotypic information for each respective training subject comprises a third bin count for each respective bin in the plurality of bins, each respective third bin count representative of third genotypic information that has been measured from the biological sample and that maps onto the different region of the reference genome corresponding to the respective bin, a first vector set of a first training subject comprises a plurality of vectors that is divided into (i) a first track comprising a first subset of the plurality of vectors of the first vector set, (ii) a second track comprising a second subset of the plurality of vectors of the first vector set, and (iii) a third track comprising a third subset of the plurality of vectors of the first vector set, each respective vector in the first subset comprises the first bin count for the different chromosome in the plurality of chromosomes of the species corresponding to the vector, each respective vector in the second subset comprises the second bin count for the different chromosome in the plurality of chromosomes of the species corresponding to the vector, each respective vector in the third subset comprises the third bin count for the different chromosome in the plurality of chromosomes of the species corresponding to the respective vector, the network architecture comprises a plurality of neural network paths including a respective first neural network path, a respective second neural network path, and a respective third neural network path for each respective chromosome in the plurality of chromosomes, each respective first neural network path, respective second neural network path, and respective third neural network path in the plurality of neural network paths comprises a first network layer and a second network layer, the providing (C) inputs:
- for each respective vector in the first subset of the first vector set, the respective vector into the first network layer of the respective first neural network path in the plurality of neural network paths that represents the chromosome associated with the respective vector,
- for each respective vector in the second subset of the first vector set, the respective vector into the first network layer of the respective second neural network path in the plurality of neural network paths that represents the chromosome associated with the respective vector, and
- for each respective vector in the third subset of the first vector set, the vector into the first network layer of the respective third neural network path in the plurality of neural network paths that represents the chromosome associated with the respective vector, and
- a respective final layer of each respective neural network path in the plurality of neural network paths feeds a different plurality of values from the respective final layer into the scorer.

15. The computer system of claim 14, wherein the first bin count, the second bin count, and the third bin count are different from each other and, for each respective bin in the plurality of bins, are each independently one of:
- a number of sequence reads in sequencing data measured from cell-free nucleic acids in the biological sample that maps onto the region of the reference genome corresponding to the respective bin,
- a number of sequence reads in sequencing data measured from white blood cells in the biological sample that maps onto the region of the reference genome corresponding to the respective bin,
- a respective first number of paired sequence reads in sequencing data measured from cell-free nucleic acids in the biological sample that map onto the region of the reference genome corresponding to the respective bin, wherein each paired sequence read in the respective first number of paired sequence reads maps to a sequence in the region of the genome of the species that is within a first size range,
- a number of sequence reads in sequencing data obtained using a methylation sequencing assay of cell-free nucleic acids in the biological sample that have a predetermined methylation state and that map onto the region of the reference genome corresponding to the respective bin,
- a mean nucleic acid length of sequence reads in sequencing data measured from cell-free nucleic acids in the biological sample that map onto the region of the reference genome corresponding to the respective bin,
- an allelic ratio of sequence reads measured from cell-free nucleic acid fragments in the biological sample mapping onto the region of the reference genome corresponding to the respective bin, and
- a number of mutations identified in sequence reads measured from cell-free nucleic acid in the biological sample mapping onto the region of the reference genome corresponding to the respective bin.

16. The computer system of claim 7, wherein:
the network architecture includes a plurality of neural network paths, the plurality of neural network paths comprising at least one different neural network path for each chromosome in the plurality of chromosomes,
each different neural network path comprises a first network layer and a second network layer,
the inputting step (a) of the procedure inputs, for each respective vector in the respective vector set, the respective vector into the first network layer of the respective neural network path that represents the chromosome associated with the respective vector, and
a respective final layer of each neural network path in the plurality of neural network paths feeds a different plurality of values from the respective final layer into the scorer.

17. The computer system of claim 16, wherein:
the network architecture comprises a plurality of first filters, each respective first filter in the plurality of first filters comprising a corresponding first set of filter weights and corresponding to a first network layer in a corresponding neural network path in the plurality of neural network paths,
the network architecture comprises a plurality of second filters, each respective second filter in the plurality of second filters comprising a corresponding second set of filter weights and corresponding to a second network layer in a corresponding neural network path in the plurality of neural network paths,
the procedure convolves each first filter in the first plurality of filters against a corresponding first network layer in the plurality of neural network paths with a first predetermined stride, and
the procedure convolves each second filter in the plurality of second filters against a corresponding second network layer in the plurality of neural network paths with a second predetermined stride.

18. The computer system of claim 17, wherein:
the plurality of neural network paths is twenty-two, each respective neural network path in the plurality of neural network paths for a different autosomal human chromosome,
the plurality of second filters comprises twenty-two second filters,
the first predetermined stride is between 2 and 10, and
the second predetermined stride is between 1 and 5.

19. The computer system of claim 7, wherein:
all or a portion of the reference genome is represented by a plurality of bins, each respective bin in the plurality of bins representing a different and non-overlapping portion of the reference genome, and
the genotypic information for each respective training subject in the plurality of training subjects comprises a first bin count for each respective bin in the plurality of bins, each respective first bin count representative of a number of sequence reads in sequencing data measured from cell-free nucleic acids in a biological sample obtained from the training subject that maps onto the different region of the reference genome corresponding to the respective bin.

20. The computer system of claim 7 wherein:
all or a portion of the genome of the species is represented by a plurality of bins, each respective bin in the plurality of bins representing a different and non-overlapping portion of the reference genome,
the genotypic data construct for each respective training subject in the plurality of training subjects comprises a first bin count for each respective bin in the plurality of bins, each respective first bin count representative of a respective first number of paired sequence reads in sequencing data measured from cell-free nucleic acids in a biological sample obtained from the training subject that map onto the portion of the reference genome corresponding to the respective bin, wherein each respective paired sequence read in the respective first number of paired sequence reads is within a first size range, the genotypic data construct for each training subject further comprises a second bin count for each respective bin in the plurality of bins, each respective second bin count representative of a respective second number of paired sequence reads in sequencing data measured from cell-free nucleic acid in the biological sample obtained from the training subject that map onto the portion of the reference genome corresponding to the respective bin, wherein each respective paired sequence in the respective second number of paired sequence reads is within a second size range, a first vector set in the plurality of vectors sets that is formatted from the genotypic data construct for a first training subject by the formatting (B) is inputted into the network architecture in the form of a first track and a second track, each respective element of each vector in the first track represents the first bin count for the corresponding bin in the plurality of bins, and each respective element of each vector in the second track represents the second bin count for the corresponding bin in the plurality of bins.

21. The computer system of claim 7, wherein:

all or a portion of the genome of the species is represented by a plurality of bins, each respective bin in the plurality of bins representing a different and non-overlapping portion of the reference genome, and the genotypic information for each respective training subject in the plurality of training subjects comprises a first bin count for each respective bin in the plurality of bins, each respective first bin count representative of a number of sequence reads in sequencing data obtained using a methylation sequencing assay of cell-free nucleic acids in the biological sample that have a predetermined methylation state and that map onto the portion of the reference genome corresponding to the respective bin.

22. The computer system of claim 7, wherein:

all or a portion of the reference genome is represented by a plurality of bins, each respective bin in the plurality of bins representing a different and non-overlapping portion of the reference genome, and the genotypic information for each respective training subject in the plurality of training subjects comprises a first bin count for each respective bin in the plurality of bins, each respective first bin count representative of a mean nucleic acid length of sequence reads in sequencing data measured from cell-free nucleic acids in the biological sample that map onto the portion of the reference genome corresponding to the respective bin.

23. The computer system of claim 7, wherein:

all or a portion of the reference genome is represented by a plurality of bins, each respective bin in the plurality of bins representing a different and non-overlapping portion of the reference genome, and the genotypic information for each respective training subject in the plurality of training subjects comprises a first bin count for each respective bin in the plurality of bins, each respective first bin count representative of an allelic ratio of sequence reads measured from cell-free nucleic acid fragments in the biological sample mapping onto the portion of the reference genome corresponding to the respective bin.

24. The computer system of claim 7, wherein:

all or a portion of the reference genome is represented by a plurality of bins, each respective bin in the plurality of bins representing a different and non-overlapping portion of the reference genome, and the genotypic information for each respective training subject in the plurality of training subjects comprises a first bin count for each respective bin in the plurality of bins, each respective first bin count representative of a number of mutations identified in sequence reads measured from cell-free nucleic acid in the biological sample mapping onto the portion of the reference genome corresponding to the respective bin.

25. The computer system of claim 7, wherein a first vector set in the plurality of vectors sets that is formatted from the genotypic data construct for a first training subject by the formatting (B) is inputted into the network architecture.

26. A method for classifying a cancer condition, in a plurality of different cancer conditions, the method comprising:

(A) obtaining, for each respective training subject in a plurality of training subjects of a species: (i) a cancer condition and (ii) a genotypic data construct that includes genotypic information corresponding to locations of a reference genome of the species, thereby obtaining a plurality of genotypic data constructs;

(B) formatting each genotypic data construct in the plurality of genotypic data constructs into a corresponding vector set comprising one or more corresponding vectors, thereby creating a plurality of vector sets;

(C) providing the plurality of vector sets to the network architecture that includes at least (i) a first neural network path comprising a first plurality of layers including at least a first network layer associated with at least a first filter comprising a first set of filter weights and (ii) a scorer, wherein the first network layer sequentially receives vector sets in the plurality of vector sets;

(D) obtaining a plurality of scores from the scorer, wherein each score in the plurality of scores corresponds to an input of one of the vector sets in the plurality of vector sets into the network architecture; and (E) using a comparison of respective scores in the plurality of scores to the corresponding cancer condition of the corresponding training subject in the plurality of training subjects to adjust at least the first set of filter weights thereby training the network architecture to classify a cancer condition, in the plurality of cancer conditions.

27. The method of claim 26, wherein the genotypic information comprises a methylation status of a plurality of CpG sites associated with at least a portion of a training subject genome and wherein the methylation status is obtained via performance of a DNA methylation assay.

28. The method of claim 26, wherein:

the scorer provides a k-dimensional score for each respective vector set in the plurality of vector sets, wherein k is a positive integer of 2 or greater, and each element in the k-dimensional score represents a probability or likelihood that the training subject associated with the respective vector set has a corresponding cancer condition in the plurality of cancer conditions.

29. The method of claim 26, wherein:
the scorer comprises a plurality of fully-connected layers and a multinomial logistic regression cost layer, and
a fully-connected layer in the plurality of fully-connected layers feeds into the multinomial logistic regression cost layer.

30. The method of claim 26, wherein each vector in each vector set comprises the genotypic information for a corresponding different chromosome in a plurality of chromosomes of the species.

31. The method of claim 26, wherein:
the first plurality of layers further comprises a second network layer;
the second network layer includes at least a second filter that comprises a second set of filter weights;
the output of each layer in the first plurality of layers other than a final layer in the first plurality of layers serves as input into another layer in the first plurality of layers;
and wherein the providing (C), responsive to input of a respective vector set in the plurality of vector sets into the network architecture, performs a procedure comprising:
  (a) inputting a first plurality of input values into the first network layer as a first function of values in the respective vector set,
  (b) causing the first network layer to feed a first plurality of intermediate values computed as a second function of: (i) at least the first set of filter weights and (ii) the first plurality of input values, into another layer in the first neural network path,
  (c) causing the second network layer to feed a second plurality of intermediate values, as a third function of (i) at least the second set of filter weights and (ii) input values received by the second network layer from another layer in the first neural network path, and
  (d) causing a final layer in the first neural network path to feed a plurality of values from the final layer into the scorer.

32. The method of claim 31, wherein
the at least first filter of the first network layer comprises a pair of filters that are each independently initialized to randomized values prior to the providing (C), and
the at least second filter of the second network layer is a pair of filters that are independently initialized to randomized values prior to the providing (C).

33. The method of claim 31, wherein the first neural network path further comprises a first pooling layer and a second pooling layer, and wherein the procedure further comprises:
causing the first pooling layer to feed a third plurality of intermediate values computed as a first pooling function of the first plurality of intermediate values from the first network layer into another layer in the first neural network path, and
causing the second pooling layer to feed a fourth plurality of intermediate values computed as a second pooling function of the second plurality of intermediate values from the second network layer into another layer in the first neural network path or into the scorer.

34. The method of claim 31, wherein:
all or a portion of the reference genome is represented by a plurality of bins, each respective bin representing a different and non-overlapping region of the reference genome, and
the genotypic information for each respective training subject comprises a first bin count for each respective bin in the plurality of bins, each respective first bin count representative of first genotypic information that has been measured from a biological sample obtained from the respective training subject and that maps onto the region of the reference genome corresponding to the respective bin.

35. The method of claim 34, wherein the first bin count representative of first genotypic information is one of:
a number of sequence reads in sequencing data measured from cell-free nucleic acids in the biological sample that maps onto the region of the reference genome corresponding to the respective bin,
a number of sequence reads in sequencing data measured from white blood cells in the biological sample that maps onto the region of the reference genome corresponding to the respective bin,
a respective first number of paired sequence reads in sequencing data measured from cell-free nucleic acids in the biological sample that map onto the region of the reference genome corresponding to the respective bin, wherein each paired sequence read in the respective first number of paired sequence reads maps to a sequence in the region of the genome of the species that is within a first size range,
a number of sequence reads in sequencing data obtained using a methylation sequencing assay of cell-free nucleic acids in the biological sample that have a predetermined methylation state and that map onto the region of the reference genome corresponding to the respective bin,
a mean nucleic acid length of sequence reads in sequencing data measured from cell-free nucleic acids in the biological sample that map onto the portion of the reference genome corresponding to the respective bin,
an allelic ratio of sequence reads measured from cell-free nucleic acid fragments in the biological sample mapping onto the region of the reference genome corresponding to the respective bin, and
a number of mutations identified in sequence reads measured from cell-free nucleic acid in the biological sample mapping onto the region of the reference genome corresponding to the respective bin.

36. The method of claim 31, wherein:
the network architecture includes a plurality of neural network paths, the plurality of neural network paths comprising at least one different neural network path for each chromosome in the plurality of chromosomes,
each different neural network path comprises a first network layer and a second network layer,
the inputting step (a) of the procedure inputs, for each respective vector in the respective vector set, the respective vector into the first network layer of the respective neural network path that represents the chromosome associated with the respective vector, and
a respective final layer of each neural network path in the plurality of neural network paths feeds a different plurality of values from the respective final layer into the scorer.

37. The method of claim 36, wherein:
the network architecture comprises a plurality of first filters, each respective first filter in the plurality of first filters comprising a corresponding first set of filter weights and corresponding to a first network layer in a corresponding neural network path in the plurality of neural network paths,
the network architecture comprises a plurality of second filters, each respective second filter in the plurality of second filters comprising a corresponding second set of filter weights and corresponding to a second network layer in a corresponding neural network path in the plurality of neural network paths, the procedure convolves each first filter in the first plurality of filters against a corresponding first network layer in the plurality of neural network paths with a first predetermined stride, and the procedure convolves each second filter in the plurality of second filters against a corresponding second network layer in the plurality of neural network paths with a second predetermined stride.

38. The method of claim 37, wherein:

the plurality of neural network paths is twenty-two, each respective neural network path in the plurality of neural network paths for a different autosomal human chromosome, the plurality of second filters comprises twenty-two second filters, the first predetermined stride is between 2 and 10, and the second predetermined stride is between 1 and 5.

39. A non-transitory computer-readable storage medium having stored thereon program code instructions that, when executed by a processor, cause the processor to perform a method for classifying a cancer condition, in a plurality of different cancer conditions, for a species, the method comprising:

(A) obtaining, for each respective training subject in a plurality of training subjects of a species: (i) a cancer condition and (ii) a genotypic data construct that includes genotypic information corresponding to locations of a reference genome of the species, thereby obtaining a plurality of genotypic data constructs;

(B) formatting each genotypic data construct in the plurality of genotypic data constructs into a corresponding vector set comprising one or more corresponding vectors, thereby creating a plurality of vector sets;

(C) providing the plurality of vector sets to the network architecture that includes at least (i) a first neural network path comprising a first plurality of layers including at least a first network layer associated with at least a first filter comprising a first set of filter weights and (ii) a scorer, wherein the first network layer sequentially receives vector sets in the plurality of vector sets;

(D) obtaining a plurality of scores from the scorer, wherein each score in the plurality of scores corresponds to an input of one of the vector sets in the plurality of vector sets into the network architecture; and (E) using a comparison of respective scores in the plurality of scores to the corresponding cancer condition of the corresponding training subject in the plurality of training subjects to adjust at least the first set of filter weights thereby training the network architecture to classify a cancer condition, in the plurality of cancer conditions.

40. The non-transitory computer-readable storage medium of claim 39, wherein the genotypic information comprises a methylation status of a plurality of CpG sites associated with at least a portion of a training subject genome and wherein the methylation status is obtained via performance of a DNA methylation assay.

* * * * *